(12) United States Patent
Laughlin et al.

(10) Patent No.: US 8,957,114 B2
(45) Date of Patent: Feb. 17, 2015

(54) FORMULATIONS, SALTS AND POLYMORPHS OF TRANSNORSERTRALINE AND USES THEREOF

(75) Inventors: Sharon M. Laughlin, Hudson, MA (US); Michael J. Sizensky, South Grafton, MA (US); Surendra P. Singh, Shrewsbury, MA (US); Harold Scott Wilkinson, Westborough, MA (US); Cai Gu Huang, Sudbury, MA (US); Philip James Bonasia, Needham, MA (US); Susan S. D'Souza, Marlborough, MA (US)

(73) Assignee: Sunovion Pharmaceuticals Inc., Malborough, MA (US)

( * ) Notice: Subject to any disclaimer, the term of this patent is extended or adjusted under 35 U.S.C. 154(b) by 60 days.

(21) Appl. No.: 13/513,170

(22) PCT Filed: Dec. 3, 2010

(86) PCT No.: PCT/US2010/058831
§ 371 (c)(1),
(2), (4) Date: Jan. 9, 2013

(87) PCT Pub. No.: WO2011/069032
PCT Pub. Date: Jun. 9, 2011

(65) Prior Publication Data
US 2013/0116332 A1    May 9, 2013

Related U.S. Application Data

(60) Provisional application No. 61/266,864, filed on Dec. 4, 2009.

(51) Int. Cl.
| | |
|---|---|
| *A01N 33/02* | (2006.01) |
| *A61K 31/135* | (2006.01) |
| *C07C 211/00* | (2006.01) |
| *A61K 9/20* | (2006.01) |
| *A61K 9/48* | (2006.01) |
| *C07C 211/42* | (2006.01) |

(52) U.S. Cl.
CPC ............ *A61K 31/135* (2013.01); *A61K 9/2018* (2013.01); *A61K 9/4858* (2013.01); *C07C 211/42* (2013.01)
USPC .......................................... 514/647; 564/308

(58) Field of Classification Search
CPC ...................................................... C07C 211/42
USPC .......................................... 514/647; 564/308
See application file for complete search history.

(56) References Cited

U.S. PATENT DOCUMENTS

| | | | |
|---|---|---|---|
| 6,899,896 B2 * | 5/2005 | Curatolo et al. | ............... 424/473 |
| 7,087,785 B2 | 8/2006 | Jerussi | |
| 8,329,950 B2 | 12/2012 | Caron | |
| 2001/0044474 A1 | 11/2001 | Curatolo | |
| 2004/0087661 A1 | 5/2004 | Jerussi | |
| 2006/0257475 A1 | 11/2006 | Economou | |
| 2007/0282007 A1 | 12/2007 | Tarantino | |
| 2008/0280993 A1 | 11/2008 | Jerussi | |

FOREIGN PATENT DOCUMENTS

| | | |
|---|---|---|
| WO | 2004-024669 | 3/2004 |
| WO | 2007-006003 | 1/2007 |
| WO | 2007-115185 | 10/2007 |
| WO | 2007-143267 | 12/2007 |
| WO | 2010-132521 | 11/2010 |

OTHER PUBLICATIONS

Zhengzu Han et al.
Search Report and WOISA from PCT/US2010/058831 (Aug. 30, 2011).
Supplemental Search From EP 10835166.9 (Apr. 23, 2013).

\* cited by examiner

*Primary Examiner* — Kendra D Carter
(74) *Attorney, Agent, or Firm* — Heslin, Rothenberg, Farley & Mesiti, P.C.

(57) ABSTRACT

Provided herein are pharmaceutical compositions comprising transnorsertraline, salts and polymorphic forms of transnorsertraline, methods of making the compositions, and methods for their use for the treatment of CNS diseases, including depression.

8 Claims, 9 Drawing Sheets x10 magnification x20 magnification x5 magnification x5 magnification

FORMULATIONS, SALTS AND POLYMORPHS OF TRANSNORSERTRALINE AND USES THEREOF

This application is a §371 national phase application of International Patent Application No. PCT/US2010/058831, filed Dec. 3, 2010, which claims the benefit of U.S. Provisional Patent Application No. 61/266,864, filed Dec. 4, 2009, the entirety entireties of both of which is are incorporated herein by reference.

1. FIELD

Provided herein are pharmaceutical compositions comprising transnorsertraline, salts and polymorphic forms of transnorsertraline, methods of making the compositions, and methods for their use for the treatment of CNS diseases, including depression.

2. BACKGROUND

2.1 Transnorsertraline

Transnorsertraline, i.e., (1R,4S)-trans-4-(3,4-dichlorophenyl)-1,2,3,4-tetrahydro-1-naphthalenamine and (1S,4R)-trans-4-(3,4-dichlorophenyl)-1,2,3,4-tetrahydro-1-naphthalenamine are described in, for example, U.S. Pat. No. 7,087,785 B2 ("the '785 patent"; incorporated herein by reference in its entirety), have the following chemical structures, respectively:

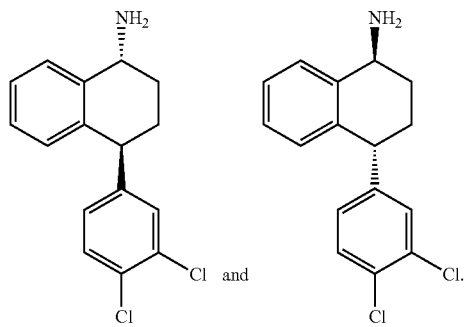 [SMILES: N[C@@H]1CC[C@@H](c2ccc(Cl)c(Cl)c2)c2ccccc21 ; "and" ; N[C@H]1CC[C@H](c2ccc(Cl)c(Cl)c2)c2ccccc21]

Uses of transnorsertraline in the treatment, prevention, or management of affective disorders and other various CNS disorders are also disclosed in the '785 patent. Such disorders include, but are not limited to, depression, mood disorders, anxiety disorders, behavioral disorders, eating disorders, substance abuse disorders, and sexual function disorders.

2.2 Salts and Polymorphic Forms

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise, e.g., from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Solid forms such as salts, crystal forms, e.g., polymorphic forms of a compound are known in the pharmaceutical art to affect, for example, the solubility, stability, flowability, fractability, and compressibility of the compound as well as the safety and efficacy of drug products based on the compound, (see, e.g., Knapman, K. *Modern Drug Discoveries*, 2000:53).

The importance of studying polymorphs was underscored by the case of ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417). Thus, the preparation of solid forms is of great importance in the development of a safe, effective, stable and marketable pharmaceutical compound.

New salts and polymorphic forms of transnorsertraline can further the development of formulations for the treatment, prevention or management of CNS diseases.

2.3 Treatment of Neurological Disorders

Serotonin, i.e., 5-HT, is known to play an important role in the treatment of various CNS disorders. Among others, 5-HT1A (serotonin 1A) receptors provide an important mechanism for controlling 5-HT release in the brain. These receptors are located presynaptically in the raphe nuclei where they function as autoreceptors to inhibit the firing rate of 5-HT neurons. 5-HT$_{1A}$ receptors are also located postsynaptically in corticolimbic regions where they also reduce firing activity of 5-HT neurons. At the initiation of treatment with selective serotonin reuptake inhibitors (SSRIs) or serotonin norepinephrine reuptake inhibitors (SNRIs), the 5-HT$_{1A}$ autoreceptors are activated by 5-HT, leading to a reduction in 5-HT neuronal firing. As SSRI or SNRI treatment continues, however, 5-HT$_{1A}$ autoreceptors become desensitized, and the firing activity is restored. This adaptive change is believed to contribute, at least in part, to the delay in efficacy of SSRIs and SNRIs in treating various neurological disorders.

Therefore, a need exists for the treatment, prevention, or management of various neurological disorders, wherein the desensitization of 5-HT receptors may be minimized and the increase in 5-HT neuronal firing may be maintained.

3. SUMMARY

Provided herein are pharmaceutical compositions comprising transnorsertraline, salts and polymorphic forms of transnorsertraline, methods of making compositions with the salts and polymorphic forms, and methods for their use for the treatment of CNS diseases, including depression.

In one embodiment, provided herein are stable pharmaceutical compositions and/or formulations of transnorsertraline, or a pharmaceutically acceptable salt or solvate thereof.

In another embodiment, provided herein is a salt of transnorsertraline selected from the group consisting of hydrochloride, acetate, L-malate, besylate, benzoate, tosylate, fumarate, hydrobromide, maleate, citrate, phosphate, succinate, L-tartrate, D-tartrate, S-mandelate and pyroglutamate.

In one embodiment, the salt is the hydrochloride salt. In one embodiment, the hydrochloride salt of transnorsertraline is an anhydrous solid. In another embodiment, the hydrochloride salt of transnorsertraline exists as a monohydrate.

In one embodiment, the transnorsertraline hydrochloride is (1R,4S)-transnorsertraline hydrochloride, i.e., (1R,4S)-trans-4-(3,4-dichlorophenyl)-1,2,3,4-tetrahydro-1-naphthalenamine hydrochloride. In another embodiment, the transnorsertraline hydrochloride is (1S,4R)-transnorsertraline hydrochloride, i.e., (1S,4R)-trans-4-(3,4-dichlorophenyl)-1,2,3,4-tetrahydro-1-naphthalenamine hydrochloride.

Also provided herein are methods of treating, preventing or managing neurological disorders comprising administering to a subject (e.g., patient) a formulation, salt or polymorph of transnorsertraline as disclosed herein. Neurological disorders that may be treated, prevented, or managed by the methods provided herein are described in detail herein elsewhere.

In some embodiments, the formulation, salt or polymorph of transnorsertraline is administered in combination with one or more additional therapeutic agents, or pharmaceutically acceptable salts, solvates, or stereoisomers thereof.

4. BRIEF DESCRIPTION OF FIGURES

5. DETAILED DESCRIPTION

Figure 1A:
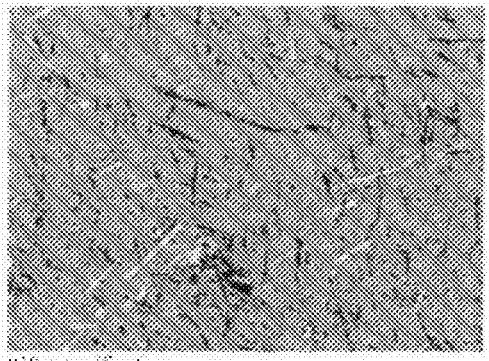
FIG. 1A illustrates the crystal habit of anhydrous transnorsertraline hydrochloride.
Figure 1A:
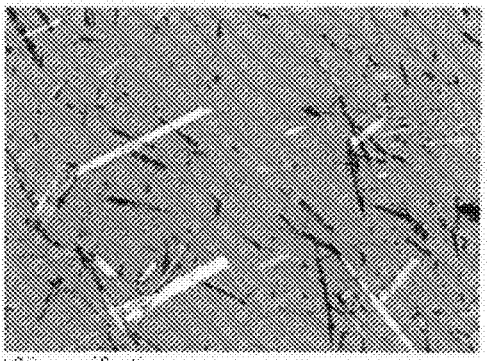

Provided herein are pharmaceutical compositions comprising transnorsertraline, salts and polymorphic forms of transnorsertraline, methods of making compositions with the salts and polymorphic forms, and methods for their use for the treatment of CNS diseases, including depression.

In one embodiment, provided herein are stable pharmaceutical compositions and/or formulations of transnorsertraline, or a pharmaceutically acceptable salt or solvate thereof.

In one embodiment, the stable pharmaceutical compositions and/or formulations of transnorsertraline comprise less than about 3% by weight of a compound of formula (II):

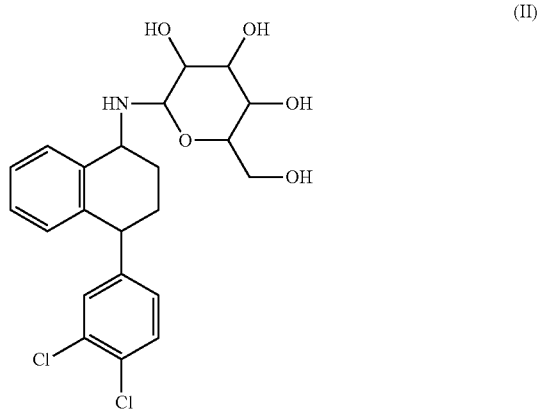 [SMILES: OCC1OC(NC2CCC(c3ccc(Cl)c(Cl)c3)c3ccccc32)C(O)C(O)C1O]

In another embodiment, the stable pharmaceutical compositions and/or formulations of transnorsertraline comprise less than about 1.5% or less than about 1% by weight of a compound of formula (II).

In another embodiment, the stable pharmaceutical compositions and/or formulations of transnorsertraline comprise less than about 4% by weight of compounds of formula (III):

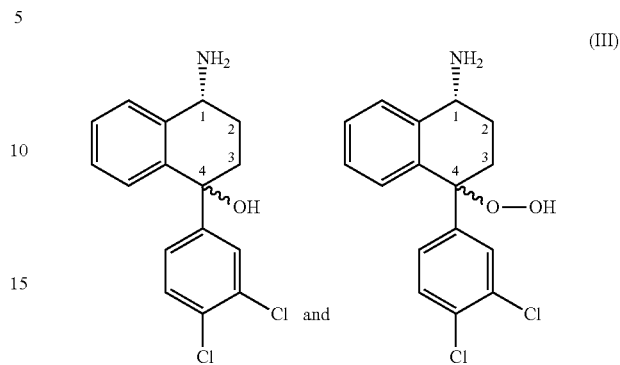

In another embodiment, the stable pharmaceutical compositions and/or formulations of transnorsertraline comprise less than about 2% or less than about 1% by weight of compounds of formula (III)

In another embodiment, the stable pharmaceutical compositions and/or formulations of transnorsertraline comprise less than about 3% by weight of a compound of formula (II) and less than about 4% by weight of compounds of formula (III).

In another embodiment, the stable pharmaceutical compositions and/or formulations of transnorsertraline comprise less than about 1.5% by weight of a compound of formula (II) and less than about 2% by weight of compounds of formula (III).

In another embodiment, the stable pharmaceutical compositions and/or formulations of transnorsertraline comprise less than less than about 1% by weight each of the compounds of formulae (II) and (III).

In certain embodiments, without being bound to any particular theory, it is believed that the compound of formula (II) are adducts of transnorsertraline formed by the decomposition of transnorsertaline in a pharmaceutical dosage form, e.g., a tablet, in the presence of mannose.

In certain embodiments, without being bound to any particular theory, it is believed that the compounds of formula (III) are oxidative decomposition products of transnorsertraline formed by the decomposition of transnorsertaline in a pharmaceutical dosage form, e.g., a tablet, in the presence of dicalcium phosphate (e.g., A-TAB).

In one embodiment, the stable pharmaceutical compositions provided herein are in an immediate-release dosage form.

In another embodiment, the stable pharmaceutical compositions provided herein are in a controlled-release dosage form.

In one embodiment, the pharmaceutical composition comprises transnorsertraline, or a pharmaceutically acceptable salt or solvate thereof, and mannitol, xylitol or a combination thereof. In one embodiment, the pharmaceutical composition comprises transnorsertraline, or a pharmaceutically acceptable salt or solvate thereof, and at least about 5%, 10%, 20%, 30%, 40%, 50%, 60%, 70%, 80%, 85%, 90%, 91%, 92%, 93%, 94%, 95%, 96%, 97% or 98% by weight of mannitol or xylitol.

In another embodiment, the pharmaceutical composition comprises transnorsertraline, or a pharmaceutically acceptable salt or solvate thereof, and mannitol. In one embodiment, the pharmaceutical composition comprises transnorsertraline, or a pharmaceutically acceptable salt or solvate thereof, and at least about 5%, 10%, 20%, 30%, 40%, 50%, 60%, 70%, 80%, 85%, 90%, 91%, 92%, 93%, 94%, 95%, 96%, 97% or 98% by weight of mannitol.

In one embodiment, provided herein is a stable pharmaceutical composition which comprises transnorsertraline, or a pharmaceutically acceptable salt or solvate thereof, and mannitol, wherein the stable pharmaceutical composition contains less than about 1 µg to about 100 µg of mannose per 100 mg of mannitol. In another embodiment, the stable pharmaceutical composition contains less than about 10 µg to about 100 µg of mannose per 100 mg of mannitol. In another embodiment, the stable pharmaceutical composition contains less than about 1 µg to about 50 µg of mannose per 100 mg of mannitol. In another embodiment, the stable pharmaceutical composition contains less than about 1 µg to about 20 µg of mannose per 100 mg of mannitol. In another embodiment, the stable pharmaceutical composition contains less than about 10 µg or less than about 5 µg of mannose per 100 mg of mannitol.

In one embodiment, provided herein are pharmaceutical compositions which are stable for at least about 5 to about 30 weeks. In another embodiment, the compositions are stable at a temperature of between about 20° C. to about 50° C. for at least about 5 to about 30 weeks. In another embodiment, the compositions are stable at a temperature of between about 20° C. to about 50° C. for at least about 5 to about 30 weeks at a relative humidity of between about 35% and about 85%.

In another embodiment, when the pharmaceutical composition comprises mannitol, the combination of excipients in the composition, absent the active ingredient, contains, or generates upon storage for from about 5 to about 30 weeks, at a temperature of between about 20° C. to about 50° C., and at a relative humidity of between about 35% and about 85% in a sealed package, less than about 0.05% mannose relative to the weight of mannitol. In another embodiment, said storage is for about 24 weeks. In another embodiment, said temperature is about 30° C. In another embodiment, said temperature is about 40° C. In another embodiment, said relative humidity is about 65%. In another embodiment, said relative humidity is about 75%. In another embodiment, the pharmaceutical composition contains or generates less than about 0.02% of mannose; or less than about 0.01% of mannose relative to the weight of mannitol.

In one embodiment, the pharmaceutical composition further comprises magnesium stearate, calcium stearate, zinc stearate or stearic acid. In one embodiment, the pharmaceutical composition further comprises at least 0.1%, 0.2%, 0.5%, 0.75%, 1%, 1.5%, 2%, 3%, or 5% by weight of magnesium stearate, calcium stearate, zinc stearate or stearic acid.

In one embodiment, the pharmaceutical composition further comprises talc, kaolin or bentonite. In one embodiment, the pharmaceutical composition further comprises at least 0.5%, 1%, 2%, 3%, 5%, 10%, 15%, 20%, 30%, or 40% by weight of talc, kaolin or bentonite.

In another embodiment, provided herein is a pharmaceutical composition comprising transnorsertraline, or a pharmaceutically acceptable salt or solvate thereof, mannitol, magnesium stearate, talc and sodium starch glycolate.

In another embodiment, provided herein is a pharmaceutical composition comprising transnorsertraline, or a pharmaceutically acceptable salt or solvate thereof, 10 to 98% by weight of mannitol, magnesium stearate, talc and sodium starch glycolate.

In another embodiment, the pharmaceutical composition comprises 50 to 98% by weight of mannitol.

In another embodiment, the pharmaceutical composition comprises 80 to 98% by weight of mannitol.

In another embodiment, the pharmaceutical composition comprises 85 to 98% by weight of mannitol.

In another embodiment, the pharmaceutical composition comprises 86 to 98% by weight of mannitol.

In one embodiment, the pharmaceutical composition is a capsule comprising transnorsertraline, or a pharmaceutically acceptable salt or solvate thereof, mannitol, talc, sodium starch glycolate and magnesium stearate in a capsule shell. The capsule may be prepared at a 0.5, 1.0 or 2.0 mg strength of transnorsertraline. The capsule may be prepared in a 100, 150, 200 or 300 mg fill weight capsule.

In another embodiment, the pharmaceutical composition is a tablet comprising transnorsertraline, or a pharmaceutically acceptable salt or solvate thereof, mannitol, talc, sodium starch glycolate and magnesium stearate. The tablet may be coated or uncoated. The tablet may be prepared at a 0.5, 1.0 or 2.0 mg strength of transnorsertraline. The tablet may be prepared as a 100, 150, 200 or 300 mg weight tablet.

In certain embodiments, the mannitol used in the preparation of the compositions provided herein is Pearlitol 160C.

In certain embodiments, the sodium starch glycolate used in the preparation of the compositions provided herein is Primojel.

Also provided herein is a method of determining the suitability of an excipient or combination of excipients for use in a transnorsertraline formulation provided herein. In one embodiment, the method comprises the determination of the level of mannose in a sample of mannitol or a mannitol-containing formulation provided herein, wherein a level of mannose in mannitol of less than or equal to about 0.1% by weight indicates suitability for use in a stable transnorsertraline formulation.

In another embodiment, a level of mannose in mannitol of less than or equal to about 0.05% by weight indicates suitability for use in a stable transnorsertraline formulation.

In another embodiment, a level of mannose in mannitol of less than or equal to about 0.02% by weight indicates suitability for use in a stable transnorsertraline formulation.

In another embodiment, a level of a level of mannose in mannitol of less than or equal to about 0.01% by weight indicates suitability for use in a stable transnorsertraline formulation.

In one embodiment, the method of determining the level of mannose in mannitol or a mannitol-containing formulation provided herein comprises the use of a HPLC (high pressure liquid chromatography) instrument. In another embodiment, the HPLC instrument comprises a corona charged aerosol detector.

In another embodiment, the method of determining the level of mannose in mannitol or a mannitol-containing formulation provided herein comprises the use of ion chromatography (IC).

Also provided herein is a salt of transnorsertraline selected from the group consisting of hydrochloride, acetate, L-malate, besylate, benzoate, tosylate, fumarate, hydrobromide, maleate, citrate, phosphate, succinate, L-tartrate, D-tartrate, S-mandelate and pyroglutamate.

In one embodiment, the salt is the hydrochloride salt. In one embodiment, the hydrochloride salt of transnorsertraline is an anhydrous solid. In another embodiment, the hydrochloride salt of transnorsertraline exists as a monohydrate.

In one embodiment, the transnorsertraline hydrochloride is (1R,4S)-transnorsertraline hydrochloride, i.e., (1R,4S)-trans-4-(3,4-dichlorophenyl)-1,2,3,4-tetrahydro-1-naphthalenamine hydrochloride. In another embodiment, the transnorsertraline hydrochloride is (1S,4R)-transnorsertraline hydrochloride, i.e., (1S,4R)-trans-4-(3,4-dichlorophenyl)-1,2,3,4-tetrahydro-1-naphthalenamine hydrochloride.

In one embodiment, the hydrochloride salt of transnorsertraline is essentially free of water.

In one embodiment, the hydrochloride salt of transnorsertraline is the crystalline anhydrate.

In one embodiment, the hydrochloride salt of transnorsertraline anhydrate has an X-ray powder diffraction pattern comprising peaks at about 14.9, 17.8, 19.2, 23.3, 24.6 and 25.2 degrees 2θ. In another embodiment, the hydrochloride salt of transnorsertraline anhydrate has an X-ray powder diffraction pattern further comprising peaks at about 5.0 and 21.8 degrees 2θ.

In one embodiment, the hydrochloride salt of transnorsertraline anhydrate has a calculated X-ray powder diffraction pattern comprising peaks at about 5.0, 15.0, 18.0, 19.5, 22.0 23.5, 24.8 and 25.4 degrees 2θ, based on data collected at about 173 K on a single crystal.

In one embodiment, the hydrochloride salt of transnorsertraline anhydrate has the following approximate unit cell dimensions:
a=16.8 Å, b=5.2 Å, c=19.1 Å, α=90.0°, β=113.1° and γ=90.0°.

In another embodiment, the hydrochloride salt of transnorsertraline anhydrate has the following approximate unit cell dimensions when measured at about 173 K:
a=16.83 Å, b=5.23 Å, c=19.06 Å, α=90.00°, β=113.10° and γ=90.00°.

In another embodiment, the approximate unit cell dimensions are:
a=16.834 Å, b=5.226 Å, c=19.059 Å, α=90.00°, β=113.10° and γ=90.00°.

In one embodiment, the hydrochloride salt of transnorsertraline anhydrate has the space group C2 (no. 5).

In one embodiment, the hydrochloride salt of transnorsertraline anhydrate has a unit cell which contains four transnorsertraline hydrochlorides (Z=4).

In one embodiment, the hydrochloride salt of transnorsertraline anhydrate has a density of about 1.4 g cm$^{-3}$.

In one embodiment, the hydrochloride salt of transnorsertraline is a monohydrate.

In another embodiment, the hydrochloride salt of transnorsertraline monohydrate is crystalline.

In one embodiment, the hydrochloride salt of transnorsertraline monohydrate has an X-ray powder diffraction pattern comprising peaks at about 12.1, 13.0, 16.8, 17.8, 20.4, 23.4, 24.2 and 27.1 degrees 2θ. In another embodiment, the hydrochloride salt of transnorsertraline monohydrate has an X-ray powder diffraction pattern which further comprising peaks at about 20.9, 21.1 and 26.2 degrees 2θ.

In one embodiment, the hydrochloride salt of transnorsertraline monohydrate has a calculated X-ray powder diffraction pattern comprising peaks at about 12.1, 13.1, 16.9, 17.9, 20.5, 21.0, 21.3, 23.6, 24.3, 26.3 and 27.2 degrees 2θ, based on data collected at about 150 K on a single crystal.

In one embodiment, the hydrochloride salt of transnorsertraline monohydrate has the following approximate unit cell dimensions:
a=7.3 Å, b=7.6 Å, c=15.3 Å, α=90.0°, β=90.1° and γ=90.0°.

In another embodiment, the hydrochloride salt of transnorsertraline monohydrate has the following approximate unit cell dimensions when measured at about 150 K:
a=7.30 Å, b=7.56 Å, c=15.29 Å, α=90.00°, β=90.09° and γ=90.00°.

In another embodiment, the approximate unit cell dimensions are:
a=7.296 Å, b=7.557 Å, c=15.287 Å, α=90.00°, β=90.09° and γ=90.00°.

In one embodiment, the hydrochloride salt of transnorsertraline monohydrate has the space group P2$_1$ (no. 4).

In one embodiment, the hydrochloride salt of transnorsertraline monohydrate has a unit cell which contains two transnorsertraline hydrochlorides (Z=2).

In one embodiment, the hydrochloride salt of transnorsertraline monohydrate has a density of about 1.4 g cm$^{-3}$.

Also provided herein is a method of treating, preventing, or managing a neurological disorder comprising administering to a patient a therapeutically or prophylactically effective amount of a transnorsertraline hydrochloride, or a pharmaceutically acceptable solvate or stereoisomer thereof.

In one embodiment, provided herein is a method of treating, preventing, or managing a neurological disorder comprising administering to a patient a composition provided herein which comprises a therapeutically or prophylactically effective amount of a transnorsertraline or a pharmaceutically acceptable salt, solvate or stereoisomer thereof.

In one embodiment, the neurological disorder is depression, cognitive deficits, fibromyalgia, pain, a sleep related disorder, chronic fatigue syndrome, attention deficit disorder (ADD), attention deficit hyperactivity disorder (ADHD), restless leg syndrome, schizophrenia, anxiety, obsessive compulsive disorder, posttraumatic stress disorder, seasonal affective disorder (SAD), premenstrual dysphoria, postmenopausal vasomotor symptoms, a neurodegenerative disease, manic conditions, dysthymic disorder, cyclothymic disorder, obesity, or substance abuse or dependency.

In one embodiment, the method comprises administering to the patient a therapeutically or prophylactically effective amount of a transnorsertraline composition provided herein as an adjunctive therapy.

In one embodiment, the method further comprises administering to the patient a therapeutically or prophylactically effective amount of one or more additional active agents.

5.1 DEFINITIONS

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "stable" refers to a compound or composition that does not readily decompose or change in chemical makeup or physical state. A stable composition or formulation provided herein does not significantly decompose under normal manufacturing or storage conditions.

As used herein, and unless otherwise indicated, the term "pharmaceutically acceptable salt" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic (e.g., L-malic), mandelic (e.g., S-mandelic), methanesulfonic, mucic, nitric, pamoic, pantothenic, phenylacetic, propionic, phosphoric, pyroglutamic, salicylic, stearic, succinic, sulfanilic, sulfuric, tartaric acid (e.g., L-tartaric acid and D-tartaric acid), p-toluenesulfonic and the like.

As used herein, and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

The terms "solid form," "solid forms" and related terms, when used herein refer to a physical form comprising transnorsertraline or a salt thereof, which is not in a liquid or a gaseous state. Solid forms may be crystalline, amorphous, partially crystalline and/or partially amorphous.

The term "crystalline" and related terms used herein, when used to describe a substance, component or product, means that the substance, component or product is substantially crystalline as determined by X-ray diffraction. See, e.g., *Remington's Pharmaceutical Sciences*, 18th ed., Mack Publishing, Easton Pa., 173 (1990); *The United States Pharmacopeia*, 23rd ed., 1843-1844 (1995).

The term "crystal forms" and related terms herein refers to the various crystalline modifications comprising a given substance, including single-component crystal forms and multiple-component crystal forms, and including, but not limited to, polymorphs, solvates, hydrates, co-crystals and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In other embodiments, a crystal form of a substance may contain about 1%, about 2%, about 3%, about 4%, about 5%, about 10%, about 15%, about 20%, about 25%, about 30%, about 35%, about 40%, about 45% or about 50% of one or more amorphous forms and/or other crystal forms on a weight and/or molar basis.

Different crystal forms may have different physical properties such as, for example, melting temperatures, heats of fusion, solubilities, dissolution rates and/or vibrational spectra as a result of the arrangement or conformation of the molecules or ions in the crystal lattice. The differences in physical properties exhibited by crystal forms affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one crystal form than when comprised of another crystal form) or mechanical changes (e.g., tablets crumble on storage as one crystal form converts into another) or both (e.g., tablets of one crystal form are more susceptible to breakdown at high humidity). As a result of solubility/dissolution differences, in the extreme case, some crystal form transitions may result in lack of potency or, at the other extreme, toxicity. In addition, the physical properties of the crystal form may be important in processing; for example, one crystal form might be more likely to form solvates or might be difficult to filter and wash free of impurities (e.g., particle shape and size distribution might be different between crystal forms).

Crystal forms of a substance can be obtained by a number of methods, as known in the art. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal countermolecules, desolvation, dehydration, rapid evaporation, rapid cooling, slow cooling, vapor diffusion, sublimation, grinding, solvent-drop grinding, microwave-induced precipitation, sonication-induced precipitation, laser-induced precipitation and precipitation from a supercritical fluid.

Techniques for characterizing crystal forms and amorphous forms include, but are not limited to, thermal gravimetric analysis (TGA), differential scanning calorimetry (DSC), X-ray powder diffractometry (XRPD), single crystal X-ray diffractometry, vibrational spectroscopy, e.g., infrared (IR) and Raman spectroscopy, solid-state nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies and dissolution studies.

The terms "polymorph," "polymorphic form" and related terms herein refer to a crystal form consisting of the same molecule, molecules and/or ions as another crystal form. The term "amorphous," "amorphous form," and related terms used herein mean that the substance, component or product in question is not substantially crystalline as determined by X-ray diffraction. In certain embodiments, an amorphous form of a substance may be substantially free of other amorphous forms and/or crystal forms. In other embodiments, an amorphous form of a substance may contain about 1%, about 2%, about 3%, about 4%, about 5%, about 10%, about 15%, about 20%, about 25%, about 30%, about 35%, about 40%, about 45% or about 50% of one or more other amorphous forms and/or crystal forms on a weight and/or molar basis. Amorphous forms of a substance can be obtained by a number of methods, as known in the art. Such methods include, but are not limited to, heating, melt cooling, rapid melt cooling, solvent evaporation, rapid solvent evaporation, desolvation, sublimation, grinding, cryo-grinding and freeze drying.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, more specifically within 10%, more specifically within 5%, of the specified dose, amount, or weight percent.

As used herein, a crystal form that is "essentially free" of water and/or solvent in the crystal lattice has a quantity of water and/or solvent in the crystal lattice which is, in certain embodiments approximately near the limit of detection, in other embodiments approximately at the limit of detection, and in other embodiments approximately below the limit of detection for solvent and/or water in the crystal lattice when measured using a conventional solid-state analytical technique, e.g., a technique described herein. In certain embodiments, the solid-state analytical technique used to determine the quantity of water and/or solvent in the crystal lattice is thermogravimetric analysis. In other embodiments, the solid-state analytical technique used to determine the quantity of water and/or solvent in the crystal lattice is Karl Fischer analysis. In other embodiments, a crystal form which is "essentially free" of water and/or solvent in the crystal lattice has a quantity of water and/or solvent which is less than about 5%, less than about 4%, less than about 3%, less than about 2%, less than about 1%, less than about 0.9%, less than about 0.8%, less than about 0.7%, less than about 0.6%, less than about 0.5%, less than about 0.4%, less than about 0.3%, less than about 0.2%, less than about 0.1%, or less than about 0.01% of the total weight of the crystal form.

As used herein, a crystalline or amorphous form that is "pure," i.e., substantially free of other crystalline or amorphous forms, contains less than about 10 percent by weight of one or more other crystalline or amorphous form, preferably less than about 5 percent by weight of one or more other crystalline or amorphous form, more preferably less than about 3 percent by weight of one or more other crystalline or amorphous form, most preferably less than about 1 percent by weight of one or more other crystalline or amorphous form.

As used herein and unless otherwise indicated, a composition that is "substantially free" of a compound means that the composition contains less than about 20 percent by weight, more preferably less than about 10 percent by weight, even more preferably less than about 5 percent by weight, and most preferably less than about 3 percent by weight of the compound.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, status epilecticus, contusive injuries (e.g., spinal cord injury and head injury), viral infection induced neurodegeneration, (e.g., AIDS, encephalopathies), epilepsy, benign forgetfulness, closed head injury, sleep disorders, depression, dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

As used herein, and unless otherwise specified, the term "affective disorder" includes depression, attention deficit disorder, attention deficit disorder with hyperactivity, bipolar and manic conditions (e.g., bipolar disorder), and the like. The terms "attention deficit disorder" (ADD) and "attention deficit disorder with hyperactivity" (ADDH), or attention deficit/hyperactivity disorder (ADHD), are used herein in accordance with the accepted meanings as found in *Diagnostic and Statistical Manual of Mental Disorders, 4$^{th}$ Ed.*, American Psychiatric Association (1997) (DSM-IV™).

As used herein, and unless otherwise specified, the term "depression" includes all forms of depression including, but not limited to, major depressive disorder (MDD), seasonal affective disorder (SAD) and dysthymia. "Major depressive disorder" is used herein interchangeably with "unipolar depression" and "major depression." "Depression" may also includes any condition commonly associated with depression, such as all forms of fatigue (e.g., chronic fatigue syndrome) and cognitive deficits.

As used herein, and unless otherwise specified, the terms "obsessive-compulsive disorder," "substance abuse," "premenstrual syndrome," "anxiety," "eating disorders" and "migraine" are used herein in a manner consistent with their accepted meanings in the art. See, e.g., DSM-IV™. For example, the term "eating disorder," as used herein, refers to abnormal compulsions to avoid eating or uncontrollable impulses to consume abnormally large amounts of food. These disorders may affect not only the social well-being, but also the physical well-being of sufferers. Examples of eating disorders include, but are not limited to, anorexia nervosa, bulimia, and binge eating.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain. See, e.g., Harrison's Principles of Internal Medicine, pp. 93-98 (Wilson et al., eds., 12th ed. 1991); Williams et al., *J. Med. Chem.* 42: 1481-1485 (1999), herein each incorporated by reference in their entirety. "Pain" is also meant to include mixed etiology pain, dual mechanism pain, allodynia, causalgia, central pain, hyperesthesia, hyperpathia, dysesthesia, and hyperalgesia. In addition, the term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes.

As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (PHN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

The embodiments provided herein can be understood more fully by reference to the following detailed description and illustrative examples, which are intended to exemplify non-limiting embodiments.

5.2 PHARMACEUTICAL COMPOSITIONS

In one embodiment, provided herein are pharmaceutical compositions comprising: transnorsertraline, or a pharmaceutically acceptable salt or solvate thereof; and a pharmaceutically acceptable carrier or excipient.

Solid dosage forms of transnorsertraline, or pharmaceutically acceptable salts or solvates thereof, are desired for ease of dosing to subjects and patients as well as providing easy to adminster formulations for out-of-clinic dosing. These dosage forms should be manufacturable on automated equipment and have acceptable chemical and physical stability that can exceed 1 year. These solid dosage forms of transnorsertraline, or pharmaceutically acceptable salts or solvates thereof are desired for development, clinical, and commercial uses.

Many excipient mixtures with transnorsertraline or a pharmaceutically acceptable salt or solvate thereof are not chemically stable. For example, hard gelatin capsules containing transnorsertraline hydrochloride in combination with the excipients found in Zoloft® (sertraline) tablets resulted in a formulation with poor chemical stability, and in particular with multiple oxidation products. These excipients are dibasic calcium phosphate dihydrate, microcrystalline cellulose, sodium starch glycolate, magnesium stearate, as well as other excipients that are likely in the coating of these tablets. See *Physician's Desk Reference* entry for Zoloft® (sertraline).

Therefore, in certain embodiments, the excipients mannitol or xylitol may be used rather than other common saccharide excipients (e.g., lactose or cellulose) in order to improve the stability of the transnorsertraline compositions provided herein. The use of saccharides other than mannitol or xylitol promotes degradation of pharmaceutical compositions comprising transnorsertraline or a pharmaceutically acceptable salt or solvate thereof.

In some embodiments, the pharmaceutical compositions provided herein comprise 10 to 98% by weight of mannitol or xylitol. In other embodiments, additional excipients used in the pharmaceutical compositions provided herein may include magnesium stearate, talc and sodium starch glycolate. Magnesium stearate, talc and sodium starch glycolate have been found to be compatible with transnorsertraline, or a pharmaceutically acceptable salts or solvates thereof, such that these excipients, in addition to mannitol and xylitol, are preferred.

Formulations comprising transnorsertraline, or a pharmaceutically acceptable salts or solvates thereof, and the excipients described above may be prepared according to the following processes.

Blends for capsules formulations containing transnorsertraline or a pharmaceutically acceptable salt or solvate thereof may be manufactured using a process in which transnorsertraline hydrochloride is first blended with talc; this mixture is then blended with mannitol in geometric dilution. The remaining mannitol and sodium starch glycolate are blended with the mixture; lastly, magnesium stearate is blended with the previous mixture. The blend may be encapsulated on a manual, semi-automatic or fully automatic capsule filling machine or device.

The process may be modified such that transnorsertraline or a pharmaceutically acceptable salt or solvate thereof is first blended with a portion of talc plus mannitol; this mixture is then blended with additional mannitol. Then the remaining mannitol and sodium starch glycolate are blended with the mixture; lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with a portion of talc plus mannitol; this mixture is then blended with a mixture of mannitol plus sodium starch glycolate; lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with a mixture of talc plus mannitol plus sodium starch glycolate; this mixture is then blended with the remaining excipients (minus the magnesium stearate). Lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with a mixture of talc plus sodium starch glycolate; this mixture is then blended with the mannitol. Lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with talc; this mixture is then blended with the mannitol. Lastly, magnesium stearate is blended with the previous mixture. The blend may be encapsulated on a manual, semi-automatic or fully automatic capsule filling machine or device.

Another modification of the process may be performed by transnorsertraline or a pharmaceutically acceptable salt or solvate thereof with a mixture of talc plus mannitol; this mixture is then blended with the remaining mannitol. Lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with mannitol; this mixture is then blended with a mixture of talc plus mannitol. Lastly, magnesium stearate is blended with the previous mixture. The blend may be encapsulated on a manual, semi-automatic or fully automatic capsule filling machine or device.

Another modification of the process may be performed by blending a portion of magnesium stearate with transnorsertraline or a pharmaceutically acceptable salt or solvate thereof in each of the above processes. Lastly, the rest of the magnesium stearate is blended with the previous mixture. The blend may be encapsulated on a manual, semi-automatic or fully automatic capsule filling machine or device.

Blends for tablet formulations containing transnorsertraline or a pharmaceutically acceptable salt or solvate thereof may be manufactured using a process in which transnorsertraline or a pharmaceutically acceptable salt or solvate thereof is first blended with talc; this mixture is then blended with mannitol in geometric dilution. Then the remaining mannitol and sodium starch glycolate are blended with the mixture; lastly, magnesium stearate is blended with the previous mixture. The blend may be compressed on a tablet press or machine.

The process for manufacturing uncoated tablets may be modified such that transnorsertraline or a pharmaceutically acceptable salt or solvate thereof is first blended with a portion of talc plus mannitol; this mixture is then blended with additional mannitol. Then the remaining mannitol and sodium starch glycolate are blended with the mixture; lastly, magnesium stearate is blended with the previous mixture. The blend may be compressed on a tablet press or machine.

Another modification of the process may be performed by blending transnorsertraline or a pharmaceutically acceptable salt or solvate thereof with a portion of talc plus mannitol; this mixture is then blended with a mixture of mannitol plus sodium starch glycolate; lastly, magnesium stearate is blended with the previous mixture. The blend may be compressed on a tablet press or machine.

Another modification of the process may be performed by blending transnorsertraline or a pharmaceutically acceptable salt or solvate thereof with a mixture of talc plus mannitol plus sodium starch glycolate; this mixture is then blended with the remaining excipients (minus the magnesium stearate). Lastly, magnesium stearate is blended with the previous mixture. The blend may be compressed on a tablet press or machine.

Another modification of the process may be performed by blending transnorsertraline or a pharmaceutically acceptable salt or solvate thereof with a mixture of talc plus sodium starch glycolate; this mixture is then blended with the mannitol. Lastly, magnesium stearate is blended with the previous mixture. The blend may be compressed on a tablet press or machine.

Another modification of the process may be performed by blending transnorsertraline or a pharmaceutically acceptable salt or solvate thereof with talc; this mixture is then blended with the mannitol. Lastly, magnesium stearate is blended with the previous mixture. The blend may be compressed on a tablet press or machine.

Another modification of the process may be performed by blending transnorsertraline or a pharmaceutically acceptable salt or solvate thereof with a mixture of talc plus mannitol; this mixture is then blended with the remaining mannitol. Lastly, magnesium stearate is blended with the previous mixture. The blend may be compressed on a tablet press or machine.

Another modification of the process may be performed by blending transnorsertraline or a pharmaceutically acceptable salt or solvate thereof with mannitol; this mixture is then blended with a mixture of talc plus mannitol. Lastly, magnesium stearate is blended with the previous mixture. The blend may be compressed on a tablet press or machine.

Another modification of the process may be performed by blending a portion of magnesium stearate with transnorsertraline or a pharmaceutically acceptable salt or solvate thereof in each of the above processes. Lastly, the rest of the magnesium stearate may be blended with the previous mixture. The blend may be compressed on a tablet press or machine.

Each of the tablets described above may also be manufactured as a coated tablet. The coating may be one of three types; these include compression coating, film-coating, or gelatin coating. The coatings each may or may not contain a coloring agent; these coloring agents may be titanium dioxide, and/or soluble colorants, such as dyes, and/or insoluble colorants such as lakes and/or colored iron oxides.

Specific formulations of transnorsertraline or a pharmaceutically acceptable salt or solvate thereof in capsule or tablet form are provided below. Formulations of other weights for capsules or tablets may also be prepared using similar or varied percentages of excipients.

A 300.0 mg capsule may be prepared using 1.125 mg of transnorsertraline hydrochloride anhydrate, 2.875 mg of talc, 275.0 mg of Pearlitol 160C (mannitol), 18.0 mg of Primojel (sodium starch glycolate), 3.0 mg of magnesium stearate and a size #1 Swedish Orange capsule shell #4188.

Alternatively, a 300.0 mg capsule may be prepared without Primojel, using 1.125 mg of transnorsertraline hydrochloride anhydrate, 2.875 mg of talc, 293.0 mg of Pearlitol 160C (mannitol), 3.0 mg of magnesium stearate and a size #1 Swedish Orange capsule shell #4188.

A 150.0 mg capsule may be prepared using 0.5625 mg of transnorsertraline hydrochloride anhydrate, 1.4375 mg of talc, 137.5 mg of Pearlitol 160C (mannitol), 9.0 mg of Primojel (sodium starch glycolate), 1.5 mg of magnesium stearate and a size 1 Swedish Orange capsule shell #4188.

Alternatively, a 150.0 mg capsule may be prepared without Primojel, using 0.5625 mg of transnorsertraline hydrochloride anhydrate, 1.4375 mg of talc, 146.5 mg of Pearlitol 160C (mannitol), 1.5 mg of magnesium stearate and a size #1 Swedish Orange capsule shell #4188.

A 300.0 mg capsule may also be prepared using 2.25 mg of transnorsertraline hydrochloride anhydrate, 4.75 mg of talc, 272.0 mg of Pearlitol 160C (mannitol), 18.0 mg of Primojel (sodium starch glycolate), 3.0 mg of magnesium stearate and a size #1 Swedish Orange capsule shell #4188.

Alternatively, the 300.0 mg capsule may be prepared without Primojel, using 2.25 mg of transnorsertraline hydrochloride anhydrate, 4.75 mg of talc, 290.0 mg of Pearlitol 160C (mannitol), 3.0 mg of magnesium stearate and a size #1 Swedish Orange capsule shell #4188.

Capsules of 100.0, 150.0 and 200.0 mg fill weights having 0.5 mg strength of transnorsertraline in various capsule shell sizes may be prepared as follows.

A 100.0 mg capsule may be prepared using 0.5625 mg of transnorsertraline hydrochloride anhydrate, 1.4375 mg of talc, 91.0 mg of mannitol, 6.0 mg of Primojel (sodium starch glycolate), 1.0 mg of magnesium stearate and a size #4 hard gelatin capsule shell.

A 150.0 mg capsule may be prepared using 0.5625 mg of transnorsertraline hydrochloride anhydrate, 1.4375 mg of talc, 137.5 mg of mannitol, 9.0 mg of Primojel (sodium starch glycolate), 1.5 mg of magnesium stearate and a size #3 hard gelatin capsule shell.

A 200.0 mg capsule may be prepared using 0.5625 mg of transnorsertraline hydrochloride anhydrate, 1.4375 mg of talc, 184.0 mg of mannitol, 12.0 mg of Primojel (sodium starch glycolate), 2.0 mg of magnesium stearate and a size #2 hard gelatin capsule shell.

Capsules of 100.0, 150.0 and 200.0 mg fill weights having 1.0 mg strength of transnorsertraline in various capsule shell sizes are prepared as follows.

A 100.0 mg capsule may be prepared using 1.125 mg of transnorsertraline hydrochloride anhydrate, 1.4375 mg of talc, 90.44 mg of mannitol, 6.0 mg of Primojel (sodium starch glycolate), 1.0 mg of magnesium stearate and a size #4 hard gelatin capsule shell.

A 150.0 mg capsule may be prepared using 1.125 mg of transnorsertraline hydrochloride anhydrate, 1.4375 mg of talc, 136.94 mg of mannitol, 9.0 mg of Primojel (sodium starch glycolate), 1.5 mg of magnesium stearate and a size #3 hard gelatin capsule shell.

A 200.0 mg capsule may be prepared using 1.125 mg of transnorsertraline hydrochloride anhydrate, 1.4375 mg of talc, 183.44 mg of mannitol, 12.0 mg of Primojel (sodium starch glycolate), 2.0 mg of magnesium stearate and a size #2 hard gelatin capsule shell.

Capsules of 100.0, 150.0 and 200.0 mg fill weights having 2.0 mg strength of transnorsertraline in various capsule shell sizes may be prepared as follows.

A 100.0 mg capsule may be prepared using 2.25 mg of transnorsertraline hydrochloride anhydrate, 4.75 mg of talc, 86.0 mg of mannitol, 6.0 mg of Primojel (sodium starch glycolate), 1.0 mg of magnesium stearate and a size #4 hard gelatin capsule shell.

A 150.0 mg capsule may be prepared using 2.25 mg of transnorsertraline hydrochloride anhydrate, 4.75 mg of talc, 132.5 mg of mannitol, 9.0 mg of Primojel (sodium starch glycolate), 1.5 mg of magnesium stearate and a size #3 hard gelatin capsule shell.

A 200.0 mg capsule may be prepared using 2.25 mg of transnorsertraline hydrochloride anhydrate, 4.75 mg of talc, 179.0 mg of mannitol, 12.0 mg of Primojel (sodium starch glycolate), 2.0 mg of magnesium stearate and a size #2 hard gelatin capsule shell.

Tablets of 100.0, 150.0 and 200.0 mg weights having 0.5 mg strength of transnorsertraline may be prepared as follows.

A 100.0 mg tablet is prepared using 0.5625 mg of transnorsertraline hydrochloride anhydrate, 1.4375 mg of talc, 91.0 mg of mannitol, 6.0 mg of Primojel (sodium starch glycolate) and 1.0 mg of magnesium stearate.

A 100.0 mg tablet may also be prepared without Primojel, using 0.5625 mg of transnorsertraline hydrochloride anhydrate, 1.4375 mg of talc, 97.0 mg of mannitol and 1.0 mg of magnesium stearate.

A 150.0 mg tablet may be prepared using 0.5625 mg of transnorsertraline hydrochloride anhydrate, 1.4375 mg of talc, 137.5 mg of mannitol, 9.0 mg of Primojel (sodium starch glycolate) and 1.5 mg of magnesium stearate.

A 150.0 mg tablet may also be prepared without Primojel, using 0.5625 mg of transnorsertraline hydrochloride anhydrate, 1.4375 mg of talc, 146.5 mg of mannitol and 1.5 mg of magnesium stearate.

A 200.0 mg tablet may be prepared using 0.5625 mg of transnorsertraline hydrochloride anhydrate, 1.4375 mg of talc, 184.0 mg of mannitol, 12.0 mg of Primojel (sodium starch glycolate) and 2.0 mg of magnesium stearate.

A 200.0 mg tablet may also be prepared without Primojel, using 0.5625 mg of transnorsertraline hydrochloride anhydrate, 1.4375 mg of talc, 196.0 mg of mannitol and 2.0 mg of magnesium stearate.

Tablets of 100.0, 150.0 and 200.0 mg weights having 1.0 mg strength of transnorsertraline may be prepared as follows.

A 100.0 mg tablet may be prepared using 1.125 mg of transnorsertraline hydrochloride anhydrate, 1.4375 mg of talc, 90.44 mg of mannitol, 6.0 mg of Primojel (sodium starch glycolate) and 1.0 mg of magnesium stearate.

A 100.0 mg tablet may also be prepared without Primojel, using 1.125 mg of transnorsertraline hydrochloride anhydrate, 1.4375 mg of talc, 96.44 mg of mannitol and 1.0 mg of magnesium stearate.

A 150.0 mg tablet may be prepared using 1.125 mg of transnorsertraline hydrochloride anhydrate, 1.4375 mg of talc, 136.94 mg of mannitol, 9.0 mg of Primojel (sodium starch glycolate) and 1.5 mg of magnesium stearate.

A 150.0 mg tablet may also be prepared without Primojel, using 1.125 mg of transnorsertraline hydrochloride anhydrate, 1.4375 mg of talc, 145.94 mg of mannitol and 1.5 mg of magnesium stearate.

A 200.0 mg tablet may be prepared using 1.125 mg of transnorsertraline hydrochloride anhydrate, 1.4375 mg of talc, 183.44 mg of mannitol, 12.0 mg of Primojel (sodium starch glycolate) and 2.0 mg of magnesium stearate.

A 200.0 mg tablet may also be prepared without Primojel, using 1.125 mg of transnorsertraline hydrochloride anhydrate, 1.4375 mg of talc, 195.44 mg of mannitol and 2.0 mg of magnesium stearate.

Tablets of 100.0, 150.0 and 200.0 mg weights having 2.0 mg strength of transnorsertraline may be prepared as follows.

A 100.0 mg tablet may be prepared using 2.25 mg of transnorsertraline hydrochloride anhydrate, 4.75 mg of talc, 86.0 mg of mannitol, 6.0 mg of Primojel (sodium starch glycolate) and 1.0 mg of magnesium stearate.

A 100.0 mg tablet may also be prepared without Primojel, using 2.25 mg of transnorsertraline hydrochloride anhydrate, 4.75 mg of talc, 92.0 mg of mannitol and 1.0 mg of magnesium stearate.

A 150.0 mg tablet may be prepared using 2.25 mg of transnorsertraline hydrochloride anhydrate, 4.75 mg of talc, 132.5 mg of mannitol, 9.0 mg of Primojel (sodium starch glycolate) and 1.5 mg of magnesium stearate.

A 150.0 mg tablet may also be prepared without Primojel, using 2.25 mg of transnorsertraline hydrochloride anhydrate, 4.75 mg of talc, 141.5 mg of mannitol and 1.5 mg of magnesium stearate.

A 200.0 mg tablet may be prepared using 2.25 mg of transnorsertraline hydrochloride anhydrate, 4.75 mg of talc, 179.0 mg of mannitol, 12.0 mg of Primojel (sodium starch glycolate) and 2.0 mg of magnesium stearate.

A 200.0 mg tablet may also be prepared without Primojel, using 2.25 mg of transnorsertraline hydrochloride anhydrate, 4.75 mg of talc, 191.0 mg of mannitol and 2.0 mg of magnesium stearate.

Capsules and tablets of other weights may be prepared using 10%-98% mannitol, 0.1%-5% magnesium stearate, 0.5%-40% talc, and 0%-10% sodium starch glycolate.

Capsules and tablets of other weights may also be prepared using 5%-99% mannitol, 0.05%-15% magnesium stearate, 0%-50% talc, and 0%-40% sodium starch glycolate.

Capsules and tablets of other weights may also be prepared using 5%-99% mannitol, 0%-15% magnesium stearate, 0.5%-50% talc, and 0%-40% sodium starch glycolate.

In some embodiments, the pharmaceutical compositions provided herein may optionally comprise one or more other active agents. Examples of suitable agents are provided herein elsewhere.

Certain pharmaceutical compositions are single unit dosage forms suitable for oral, mucosal (e.g., nasal, sublingual, vaginal, buccal, trachea, bronchial, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic or hard gelatin capsules; cachets; troches; lozenges; dispersions; suppositories; ointments; cataplasms (poultices); pastes; powders; Unit Dose Vial (UDV) nebulized solutions; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

In one embodiment, the dosage form is an oral dosage form. In another embodiment, the oral dosage form is a capsule, tablet, or syrup. In another embodiment, the dosage form is a parenteral dosage form.

The formulation should suit the mode of administration. For example, oral administration may require enteric coatings to protect the compounds administered from degradation within the gastrointestinal tract. In another example, the compounds may be administered in a liposomal formulation to shield the compounds from degradative enzymes, facilitate transport in circulatory system, and effect delivery across cell membranes to intracellular sites.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms will vary from one another will be readily apparent to those skilled in the art. See, e.g., *Remington's Pharmaceutical Sciences,* 18th ed., Mack Publishing, Easton Pa. (1990).

The selected dosage level and frequency of administration of the pharmaceutical compositions provided herein will depend upon a variety of factors including the route of administration, the time of administration, the rate of excretion of the therapeutic agents, the duration of the treatment, other drugs, compounds and/or materials used in the patient, the age, sex, weight, condition, general health and prior medical history of the patient being treated, and like factors well known in the medical arts. For example, the dosage regimen is likely to vary with pregnant women, nursing mothers and children relative to healthy adults. A physician having ordinary skill in the art can readily determine and prescribe the therapeutically effective amount of the pharmaceutical composition required.

The pharmaceutical compositions provided herein may further comprise a pharmaceutically acceptable carrier. The term "pharmaceutically acceptable carrier" means one or more pharmaceutically acceptable excipients. Examples of such excipients are well known in the art and are listed in the USP(XXI)/NF (XVI), incorporated herein in its entirety by reference thereto, and include without limitation, binders, diluents, fillers, disintegrants, super disintegrants, lubricants, surfactants, antiadherents, stabilizers, and the like. The term "additives" is synonymous with the term "excipients," as used herein.

The term "pharmaceutically acceptable" is used herein to refer to those compounds, materials, compositions and/or dosage forms which are, within the scope of sound medical judgment, suitable for administration to and for use in contact with the tissues and fluids of human beings and animals without excessive toxicity, irritation, allergic response, or other problem or complication, commensurate with a reasonable medically sound benefit/risk ratio.

Further, the term "pharmaceutically acceptable excipient" is employed to mean that there are no untoward chemical or physical incompatibilities between the active ingredients and any of the excipient components of a given dosage form. For example, an untoward chemical reaction is one wherein the potency of compounds used in methods and compositions provided herein is detrimentally reduced or increased due to the addition of one or more excipients. Another example of an untoward chemical reaction is one wherein the taste of the dosage form becomes excessively sweet, sour or the like to the extent that the dosage form becomes unpalatable. Each excipient must be "acceptable" in the sense of being compatible with the other ingredients of the formulation and not injurious to the patient.

Physical incompatibility refers to incompatibility among the various components of the dosage form and any excipient(s) thereof. For example, the combination of the excipient(s) and the active ingredient(s) may form an excessively hygroscopic mixture or an excessively segregated mixture to the degree that the desired shape of the dosage form (e.g., tablet, troche etc.), its stability or the like cannot be sufficiently maintained to be able to administer the dosage form in compliance with a prescribed dosage regimen as desired.

With the exception of capsule shells, it is noted that all excipients used in the pharmaceutical compositions or dosage forms provided herein preferably meet or exceed the standards for pharmaceutical ingredients and combinations thereof in the USP/NF. The purpose of the USP/NF is to provide authoritative standards and specifications for materials and substances and their preparations that are used in the practice of the healing arts. The USP/NF establish titles, definitions, descriptions, and standards for identity, quality, strength, purity, packaging and labeling, and also, where practicable, provide bioavailability, stability, procedures for proper handling and storage and methods for their examination and formulas for their manufacture or preparation.

The stability of a pharmaceutical product may be defined as the capability of a particular formulation, in a specific container, to remain within its physical, chemical, microbiological, therapeutic and toxicological specification, although there are exceptions, and to maintain at least about 80%, preferably about 90%, more preferably about 95% of labeled potency level. Thus, for example, expiration dating is defined as the time in which the pharmaceutical product will remain stable when stored under recommended conditions.

Many factors affect the stability of a pharmaceutical product, including the stability of the therapeutic ingredient(s), the potential interaction between therapeutic and inactive ingredients and the like. Physical factors such as heat, light and moisture may initiate or accelerate chemical reactions.

5.2.1 Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington: The Science and Practice of Pharmacy*, 20<sup>th</sup> Ed. (2000).

Typical oral dosage forms are prepared by combining the active ingredients in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Large-scale production of pharmaceutical compositions or dosage forms in accordance with the present disclosure may require, in addition to the therapeutic drug ingredients, excipients or additives including, but not limited to, diluents, binders, lubricants, disintegrants, colorants, flavors, sweetening agents and the like or mixtures thereof. By the incorporation of these and other additives, a variety of dosage forms (e.g., tablets, capsules, caplets, troches and the like) may be made. These include, for example, hard gelatin capsules, caplets, sugar-coated tablets, enteric-coated tablets to delay action, multiple compressed tablets, prolonged-action tablets, tablets for solution, effervescent tablets, buccal and sublingual tablets, troches and the like.

Hence, unit dose forms or dosage formulations of a pharmaceutical composition provided herein, such as a troche, a tablet or a capsule, may be formed by combining a desired amount of each of the active ingredients with one or more pharmaceutically compatible or acceptable excipients, as described below, in pharmaceutically compatible amounts to yield a unit dose dosage formulation the desired amount of each active ingredient. The dose form or dosage formulation may be formed by methods well known in the art.

Tablets are often a preferred dosage form because of the advantages afforded both to the patient (e.g., accuracy of dosage, compactness, portability, blandness of taste as well as ease of administration) and to the manufacturer (e.g., simplicity and economy of preparation, stability as well as convenience in packaging, shipping and dispensing). Tablets are solid pharmaceutical dosage forms containing therapeutic drug substances with or without suitable additives.

Tablets are typically made by molding, by compression or by generally accepted tablet forming methods. Accordingly, compressed tablets are usually prepared by large-scale production methods while molded tablets often involve small-scale operations. For example, there are three general methods of tablet preparation: (1) the wet-granulation method; (2) the dry-granulation method; and (3) direct compression. These methods are well known to those skilled in the art. See, *Remington: The Science and Practice of Pharmacy*, 20<sup>th</sup> Ed. (2000). See, also, *U.S. Pharmacopeia XXI*, U.S. Pharmacopeial Convention, Inc., Rockville, Md. (1985).

Various tablet formulations may be made in accordance with the methods and compositions provided herein. These include tablet dosage forms such as sugar-coated tablets, film-coated tablets, enteric-coated tablets, multiple-compressed tablets, prolonged action tablets and the like. Sugar-coated tablets (SCT) are compressed tablets containing a sugar coating. Such coatings may be colored and are beneficial in covering up drug substances possessing objectionable tastes or odors and in protecting materials sensitive to oxidation. Film-coated tablets (FCT) are compressed tablets that are covered with a thin layer or film of a water-soluble material. A number of polymeric substances with film-forming properties may be used. The film coating imparts the same general characteristics as sugar coating with the added advantage of a greatly reduced time period required for the coating operation. Enteric-coated tablets are also suitable for use in methods and compositions provided herein. Enteric-coated tablets (ECT) are compressed tablets coated with substances that resist dissolution in gastric fluid but disintegrate in the intestine. Enteric coating can be used for tablets containing drug substances that are inactivated or destroyed in the stomach, for those which irritate the mucosa or as a means of delayed release of the medication.

Multiple compressed tablets (MCT) are compressed tablets made by more than one compression cycle, such as layered tablets or press-coated tablets. Layered tablets are prepared by compressing additional tablet granulation on a previously compressed granulation. The operation may be repeated to produce multilayered tablets of two, three or more layers. Typically, special tablet presses are required to make layered tablets. See, for example, U.S. Pat. No. 5,213,738, incorporated herein in its entirety by reference thereto.

Press-coated tablets are another form of multiple compressed tablets. Such tablets, also referred to as dry-coated tablets, are prepared by feeding previously compressed tablets into a tableting machine and compressing another granulation layer around the preformed tablets. These tablets have all the advantages of compressed tablets, i.e., slotting, monogramming, speed of disintegration, etc., while retaining the attributes of sugar coated tablets in masking the taste of the drug substance in the core tablet. Press-coated tablets can also be used to separate incompatible drug substances. Further, they can be used to provide an enteric coating to the core tablets. Both types of tablets (i.e., layered tablets and press-coated tablets) may be used, for example, in the design of prolonged-action dosage forms.

Pharmaceutical compositions or unit dosage forms provided herein in the form of prolonged-action tablets may comprise compressed tablets formulated to release the drug substance in a manner to provide medication over a period of time. There are a number of tablet types that include delayed-action tablets in which the release of the drug substance is prevented for an interval of time after administration or until certain physiological conditions exist. Repeat action tablets may be formed that periodically release a complete dose of the drug substance to the gastrointestinal fluids. Also, extended release tablets that continuously release increments of the contained drug substance to the gastrointestinal fluids may be formed.

In order for medicinal substances or therapeutic ingredients provided herein, with or without excipients, to be made into solid dosage forms (e.g., tablets) with pressure, using available equipment, it is necessary that the material, either in crystalline or powdered form, possess a number of physical characteristics. These characteristics can include, for example, the ability to flow freely, as a powder to cohere upon compaction, and to be easily released from tooling. Since most materials have none or only some of these properties, methods of tablet formulation and preparation have been developed to impart these desirable characteristics to the material which is to be compressed into a tablet or similar dosage form.

As noted, in addition to the drugs or therapeutic ingredients, tablets and similar dosage forms may contain a number of materials referred to as excipients or additives. These additives are classified according to the role they play in the formulation of the dosage form such as a tablet, a caplet, a capsule, a troche or the like. One group of additives include, but are not limited to, binders, diluents (fillers), disintegrants, lubricants, and surfactants. In one embodiment the diluent, binder, disintegrant, and lubricant are not the same.

A binder is used to provide a free-flowing powder from the mix of tablet ingredients so that the material will flow when used on a tablet machine. The binder also provides a cohesiveness to the tablet. Too little binder will give flow problems and yield tablets that do not maintain their integrity, while too much can adversely affect the release (dissolution rate) of the drugs or active ingredients from the tablet. Thus, a sufficient amount of binder should be incorporated into the tablet to provide a free-flowing mix of the tablet ingredients without adversely affecting the dissolution rate of the drug ingredients from the tablet. With lower dose tablets, the need for good compressibility can be eliminated to a certain extent by the use of suitable diluting excipients called compression aids. The amount of binder used varies upon the type of formulation and mode of administration, and is readily discernible to those of ordinary skill in the art.

Binders suitable for use with dosage formulations provided herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (povidone), methyl cellulose, pre-gelatinized starch, hydroxypropyl methyl cellulose, (e.g., Nos. 2208, 2906, 2910), microcrystalline cellulose or mixtures thereof. Suitable forms of microcrystalline cellulose can include, for example, the materials sold as AVICEL PH-101, AVICEL PH-103 and AVICEL PH-105 (available from FMC Corporation, American Viscose Division, Avicel Sales, Marcus Hook, Pa., U.S.A.).

Fillers or diluents are used to give the powder (e.g., in the tablet or capsule) bulk so that an acceptable size tablet, capsule or other desirable dosage form is produced. Typically, therapeutic ingredients are formed in a convenient dosage form of suitable size by the incorporation of a diluent therewith. As with the binder, binding of the drug(s) to the filler may occur and affect bioavailability. Consequently, a sufficient amount of filler should be used to achieve a desired dilution ratio without detrimentally affecting release of the drug ingredients from the dosage form containing the filler. Further, a filler that is physically and chemically compatible with the therapeutic ingredient(s) of the dosage form should be used. The amount of filler used varies upon the type of formulation and mode of administration, and is readily discernible to those of ordinary skill in the art. Examples of fillers include, but are not limited to, lactose, glucose, sucrose, fructose, talc, calcium carbonate (e.g., granules or powder), microcrystalline cellulose, powdered cellulose, dextrates, kaolin, mannitol, xylitol, silicic acid, sorbitol, starch, pre-gelatinized starch, or mixtures thereof.

Disintegrants are used to cause the dose form (e.g., tablet) to disintegrate when exposed to an aqueous environment. Too much of a disintegrant will produce tablets which may disintegrate in the bottle due to atmospheric moisture. Too little may be insufficient for disintegration to occur and may thus alter the rate and extent of release of drug(s) or active ingredient(s) from the dosage form. Thus, a sufficient amount of disintegrant that is neither too little nor too much to detrimentally alter the release of the drug ingredients should be used to form the dosage forms provided herein. The amount of disintegrant used varies based upon the type of formulation and mode of administration, and is readily discernible to the skilled artisan. Examples of disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, or mixtures thereof.

When a dose form that dissolves fairly rapidly upon administration to the subject, e.g., in the subject's stomach is desired, a super disintegrant can be used, such as, but not limited to, croscarmellose sodium or sodium starch glycolate. The term "super disintegrant," as used herein, means a disintegrant that results in rapid disintegration of drug or active ingredient in the stomach after oral administration. Use of a super disintegrant can facilitate the rapid absorption of drug or active ingredient(s) which may result in a more rapid onset of action.

Adhesion of the dosage form ingredients to blender walls, hoppers, screens, transfer containers, and all equipment surfaces, including but not limited to punches of the manufacturing machine (e.g., a tableting machine) and dosators of the capsule manufacturing machine must be minimized or ideally avoided. Adhesion is a particular issue for the composition provided herein. For example, when drug accumulates on the punch surfaces, it causes the tablet surface to become pitted and therefore unacceptable. Also, sticking of drug or excipients in this way requires unnecessarily high ejection forces when removing the tablet from the die. Excessive ejection forces may lead to a high breakage rate and increase the cost of production not to mention excessive wear and tear on the dies. In practice, it is possible to reduce sticking by wet-massing or by the use of lubricants, e.g., magnesium stearate, and other anti-adherent excipients. However, selection of a drug salt with good anti-adhesion properties can also minimize these problems.

As noted, the lubricant is used to enhance the flow of the tableting powder mix to the tablet machine and to prevent sticking of the tablet in the die after the tablet is compressed. Too little lubricant will not permit satisfactory tablets to be made and too much may produce a tablet with a water-impervious hydrophobic coating, which can form because lubricants are usually hydrophobic materials such as stearic acid, magnesium stearate, calcium stearate and the like. Further, a water-impervious hydrophobic coating can inhibit disintegration of the tablet and dissolution of the drug ingredient(s). Thus, a sufficient amount of lubricant should be used that readily allows release of the compressed tablet from the die without forming a water-impervious hydrophobic coating that detrimentally interferes with the desired disintegration and/or dissolution of the drug ingredient(s).

Example of suitable lubricants for use with the compositions provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, or mixtures thereof. Additional lubricants include, for example, a syloid silica gel (AEROSIL 200, manufactured by W.R. Grace Co. of Baltimore Md.), a coagulated aerosol of synthetic silica (marketed by Deaussa Co. of Plano, Tex.), CAB-O-SIL (a pyrogenic silicon dioxide product sold by Cabot Co. of Boston, Mass.) or mixtures thereof.

Surfactants are used in dosage forms to improve the wetting characteristics and/or to enhance dissolution, and are particularly useful in pharmaceutical compositions or dosage forms containing poorly soluble or insoluble drug(s) or active ingredients. Examples of surfactants include, but are not limited to, polyoxyethylene sorbitan fatty acid esters, such as those commercially available as TWEENs (e.g. Tween 20 and Tween 80), polyethylene glycols, polyoxyethylene stearates, polyvinyl alcohol, polyvinylpyrrolidone, poly(oxyethylene)/poly(oxypropylene) block co-polyers such as poloxamers (e.g., commercially available as PLURONICs), and tetrafunctional block copolymers derived from sequential addition of propylene oxide and ethylene oxide to ethylenediamine, such as polyxamines (e.g., commercially as TETRONICs (BASF)), dextran, lecithin, dialkylesters of sodium sulfosuccinic acid, such as Aerosol OT, sodium lauryl sulfate, alkyl aryl polyether sulfonates or alcohols, such as TRITON X-200 or tyloxapol, p-isononylphenoxypoly (glycidol) (e.g. Olin-10G or Surfactant 10-G (Olin Chemicals), or mixtures thereof. Other pharmaceutically acceptable surfactants are well known in the art, and are described in detail in the Handbook of Pharmaceutical Excipients.

Other classes of additives for use with the pharmaceutical compositions or dosage forms provided herein include, but are not limited to, anti-caking or antiadherent agents, antimicrobial preservatives, coating agents, colorants, desiccants, flavors and perfumes, plasticizers, viscosity increasing agents, sweeteners, buffering agents, humectants and the like.

Examples of anti-caking agents include, but are not limited to, calcium silicate, magnesium silicate, silicon dioxide, colloidal silicon dioxide, talc, or mixtures thereof.

Examples of antimicrobial preservatives include, but are not limited to, benzalkonium chloride solution, benzethonium chloride, benzoic acid, benzyl alcohol, butyl paraben, cetylpyridinium chloride, chlorobutanol, cresol, dehydroacetic acid, ethylparaben, methylparaben, phenol, phenylethyl alcohol, phenylmercuric acetate, phenylmercuric nitrate, potassium sorbate, propylparaben, sodium benzoate, sodium dehydroacetate, sodium propionate, sorbic acid, thimersol, thymol, or mixtures thereof.

Examples of colorants for use with compositions provided herein include, but are not limited to, pharmaceutically acceptable dyes and lakes, caramel, red ferric oxide, yellow ferric oxide or mixtures thereof. Examples of desiccants include, but are not limited to, calcium chloride, calcium sulfate, silica gel or mixtures thereof.

Flavors that may be used include, but are not limited to, acacia, tragacanth, almond oil, anethole, anise oil, benzaldehyde, caraway, caraway oil, cardamom oil, cardamom seed, compound cardamom tincture, cherry juice, cinnamon, cinnamon oil, clove oil, cocoa, coriander oil, eriodictyon, eriodictyon fluidextract, ethyl acetate, ethyl vanillin, eucalyptus oil, fennel oil, glycyrrhiza, pure glycyrrhiza extract, glycyrrhiza fluidextract, lavender oil, lemon oil, menthol, methyl salicylate, monosodium glutamate, nutmeg oil, orange flower oil, orange flower water, orange oil, sweet orange peel tincture, compound orange spirit, peppermint, peppermint oil, peppermint spirit, pine needle oil, rose oil, stronger rose water, spearmint, spearmint oil, thymol, tolu balsam tincture, vanilla, vanilla tincture, and vanillin or mixture thereof.

Examples of sweetening agents include, but are not limited to, aspartame, dextrates, mannitol, saccharin, saccharin calcium, saccharin sodium, sorbitol, sorbitol solution, or mixtures thereof.

Exemplary plasticizers for use with the compositions provided herein include, but are not limited to, castor oil, diacetylated monoglycerides, diethyl phthalate, glycerin, mono- and di-acetylated monoglycerides, polyethylene glycol, propylene glycol, and triacetin or mixtures thereof. Suitable viscosity increasing agents include, but are not limited to, acacia, agar, alamic acid, aluminum monostearate, bentonite, bentonite magma, carbomer 934, carboxymethylcellulose calcium, carboxymethylcellulose sodium, carboxymethylcellulose sodium 12, carrageenan, cellulose, microcrystalline cellulose, gelatin, guar gum, hydroxyethyl cellulose, hydroxypropyl cellulose, hydroxypropyl methylcellulose (Nos. 2208; 2906; 2910), magnesium aluminum silicate, methylcellulose, pectin, polyvinyl alcohol, povidone, silica gel, colloidal silicon dioxide, sodium alginate, tragacanth and xanthan gum or mixtures thereof.

Buffering agents that may be used in the compositions provided herein include, but are not limited to, magnesium hydroxide, aluminum hydroxide and the like, or mixtures thereof. Examples of humectants include, but are not limited to, glycerol, other humectants or mixtures thereof.

The dosage forms provided herein may further include one or more of the following: (1) dissolution retarding agents, such as paraffin; (2) absorption accelerators, such as quaternary ammonium compounds; (3) wetting agents, such as, for example, cetyl alcohol and glycerol monostearate; (4) absorbents, such as kaolin and bentonite clay; (5) antioxidants, such as water soluble antioxidants (e.g., ascorbic acid, cysteine hydrochloride, sodium bisulfate, sodium metabisulfate, sodium sulfite and the like), oil soluble antioxidants (e.g., ascorbyl palmitate, hydroxyanisole (BHA), butylated hydroxy toluene (BHT), lecithin, propyl gallate, alpha-tocopherol and the like); and (6) metal chelating agents, such as citric acid, ethylenediamine tetracetic acid (EDTA), sorbitol, tartaric acid, phosphoric acid and the like.

Dosage forms provided herein, such as a tablet or caplet, may optionally be coated. Inert coating agents typically comprise an inert film-forming agent dispersed in a suitable solvent, and may further comprise other pharmaceutically acceptable adjuvants, such as colorants and plasticizers. Suitable inert coating agents, and methods for coating, are well known in the art, including without limitation aqueous or non-aqueous film coating techniques or microencapsulation. Examples of film-forming or coating agents include, but are not limited to, gelatin, pharmaceutical glaze, shellac, sucrose, titanium dioxide, carnauba wax, microcrystalline wax, celluloses, such as methylcellulose, hydroxymethyl cellulose, carboxymethylcellulose, cellulose acetate phthalate, hydroxypropyl methylcellulose (e.g., Nos.: 2208, 2906, 2910), hydroxypropyl cellulose, hydroxypropyl methyl cellulose phthalate (e.g., Nos.: 200731, 220824), hydroxyethylcellulose, methylhydroxyethylcellulose, ethylcellulose which may optionally be cross-linked, and sodium carboxymethyl cellulose; vinyls, such as polyvinyl pyrrolidione, polyvinyl acetate phthalate; glycols, such as polyethylene glycols; acrylics, such as dimethylaminoethyl methacrylate-methacrylate acid ester copolymer, and ethylacrylate-methylmethacrylate copolymer; and other carbohydrate polymers, such as maltodextrins, and polydextrose, or mixtures thereof. The amount of coating agent and the carrier vehicle (aqueous or non-aqueous) used varies upon the type of formulation and mode of administration, and is readily discernible to those of ordinary skill in the art.

A coating of a film forming polymer may optionally be applied to a tablet or caplet (e.g., a capsule shaped tablet) by using one of several types of equipment such as a conventional coating pan, Accelacota, High-Cola or Worster air suspension column. Such equipment typically has an exhaust-system to remove dust and solvent or water vapors to facilitate quick drying. Spray guns or other suitable atomizing equipment may be introduced into the coating pans to provide spray patterns conducive to rapid and uniform coverage of the tablet bed. Normally, heated or cold drying air is introduced over the tablet bed in a continuous or alternate fashion with a spray cycle to expedite drying of the film coating solution.

The coating solution may be sprayed by using positive pneumatic displacement or peristaltic pump systems in a continuous or intermittent spray-dry cycle. The particular type of spray application is selected depending upon the drying efficiency of the coating pan. In most cases, the coating material is sprayed until the tablets are uniformly coated to the desired thickness and the desired appearance of the tablet is achieved. Many different types of coatings may be applied such as enteric, slow release coatings or rapidly dissolving type coatings for fast acting tablets. Preferably, rapidly dissolving type coatings are used to permit more rapid release of the active ingredients, resulting in hastened onset. The thickness of the coating of the film forming polymer applied to a tablet, for example, may vary. However, it is preferred that the thickness simulate the appearance, feel (tactile and mouth feel) and function of a gelatin capsule. Where more rapid or delayed release of the therapeutic agent(s) is desired, one skilled in the art would easily recognize the film type and thickness, if any, to use based on characteristics such as desired blood levels of active ingredient, rate of release, solubility of active ingredient, and desired performance of the dosage form.

A number of suitable film forming agents for use in coating a final dosage form, such as tablets include, for example, methylcellulose, hydroxypropyl methyl cellulose (PHARMACOAT 606 6 cps), polyvinylpyrrolidone (povidone), ethylcellulose (ETHOCEL 10 cps), various derivatives of methacrylic acids and methacrylic acid esters, cellulose acetate phthalate or mixtures thereof.

The method of preparation and the excipients or additives to be incorporated into dosage form (such as a tablet or caplet) are selected in order to give the tablet formulation the desirable physical characteristics while allowing for ease of manufacture (e.g., the rapid compression of tablets). After manufacture, the dose form preferably should have a number of additional attributes, for example, for tablets, such attributes include appearance, hardness, disintegration ability and uniformity, which are influenced both by the method of preparation and by the additives present in the tablet formulation.

Further, it is noted that tablets or other dosage forms of the pharmaceutical compositions provided herein should retain their original size, shape, weight and color under normal handling and storage conditions throughout their shelf life. Thus, for example, excessive powder or solid particles at the bottom of the container, cracks or chips on the face of a tablet, or appearance of crystals on the surface of tablets or on container walls are indicative of physical instability of uncoated tablets. Hence, the effect of mild, uniform and reproducible shaking and tumbling of tablets should be undertaken to insure that the tablets have sufficient physical stability. Tablet hardness can be determined by commercially available hardness testers. In addition, the in vitro availability of the active ingredients should not change appreciably with time.

The tablets, and other dosage forms of the pharmaceutical compositions provided herein, such as dragees, capsules, pills and granules, may optionally be scored or prepared with coatings and shells, such as enteric coatings and other coatings well known in the pharmaceutical formulating art.

5.2.2 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients (i.e., the compounds used in methods and compositions provided herein) disclosed herein can also be incorporated into the parenteral dosage forms.

5.2.3 Transdermal, Topical and Mucosal Dosage Forms

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 &

1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients provided herein. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts or solvates (e.g., hydrates) of the active ingredients can be used to further adjust the properties of the resulting composition.

5.2.4 Compositions with Enhanced Stability

The suitability of a particular excipient may also depend on the specific active ingredients in the dosage form. For example, the decomposition of an active ingredient, e.g., transnorsertraline or a pharmaceutically acceptable salt or solvate thereof, may be accelerated by certain excipients. Certain saccharides, particularly mono- or di-saccharides, may accelerate the decomposition of the active ingredient of a composition provided herein. For example, compositions comprising transnorsertraline or a pharmaceutically acceptable salt or solvate thereof should contain little, if any, lactose, mannose, xylose, or microcrystalline cellulose.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms provided herein may be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Specific non-limiting examples of stable pharmaceutical compositions are provided herein in Examples 6.1 to 6.13.

Like the amounts and types of excipients, the amounts and specific types of active ingredients in a dosage form may differ depending on factors such as, but not limited to, the route by which it is to be administered to patients.

5.2.5 Delayed Release Dosage Forms

Active ingredients used in methods and compositions provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds used in methods and compositions provided herein. Thus, provided herein are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.2.6 Kits

In some cases, active ingredients used in methods and compositions provided herein are preferably not administered to a patient at the same time or by the same route of administration. Therefore, provided are kits which, when used by the medical practitioner, can simplify the administration of appropriate amounts of active ingredients to a patient.

In one embodiment, the kit comprises a single unit dosage form of the compounds used in methods and composition provided herein, or a pharmaceutically acceptable salt, solvate, or stereoisomer thereof, and a single unit dosage form of another agent that may be used in combination with those compounds. Kits provided herein can further comprise devices that are used to administer the active ingredients. Examples of such devices include, but are not limited to, syringes, drip bags, patches, and inhalers.

Kits provided herein can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Certain embodiments are exemplified in the following non-limiting examples. It will be apparent to those skilled in the art that many modifications, both to materials and methods, can be practiced without departing from the spirit and scope of this disclosure.

5.3 METHODS OF TREATMENT, PREVENTION AND MANAGEMENT

In one embodiment, provided herein is a method of treating, preventing, or managing a central nervous system disorder comprising administering to a subject (e.g., patient) a therapeutically or prophylactically effective amount of a formulation of salt or polymorph of transnorsertraline as disclosed herein.

In one embodiment, provided herein is a method of effecting an anti-depressant-like effect. The method comprises administering to a subject a therapeutically effective amount of a formulation, salt or polymorph of transnorsertraline as disclosed herein. Anti-depressant-like effects may be measured using an animal model of disease, such as those known in the art and those described herein.

In other embodiments, the neurological disorder is: depression (e.g., major depressive disorder, bipolar depression, unipolar disorder, dysthymia and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; obesity; and substance abuse or dependency (e.g., cocaine addiction, nicotine addiction). In another embodiment, the compounds provided herein are useful to treat two or more conditions/disorders, which are comorbid, such as cognitive deficit and depression.

In certain embodiments, neurological disorders include cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods and/or compositions provided herein include, but are not limited to: obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In one embodiment, the neurological disorder is depression. In another embodiment, the neurological disorder is anxiety disorder. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the neurological disorder is incontinence, for example, urinary incontinence. In another embodiment, the neurological disorder is sexual dysfunction.

In one embodiment, the neurological disorder is obesity, and the therapeutically effective amount of compound to supply to a patient is sufficient so that said patient feels satiated.

In one embodiment, the compounds described herein treat, prevent, and/or manage a central nervous disorder, without causing addiction to said compounds.

In some embodiments, the methods provided herein may optionally comprise the administration of one or more of other active agents. Such other agents include, but are not limited to, those drugs or therapies conventionally used for the treatment, prevention, and/or management of neurological disorders provided herein.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a subject (e.g., patient) to treat, prevent, and/or manage the disorders described herein will depend upon a variety of factors including the activity of the particular compound employed, the route of administration, the time of administration, the rate of excretion or metabolism of the particular compound being employed, the duration of the treatment, other drugs, compounds and/or materials used in combination with the particular compound employed, the age, sex, weight, condition, general health, and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 0.05 mg to about 5 g per day. In one embodiment, the oral dose of a compound provided herein will range from about 0.1 mg to about 3 g per day. In one embodiment, the oral dose of a compound provided herein will range from about 0.25 mg to about 2 g per day. In one embodiment, the oral dose of a compound provided herein will range from about 0.5 mg to about 1 g per day. In one embodiment, the oral dose of a compound provided herein will range from about 1 mg to about 500 mg per day. In another embodiment, the oral dose of a compound provided herein will range from about 2 mg to about 250 mg per day. In another embodiment, the oral dose of a compound provided herein will range from about 3 mg to about 300 mg per day. In one embodiment, the oral dose of a compound provided herein will range from about 5 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 30 mg to about 200 mg per day. Each of the above-recited dosage ranges may be formulated as a single or multiple unit dosage formulations.

6. EXAMPLES

6.1 Stable Formulations of Transnorsertraline

Solid dosage forms of transnorsertraline, or pharmaceutically acceptable salts or solvates thereof, are desired for ease of dosing to subjects and patients as well as providing easy to administer formulations for out-of-clinic dosing. These dosage forms should be manufacturable on automated equipment and have acceptable chemical and physical stability that can exceed 1 year.

Multiple excipient mixtures with transnorsertraline or a pharmaceutically acceptable salt or solvate thereof were prepared and evaluated for chemical stability and manufacturing feasibility. These excipients included several diluents: dibasic calcium phosphate anhydrous, dibasic calcium phosphate dihydrate, pregelatinized starch, microcrystalline cellulose, lactose, and mannitol; disintegrants: croscarmellose sodium, pregelatinized starch, and sodium starch glycolate; glidants: talc, colloidal silica, and fumed silica; and several lubricants: stearic acid, sodium stearyl fumarate, hydrogenated vegetable oil and magnesium stearate. Most combinations were unacceptable due to poor chemical stability; some combinations were also unacceptable due to poor manufacturing attributes, including poor blend homogeneity, low drug content in capsules, and variable drug content in capsules.

For example, when hard gelatin capsules were formulated, it was found that the combination of transnorsertraline hydrochloride with the excipients found in Zoloft® (sertraline) tablets resulted in a formulation with poor chemical stability, and in particular with multiple oxidation products. These excipients are dibasic calcium phosphate dihydrate, microcrystalline cellulose, sodium starch glycolate, magnesium stearate, as well as other excipients that are likely in the coating of these tablets. See *Physician's Desk Reference* entry for Zoloft® (sertraline).

Additionally, most of the combinations tested using the above excipients were unacceptable due to poor chemical stability. Some combinations were also unacceptable due to poor manufacturing attributes, including poor blend homogeneity, low drug content in capsule and variable drug content in capsules. Stable combinations included mannitol, sodium starch glycolate, talc, and magnesium stearate in a clear or colored hard gelatin capsule shell.

Stability Study Results

The following blends or blends-in-capsules were prepared while developing a stable transnorsertraline hydrochloride capsule formulation. In some cases, the length of testing varies. However, uniform analytical methods were used for all samples. Degradation is reported as total impurities based on an Area % from HPLC analysis of the formulations, as is common when reporting such results when a change is prior to a complete characterization of the degradation. Percent degradation was measured after storage at 40° C./75% relative humidity, a typical and required storage condition.

TABLE 1

Stability of Transnorsertraline HCl Excipient Blends

| Blend: | TNS HCl A[1] A-Tab[2] Starch 1500[5] | TNS HCl A[1] PRUV[3] | TNS HCl A[1] Stearic Acid | TNS HCl A[1] Di-Tab[4] MCC[6] AcDiSol[7] Talc | TNS HCl A[1] Di-Tab[4] MCC[6] | TNS HCl A[1] mannitol Citric acid | TNS HCl M[9] mannitol | TNS HCl M[9] A-Tab[2] |
|---|---|---|---|---|---|---|---|---|
| % Deg.[8]: | 0.93% | 1.12% | 0.39% | 1.49% | 0.88% | 0.26% | 0.20% | 0.40% |
| Time: | 5 weeks | 2 weeks | 4 weeks | 5 weeks | 5 weeks | 2 weeks | 5 weeks | 5 weeks |

[1]transnorsertraline hydrochloride anhydrate.
[2]dibasic calcium phosphate, anhydrous.
[3]sodium stearyl fumarate.
[4]dibasic calcium phosphate dihydrate.
[5]pregelatinized starch.
[6]microcrystalline cellulose.
[7]croscarmellose sodium
[8]% degradation when stored at 40° C./75% relative humidity.
[9]transnorsertraline hydrochloride monohydrate.

As a result of the stability study, the following formulation was selected. Capsule formulations of transnorsertraline hydrochloride were prepared at 1.0 mg strength (based on the free base) per capsule. The capsule formulations include mannitol, sodium starch glycolate, talc and magnesium stearate in a colored hard gelatin capsule shell:

6.2 1.0 mg Strength Capsule Formulations of Transnorsertraline Hydrochloride Anhydrate

| Ingredient | Form. 1 | Form. 2 |
|---|---|---|
| Transnorsertraline HCl Anhydrate | 1.125 mg | 1.125 mg |
| Talc | 2.875 mg | 2.875 mg |
| Pearlitol 160C (mannitol) | 275.0 mg | 293.0 mg |
| Sodium starch glycolate (Primojel) | 18.0 mg | — |
| Magnesium stearate | 3.0 mg | 3.0 mg |
| TOTAL | 300.0 mg | 300.0 mg |
| Size #1 Swedish Orange capsule shell # 4188 | 1 each | 1 each |

Stable 1.0 mg strength (based on free base) capsules of transnorsertraline hydrochloride anhydrate (1.125 mg of HCl salt) were prepared according to formulation 1. The formulation was initially prepared by hand, showing acceptable blend and capsule homogeneity; a stability study showed improved chemical stability of these capsules compared to other formulations. Manufacturing feasibility was demonstrated when a batch according to formulation 1 was manufactured on typical pharmaceutical equipment; acceptable blend and capsule homogeneity, as well as improved chemical stability was shown for this batch.

Manufacturing feasibility was demonstrated on a larger blend size when a batch according to formulation 1 was manufactured on typical pharmaceutical equipment; acceptable blend and capsule homogeneity, as well as improved chemical stability have been shown for this batch. Another capsule may be prepared according to formulation 2, wherein no sodium starch glycolate is present.

6.3 0.5 mg Strength Capsule Formulations of Transnorsertraline Hydrochloride Anhydrate

| Ingredient | Form. 1 | Form. 2 |
|---|---|---|
| Transnorsertraline HCl Anhydrate | 0.5625 mg | 0.5625 mg |
| Talc | 1.4375 mg | 1.4375 mg |
| Pearlitol 160C (mannitol) | 137.5 mg | 146.5 mg |
| Sodium starch glycolate (Primojel) | 9.0 mg | — |
| Magnesium stearate | 1.5 mg | 1.5 mg |
| TOTAL | 150.0 mg | 150.0 mg |
| Size #1 Swedish Orange capsule shell # 4188 | 1 each | 1 each |

Stable 0.5 mg strength (based on free base) capsules of transnorsertraline hydrochloride anhydrate (0.5625 mg of HCl salt) were prepared according to formulation 1. Manufacturing feasibility was demonstrated on a large blend size when a batch of formulation 1 was manufactured on typical pharmaceutical equipment; acceptable blend and capsule homogeneity, as well as improved chemical stability have been shown for this batch. Another capsule may be prepared according to formulation 2, wherein no sodium starch glycolate is present.

6.4 2.0 mg Strength Capsule Formulations of Transnorsertraline Hydrochloride Anhydrate

| Ingredient | Form. 1 | Form. 2 |
|---|---|---|
| Transnorsertraline HCl Anhydrate | 2.25 mg | 2.25 mg |
| Talc | 4.75 mg | 4.75 mg |
| Pearlitol 160C (mannitol) | 272.0 mg | 290.0 mg |
| Sodium starch glycolate (Primojel) | 18.0 mg | — |
| Magnesium stearate | 3.0 mg | 3.0 mg |
| TOTAL | 300.0 mg | 300.0 mg |
| Size #1 Swedish Orange capsule shell # 4188 | 1 each | 1 each |

Stable 2.0 mg strength (based on free base) capsules of transnorsertraline hydrochloride anhydrate (2.25 mg of HCl salt) were prepared according to formulation 1. Manufacturing feasibility was demonstrated on a large blend size when a batch of formulation 1 was manufactured on typical pharmaceutical equipment; acceptable blend and capsule homogeneity, as well as improved chemical stability have been shown for this batch. Another capsule may be prepared according to formulation 2, wherein no sodium starch glycolate is present.

6.5 0.5 mg Strength Capsule Formulations of Transnorsertraline Hydrochloride Anhydrate in Various Capsule Sizes

| Ingredient | Size # 2 | Size # 3 | Size # 4 |
|---|---|---|---|
| Transnorsertraline HCl Anhydrate | 0.5625 mg | 0.5625 mg | 0.5625 mg |
| Talc | 1.4375 mg | 1.4375 mg | 1.4375 mg |
| Mannitol | 184.0 mg | 137.5 mg | 91.0 mg |
| Sodium starch glycolate (Primojel) | 12.0 mg | 9.0 mg | 6.0 mg |
| Magnesium stearate | 2.0 mg | 1.5 mg | 1.0 mg |
| TOTAL | 200.0 mg | 150.0 mg | 100.0 mg |
| Size #2 hard gelatin capsule shell | 1 each | — | — |
| Size #3 hard gelatin capsule shell | — | 1 each | — |
| Size #4 hard gelatin capsule shell | — | — | 1 each |

Representative 0.5 mg strength (based on free base) capsules of transnorsertraline hydrochloride anhydrate (0.5625 mg) may be prepared in three fill weights of 200.0 mg, 150.0 mg and 100.0 mg for capsules of various sizes as shown above.

6.6 1.0 mg Strength Capsule Formulations of Transnorsertraline Hydrochloride Anhydrate in Various Capsule Sizes

| Ingredient | Size # 2 | Size # 3 | Size # 4 |
|---|---|---|---|
| Transnorsertraline HCl Anhydrate | 1.125 mg | 1.125 mg | 1.125 mg |
| Talc | 1.4375 mg | 1.4375 mg | 1.4375 mg |
| Mannitol | 183.44 mg | 136.94 mg | 90.44 mg |
| Sodium starch glycolate (Primojel) | 12.0 mg | 9.0 mg | 6.0 mg |
| Magnesium stearate | 2.0 mg | 1.5 mg | 1.0 mg |
| TOTAL | 200.0 mg | 150.0 mg | 100.0 mg |
| Size #2 hard gelatin capsule shell | 1 each | — | — |
| Size #3 hard gelatin capsule shell | — | 1 each | — |
| Size #4 hard gelatin capsule shell | — | — | 1 each |

Representative 1.0 mg strength (based on free base) capsules of transnorsertraline hydrochloride anhydrate (1.125 mg of HCl salt) may be prepared in three fill weights of 200.0 mg, 150.0 mg and 100.0 mg for capsules of various sizes as shown above.

6.7 2.0 mg Strength Capsule Formulations of Transnorsertraline Hydrochloride Anhydrate in Various Capsule Sizes

| Ingredient | Size # 2 | Size # 3 | Size # 4 |
|---|---|---|---|
| Transnorsertraline HCl Anhydrate | 2.25 mg | 2.25 mg | 2.25 mg |
| Talc | 4.75 mg | 4.75 mg | 4.75 mg |
| Mannitol | 179.0 mg | 132.5 mg | 86.0 mg |
| Sodium starch glycolate (Primojel) | 12.0 mg | 9.0 mg | 6.0 mg |
| Magnesium stearate | 2.0 mg | 1.5 mg | 1.0 mg |
| TOTAL | 200.0 mg | 150.0 mg | 100.0 mg |
| Size #2 hard gelatin capsule shell | 1 each | — | — |
| Size #3 hard gelatin capsule shell | — | 1 each | — |
| Size #4 hard gelatin capsule shell | — | — | 1 each |

Representative 2.0 mg strength (based on free base) capsules of transnorsertraline hydrochloride anhydrate (2.25 mg of HCl salt) may be prepared in three fill weights of 200.0 mg, 150.0 mg and 100.0 mg for capsules of various sizes as shown above.

In above examples, if transnorsertraline hydrochloride monohydrate is used in place of transnorsertraline hydrochloride anhydrate, a conversion factor of 1.186 mg of transnorsertraline hydrochloride monohydrate equivalent to 1.0 mg transnorsertraline free base can be applied to each formulation.

6.8 Manufacturing Processes for Capsule Formulations of Transnorsertraline

Blends for capsules formulations containing transnorsertraline or a pharmaceutically acceptable salt or solvate thereof may be manufactured using a process in which transnorsertraline hydrochloride is first blended with talc; this mixture is then blended with mannitol in geometric dilution. The remaining mannitol and sodium starch glycolate are blended with the mixture; lastly, magnesium stearate is blended with the previous mixture. The blend may be encapsulated on a manual, semi-automatic or fully automatic capsule filling machine or device.

The process may be modified such that transnorsertraline or a pharmaceutically acceptable salt or solvate thereof is first blended with a portion of talc plus mannitol; this mixture is then blended with additional mannitol. Then the remaining mannitol and sodium starch glycolate are blended with the mixture; lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with a portion of talc plus mannitol; this mixture is then blended with a mixture of mannitol plus sodium starch glycolate; lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with a mixture of talc plus mannitol plus sodium starch glycolate; this mixture is then blended with the remaining excipients (minus the magnesium stearate). Lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with a mixture of talc plus sodium starch glycolate; this mixture is then blended with the mannitol. Lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with talc; this mixture is then blended with the mannitol. Lastly, magnesium stearate is blended with the previous mixture. The blend may be encapsulated on a manual, semi-automatic or fully automatic capsule filling machine or device.

Another modification of the process may be performed by transnorsertraline or a pharmaceutically acceptable salt or solvate thereof with a mixture of talc plus mannitol; this mixture is then blended with the remaining mannitol. Lastly, magnesium stearate is blended with the previous mixture. The blend may be encapsulated on a manual, semi-automatic or fully automatic capsule filling machine or device.

Another modification of the process may be performed by blending transnorsertraline or a pharmaceutically acceptable salt or solvate thereof with mannitol; this mixture is then blended with a mixture of talc plus mannitol. Lastly, magnesium stearate is blended with the previous mixture. The blend may be encapsulated on a manual, semi-automatic or fully automatic capsule filling machine or device.

Another modification of the process may be performed by blending a portion of magnesium stearate with transnorsertraline or a pharmaceutically acceptable salt or solvate thereof in each of the above processes. Lastly, the rest of the magnesium stearate is blended with the previous mixture. The blend may be encapsulated on a manual, semi-automatic or fully automatic capsule filling machine or device.

6.9 0.5 mg Strength Tablet Formulations of Transnorsertraline Hydrochloride Anhydrate of Various Tablet Sizes

| Ingredient | Tablet size #1 | Tablet size #2 | Tablet size #3 |
|---|---|---|---|
| Transnorsertraline HCl Anhydrate | 0.5625 mg | 0.5625 mg | 0.5625 mg |
| Talc | 1.4375 mg | 1.4375 mg | 1.4375 mg |
| Mannitol | 184.0 mg | 137.5 mg | 91.0 mg |
| Sodium starch glycolate (Primojel) | 12.0 mg | 9.0 mg | 6.0 mg |
| Magnesium stearate | 2.0 mg | 1.5 mg | 1.0 mg |
| TOTAL | 200.0 mg | 150.0 mg | 100.0 mg |
| Transnorsertraline HCl Anhydrate | 0.5625 mg | 0.5625 mg | 0.5625 mg |
| Talc | 1.4375 mg | 1.4375 mg | 1.4375 mg |
| Mannitol | 196.0 mg | 146.5 mg | 97.0 mg |
| Magnesium stearate | 2.0 mg | 1.5 mg | 1.0 mg |
| TOTAL | 200.0 mg | 150.0 mg | 100.0 mg |

Representative 0.5 mg strength (based on free base) tablets of transnorsertraline hydrochloride anhydrate (0.5625 mg of HCl salt) may be prepared in three sizes as shown above, with or without the use of sodium starch glycolate (Primojel).

6.10 1.0 mg Strength Tablet Formulations of Transnorsertraline Hydrochloride Anhydrate of Various Tablet Sizes

| Ingredient | Tablet size #1 | Tablet size #2 | Tablet size #3 |
|---|---|---|---|
| Transnorsertraline HCl Anhydrate | 1.125 mg | 1.125 mg | 1.125 mg |
| Talc | 1.4375 mg | 1.4375 mg | 1.4375 mg |
| Mannitol | 183.44 mg | 136.94 mg | 90.44 mg |
| Sodium starch glycolate (Primojel) | 12.0 mg | 9.0 mg | 6.0 mg |
| Magnesium stearate | 2.0 mg | 1.5 mg | 1.0 mg |
| TOTAL | 200.0 mg | 150.0 mg | 100.0 mg |
| Transnorsertraline HCl Anhydrate | 1.125 mg | 1.125 mg | 1.125 mg |
| Talc | 1.4375 mg | 1.4375 mg | 1.4375 mg |
| Mannitol | 195.44 mg | 145.94 mg | 96.44 mg |
| Magnesium stearate | 2.0 mg | 1.5 mg | 1.0 mg |
| TOTAL | 200.0 mg | 150.0 mg | 100.0 mg |

Representative 1.0 mg strength (based on free base) tablets of transnorsertraline hydrochloride anhydrate (1.125 mg of HCl salt) may be prepared in three sizes as shown above, with or without the use of sodium starch glycolate (Primojel).

6.11 2.0 mg Strength Tablet Formulations of Transnorsertraline Hydrochloride Anhydrate of Various Tablet Sizes

| Ingredient | Tablet size #1 | Tablet size #2 | Tablet size #3 |
|---|---|---|---|
| Transnorsertraline HCl Anhydrate | 2.25 mg | 2.25 mg | 2.25 mg |
| Talc | 4.75 mg | 4.75 mg | 4.75 mg |
| Mannitol | 179.0 mg | 132.5 mg | 86.0 mg |
| Sodium starch glycolate (Primojel) | 12.0 mg | 9.0 mg | 6.0 mg |
| Magnesium stearate | 2.0 mg | 1.5 mg | 1.0 mg |
| TOTAL | 200.0 mg | 150.0 mg | 100.0 mg |
| Transnorsertraline HCl Anhydrate | 2.25 mg | 2.25 mg | 2.25 mg |
| Talc | 4.75 mg | 4.75 mg | 4.75 mg |
| Mannitol | 191.0 mg | 141.5 mg | 92.0 mg |
| Magnesium stearate | 2.0 mg | 1.5 mg | 1.0 mg |
| TOTAL | 200.0 mg | 150.0 mg | 100.0 mg |

Representative 2.0 mg strength (based on free base) tablets of transnorsertraline hydrochloride anhydrate (2.25 mg of HCl salt) may be prepared in three sizes as shown above, with or without the use of sodium starch glycolate (Primojel).

In above examples, if transnorsertraline hydrochloride monohydrate is used in place of transnorsertraline hydrochloride anhydrate, a conversion factor of 1.186 mg of transnorsertraline hydrochloride monohydrate equivalent to 1.0 mg transnorsertraline free base can be applied.

6.12 Manufacturing Processes for Uncoated Tablet Formulations of Transnorsertraline Blends for tablet formulations containing transnorsertraline or a pharmaceutically acceptable salt or solvate thereof may be manufactured using a process in which transnorsertraline or a pharmaceutically acceptable salt or solvate thereof is first blended with talc; this mixture is then blended with mannitol in geometric dilution. Then the remaining mannitol and sodium starch glycolate are blended with the mixture; lastly, magnesium stearate is blended with the previous mixture. The blend may be compressed on a tablet press or machine.

The process for manufacturing uncoated tablets may be modified such that transnorsertraline or a pharmaceutically acceptable salt or solvate thereof is first blended with a portion of talc plus mannitol; this mixture is then blended with additional mannitol. Then the remaining mannitol and sodium starch glycolate are blended with the mixture; lastly, magnesium stearate is blended with the previous mixture. The blend may be compressed on a tablet press or machine.

Another modification of the process may be performed by blending transnorsertraline or a pharmaceutically acceptable salt or solvate thereof with a portion of talc plus mannitol; this mixture is then blended with a mixture of mannitol plus sodium starch glycolate; lastly, magnesium stearate is blended with the previous mixture. The blend may be compressed on a tablet press or machine.

Another modification of the process may be performed by blending transnorsertraline or a pharmaceutically acceptable salt or solvate thereof with a mixture of talc plus mannitol plus sodium starch glycolate; this mixture is then blended with the remaining excipients (minus the magnesium stearate). Lastly, magnesium stearate is blended with the previous mixture. The blend may be compressed on a tablet press or machine.

Another modification of the process may be performed by blending transnorsertraline or a pharmaceutically acceptable salt or solvate thereof with a mixture of talc plus sodium starch glycolate; this mixture is then blended with the mannitol. Lastly, magnesium stearate is blended with the previous mixture. The blend may be compressed on a tablet press or machine.

Another modification of the process may be performed by blending transnorsertraline or a pharmaceutically acceptable salt or solvate thereof with talc; this mixture is then blended with the mannitol. Lastly, magnesium stearate is blended with the previous mixture. The blend is compressed on a tablet press or machine.

Another modification of the process may be performed by blending transnorsertraline or a pharmaceutically acceptable salt or solvate thereof with a mixture of talc plus mannitol; this mixture is then blended with the remaining mannitol. Lastly, magnesium stearate is blended with the previous mixture. The blend may be compressed on a tablet press or machine.

Another modification of the process may be performed by blending transnorsertraline or a pharmaceutically acceptable salt or solvate thereof with mannitol; this mixture is then blended with a mixture of talc plus mannitol. Lastly, magnesium stearate is blended with the previous mixture. The blend may be compressed on a tablet press or machine.

Another modification of the process may be performed by blending a portion of magnesium stearate with transnorsertraline or a pharmaceutically acceptable salt or solvate thereof in each of the above processes. Lastly, the rest of the magnesium stearate is blended with the previous mixture. The blend may be compressed on a tablet press or machine.

6.13 Manufacturing Processes for Coated Tablets of Transnorsertraline

Each of the tablets described above may also be manufactured as a coated tablet. The coating may be one of three types; these include compression coating, film-coating, or gelatin coating. The coatings each may or may not contain a coloring agent; these coloring agents may be titanium dioxide, and/or soluble colorants, such as dyes, and/or insoluble colorants such as lakes and/or colored iron oxides.

6.14 Solid Forms of Transnorsertraline Salts

Sixteen salts of transnorsertraline were investigated using polarized light microscopy (PSM) in order to identify salts of transnorsertraline in crystalline form: hydrochloride, citrate, fumarate, maleate, phosphate, succinate, sulfate, L-tartrate, besylate, tosylate, L-malate, S-mandelate, acetate, benzoate, hydrobromide and pyroglutamate.

Samples were observed using the Nikon Microphot polarizing light microscope. Samples were prepared in Cargille liquid with a refractive index of 1.600. Samples were observed using cross-polarized light and imaged using cross-polarized light with a quarter wave plate. Initial determination of crystallinity of transnorsertraline salts was performed by direct observation under cross-polarized light (Table 2). Any salt tested that contained solid material lacking birefringence when observed under cross-polarized light, indicating amorphous or partially amorphous solids, was rejected.

TABLE 2

PLM Observations for Transnorsertraline Salts

| Salt | Crystallinity | Crystal Habit/Description |
|---|---|---|
| HCl | Yes | Long Needles |
| Citrate | Yes | Rods and Needles |
| Fumarate | Yes | Small Needles |
| Maleate | Yes | Small Plates |
| Phosphate | Yes | Agglomerated Fines |
| Succinate | Partial | Large Plates and Amorphous Solids |
| Sulfate | Yes | Agglomerated Fines |
| L-tartrate | Yes | Large Plates |
| Besylate | Yes | Large Rods |
| Tosylate | Yes | Needles |
| L-malate | Yes | Very Small Plates, Agglomerates |
| S-mandelate | Yes | Large Rods |
| Acetate | Yes | Large Thin Plates |
| Benzoate | Yes | Thick Rods |
| HBr (18) | Yes | Fine Needles |
| Pyroglutamate | Yes | Large Plates and Very Small Plates |

"Fine or Fines" are defined in this report as particles having widths <10 μm

Each salt, with the exception of the succinate salt, exhibited good birefringence under cross-polarized light, indicating a crystalline solid. Crystal habits ranged from fine needles to large plates (Table 2).

6.15 Thermal Properties of Transnorsertraline Salts

Each of the salts of transnorsertraline of Example 6.14 were analyzed using direct scanning calorimetry (DSC) or hotstage. All DSC analyses were performed using Perkin Elmer DSC 7 Differential Scanning calorimeter. Each sample was analyzed in a crimped pan with a pinhole, heated under a nitrogen purge at a rate of 10° C./min, from a starting temperature of 25° C. up to a final temperature of 325° C. Hotstage samples were analyzed using the Nikon Microphot Polarized Light Microscope equipped with a Linkam Hotstage THMS 600. Each sample was placed on a cover slip, located on hotstage furnace, insulated from above by 2 layers (2 cover slips with air space between layers) and hotstage cover, and heated at a rate of 10° C./min. DSC and hotstage results are shown in Table 3.

TABLE 3

DSC and Hotstage Results for Transnorsertraline Salts

| Salt | Peak (° C.) | Onset (° C.) | ΔH$_f$(J/g) | Hotstage Observations |
|---|---|---|---|---|
| HCl | 299.7 | 298.5 | 108.3 | Sublimes at 170° C. Sublimate melts at 250° C. |
| Citrate | not measured | not measured | not measured | Melts at 119° C. |
| Fumarate | 226.7 | 223.9 | 178.9 | Sublimes at 181° C. Sublimate melts at 225° C. |
| Maleate | 177.4 | 174.8 | 49.1 | Melts at 168° C. |
| Phosphate | not measured | not measured | not measured | Melts at 158° C. Recrystallizes at 172° C. Melt at 239° C. |
| Succinate | not measured | not measured | not measured | not measured |
| Sulfate | 125.5, 196.1, 224.6 Exotherm: 148.2 | 114.1, not measured, not measured. | 33.2, not measured, not measured. | Melts at 190 and 204° C. |
| L-tartrate | 128.7, 204.5 | 115.3, 198.6 | 10.6, 171.7 | Melts at 120 and 200° C. |
| Besylate | 192.2 | 190.7 | 52.1 | Melts at 187° C. |
| Tosylate | 248.9 | 247.0 | 54.7 | Melts at 237° C. |
| L-malate | 179.9 | 177.3 | 79.9 | Melts at 165° C. |
| S-mandelate | not measured. | not measured | not measured | Melts at 80° C. |
| Acetate | 146.5 | 143.5 | 137.3 | Melts at 112° C. |
| Benzoate | 151.4 | 149.4 | 83.5 | Melts at 127° C. |
| HBr | 294.5 | 292.5 | 118.5 | Sublimes at 189° C. Sublimate melts at 288° C. |
| Pyroglutamate | not measured | not measured | not measured | not measured |

6.16 Moisture Content and Hygroscopicity of Transnorsertraline Salts

The sixteen salts of transnorsertraline of Example 6.14 were analyzed for moisture content and hygroscopicity. Each salt was analyzed by coulometric titration using an EM Scientific Aquastar C3000 titrator to determine water content. Sample size ranged from 18 mg to 134 mg. Each salt was analyzed using a Perkin Elmer TGA 7 Thermal Gravimetric Analyzer (TGA). Samples were heated from an initial temperature of 25° C. to 325° C. at a rate of 10° C./min. Moisture sorption isotherms for each salt were generated using the VTI SGA-100 Symmetric Vapor Sorption Analyzer. Samples were run as received without pre-analysis drying. Equilibrium criteria were the lesser of 0.01 wt % change in 5 minutes or 180 minutes at each relative humidity (RH) step. Temperature was fixed at 25° C. and the relative humidity steps (25 to 95% to 25%) were in 5% increments. Analysis was repeated for each sample in consecutive analyses (sample was not removed from analyzer). Sample sizes ranged from 18 mg to 35 mg.

VTI moisture isotherm data, moisture content (KF), and TGA data is summarized in Table 4.

TABLE 4

KF, TGA, and VTI Results for Transnorsertraline Salts

| Salt | Initial KF (% H$_2$O) | TGA (% wt loss) | VTI Adsorp. (% wt gain 25 to 95% RH) | VTI Desorp. (% wt loss 95 to 25% RH) |
|---|---|---|---|---|
| HCl | 0.02 | 0.00 | 0.01 | 0.02 |
|  |  |  | 0.01 | 0.02 |
| Citrate | 0.31 | n.m. | 2.59 | 3.96 |
|  |  |  | 3.24 | 3.61 |
| Fumarate | 0.40 | 0.81 | 0.18 | 0.17 |
|  |  |  | 0.17 | 0.16 |
| Maleate | 0.06 | 0.02 | 0.10 | 0.09 |
|  |  |  | 0.08 | 0.08 |
| Phosphate | 0.16 | n.m. | 3.00 | 1.37 |
|  |  |  | 2.14 | 1.20 |
| Succinate | 1.03 | n.m. | 3.25 | 3.17 |
|  |  |  | n.m. | n.m. |
| Sulfate | 3.34 | 4.20 | 10.19 | 9.51 |
|  |  |  | 7.25 | n.m. |
| L-tartrate | 0.62 | n.m. | 3.52 | 1.36 |
|  |  |  | 1.37 | n.m. |
| Besylate | <0.01 | 0.07 | 0.05 | 0.05 |
|  |  |  | 0.05 | 0.05 |
| Tosylate | 0.09 | 0.16 | 0.06 | 0.06 |
|  |  |  | n.m. | n.m. |
| L-malate | 0.05 | 0.07 | 0.08 | 0.08 |
|  |  |  | 0.06 | n.m. |
| S-mandelate | 0.32 | n.m. | 3.24 | 3.95 |
|  |  |  | 3.79 | 3.02 |
| Acetate | 0.03 | 0.53 | 0.07 | 0.08 |
|  |  |  | 0.08 | 0.09 |
| Benzoate | 0.27 | 0.05 | 0.10 | 0.10 |
|  |  |  | 0.08 | 0.07 |
| HBr | 0.04 | 0.06 | 0.35 | 0.30 |
|  |  |  | 0.31 | n.m. |
| Pyroglutamate | 0.10 | n.m. | 17.28 | n.m. |
|  |  |  | n.m. | n.m. | n.m. = not measured

VTI showed that the citrate, phosphate, succinate, sulfate, L-tartrate, S-mandelate, and pyroglutamate salts of transnorsertraline exhibited significant moisture uptake (2.7 to 17.3%) from 25 to 95% RH (Table 4).

6.17 Water Solubility of Transnorsertraline Salts

Twelve salts of transnorsertraline were investigated for their solubility in water: hydrochloride, fumarate, maleate, phosphate, succinate, sulfate, L-tartrate, besylate, tosylate, L-malate, acetate and benzoate. For each salt, saturated solutions with excess solids in deionized water were prepared in 20 mL clear glass scintillation vials with screw caps. All samples were shaken at 300 rpm at ambient conditions for up to nine days until equilibrium was achieved. Solubility was determined using a HPLC method (Table 5).

TABLE 5

Solubility of Transnorsertraline Salts in De-Ionized Water

| Salt | Solubility in Free Base Equivalents mgA/mL | pH |
|---|---|---|
| HCl | 1.81 | 5.32 |
| Fumarate | 0.52 | 5.30 |
| Maleate | 1.88 | 3.98 |
| Phosphate | 4.16 | 3.27 |
| Succinate | 1.04 | 3.89 |
| Sulfate | 0.44 | 2.73 |
| L-tartrate | 0.44 | 2.63 |
| Besylate | 0.99 | 6.00 |
| Tosylate | 0.53 | 6.16 |
| L-malate | 3.04 | 4.15 |
| Acetate | 5.49 | 6.31 |
| Benzoate | 0.59 | 6.34 |

The hydrochloride, maleate, phosphate, succinate, besylate, L-malate, and acetate were among the salts tested that exhibited adequate solubility in water (0.99-5.49 mgA/mL).

6.18 Solubility of Transnorsertraline Salts in Aqueous Buffer

The twelve salts of transnorsertraline of Example 6.4 were investigated for their solubility in the following aqueous buffer systems: simulated gastric fluid (SGF), 0.05 M acetate buffer (pH 4.5) and simulated intestinal fluid (SIF). Saturated solutions with excess solids were prepared in 20 mL clear glass scintillation vials. Simulated gastric fluid (pH 1.0, ~0.1N HCl, 0.03M NaCl, no enzymes), simulated intestinal fluid (pH 6.8, 0.05M KH$_2$PO$_4$, ~0.02N NaOH, no enzymes), and acetate buffer (pH 4.5, 0.02M sodium acetate, 0.03M acetic acid) were prepared in accordance with USP28 (USP28 *Test Solutions p2855, Volumetric Solutions p2863*). All samples were shaken at 300 rpm at ambient conditions up to nine days until equilibrium was attained. Solubility was determined using a HPLC method. (Table 6).

TABLE 6

Solubility of Transnorsertraline Salts in Aqueous Buffer Systems

| Salt (Suffix) | Solubility in Freebase Equivalents mgA/mL | pH |
|---|---|---|
| Test Solvent: Simulated Gastric Fluid[a] | | |
| HCl | 0.13 | 1.28 |
| Fumarate | <0.01 | 1.25 |
| Maleate | 0.08 | 1.25 |
| Phosphate | <0.01 | 1.24 |
| Succinate | 0.08 | 1.27 |
| Sulfate | 0.09 | 1.13 |
| L-tartrate | <0.01 | 1.24 |
| Besylate | <0.01 | 1.18 |
| Tosylate | 0.06 | 1.10 |
| L-malate | 0.08[b] | 1.15 |
| Acetate | 0.07 | 1.26 |
| Benzoate | <0.01 | 1.25 |
| Test Solvent: 0.05M Acetate Buffer (pH 4.5) | | |
| HCl | 2.15 | 4.58 |
| Fumarate | 0.69 | 4.60 |
| Maleate | 1.23 | 4.52 |
| Phosphate | 2.63 | 4.55 |
| Succinate | 0.57 | 4.50 |
| Sulfate | 0.55 | 4.48 |
| L-tartrate | 0.03 | 4.58 |
| Besylate | 1.10 | 4.59 |
| Tosylate | 0.63 | 4.56 |
| L-malate | 1.59[b] | 4.42 |
| Acetate | 3.12 | 4.79 |
| Benzoate | 0.79 | 4.61 |
| Test Solvent: Simulated Intestinal Fluids | | |
| HCl | 0.24 | 6.75 |
| Fumarate | 0.30 | 6.63 |
| Maleate | 0.28 | 6.47 |
| Phosphate | 0.27 | 6.49 |
| Succinate | 0.18 | 6.46 |
| Sulfate | 0.26 | 6.58 |
| L-tartrate | 0.27 | 6.73 |
| Besylate | 0.24 | 6.70 |
| Tosylate | 0.21 | 6.78 |
| L-malate | 0.38 | 6.68 |
| Acetate | 0.25 | 6.63 |
| Benzoate | 0.11 | 6.77 |

[a]enzymes were not included in buffer
[b]equilibrium not reached after 9 days

6.19 Characterization of Transnorsertraline Salts Recovered from Solubility Experiments Solids recovered from solubility experiment suspensions (Examples 6.17 and 6.18) were vacuum filtered and dried at 40° C. overnight. Each sample was analyzed using a Perkin Elmer DSC 7 differential scanning calorimeter. Each sample was heated in a crimped pan with a pinhole under a nitrogen purge at a rate of 10° C./min, from a starting temperature of 25° C. up to a final temperature of 325° C. See Table 7.

As shown in Table 7, the hydrochloride salt of transnorsertraline appeared to convert to a monohydrate form when solids were equilibrated in deionized (DI) water and SGF. The DSC for the hydrochloride monohydrate salt showed an endotherm around 100° C. followed by a melt of the anhydrous sublimate at ~300° C. (confirmed by hotstage). This hydration was also marked by a crystal habit change from rods to plates. See FIGS. 1A and 1B. Additional salts tested appeared to convert to the HCl monohydrate during solubility experiments in SGF (Table 7). This conversion was not unexpected since SGF contains sufficient hydrochloric acid (0.23M) to form the hydrochloride salt, which in turn may convert to the monohydrate. Recovered solids from solubility experiments in acetate buffer did not appear to change from their original salt form. It appears that some of the salts (acetate, maleate, besylate, and L-malate) all converted to a similar form in SIF (Table 7). The DSC for this unknown form shows a single endotherm around 100° C. with a small heat of fusion (29-49 J/g).

TABLE 7

DSC Results for Solids Recovered from Solubility Experiments

| Salt | Test Solvent | DSC Peak (° C.) | DSC ΔH$_f$ (J/g) |
|---|---|---|---|
| HCl | As-is Solid | 299.7 | 99.9 |
|  | Water[c] | 101.4, 297.8 | 113.7, 100.9 |
|  | SGF[a,c] | 101.4, 297.4 | 106.1, 106.6 |
|  | 0.05M Acetate (pH 4.5) | 296.9 | 105.1 |
|  | SIF[b] | n.o. | n.o |
| Fumarate | As-is Solid | 226.7 | 173.2 |
|  | Water | 229.2 | 160.9 |
|  | SGF[a] | 101.9, 297.2 | 105.9, 91.1 |
|  | 0.05M Acetate (pH 4.5) | 230.3 | 155.0 |
|  | SIF[b] | n.o. | n.o. |

TABLE 7-continued

DSC Results for Solids Recovered from Solubility Experiments

| Salt | Test Solvent | DSC Peak (° C.) | DSC ΔH$_f$ (J/g) |
|---|---|---|---|
| Maleate | As-is Solid | 177.7 | 53.0 |
| | Water | 178.4 | 55.0 |
| | SGF[a] | 101.0, 296.7 | 112.2, 102.9 |
| | 0.05M Acetate (pH 4.5) | n.m. | n.m. |
| | SIF[b] | 107.2 | 29.0 |
| Besylate | As-is Solid | 192.1 | 54.7 |
| | Water | 193.0 | 53.1 |
| | SGF[a] | 102.9, 293.9 | 112.1, 91.5 |
| | 0.05M Acetate (pH 4.5) | 191.9 | 55.2 |
| | SIF[b] | 93.0 | 30.5 |
| L-Malate | As-is Solid | 180.3 | 81.3 |
| | Water | 109.1, 178.8 | 54.5, 64.6 |
| | SGF[a] | 100.0, 296.1 | 93.4, 85.4 |
| | 0.05M Acetate (pH 4.5) | 188.2 | 83.7 |
| | SIF[b] | 98.3 | 49.2 |
| Acetate | As-is Solid | 146.3 | 132.2 |
| | Water | 146.4 | 128.9 |
| | SGF[a] | 93.0, 296.0 | 108.7, 100.1 |
| | 0.05M Acetate (pH 4.5) | 145.4 | 121.4 |
| | SIF[b] | 98.9 | 49.4 |
| Benzoate | As-is Solid | 151.2 | 83.4 |
| | Water | 151.5 | 84.8 |
| | SGF[a] | 99.7, 296.9 | 102.4, 103.0 |
| | 0.05M Acetate (pH 4.5) | 151.7 | 85.4 |
| | SIF[b] | n.m. | n.m. |

[a] Simulated Gastric Fluid ("SGF"), USP, pH 0.9, without pepsin
[b] Simulated Intestinal Fluid ("SIF"), USP, pH 6.8, without pancreatin
[c] Recovered solids from water and SGF had 4.8% water (KF) and 4.9% weight loss (TGA), which is consistent with a monohydrate
n.m.: not measured
n.o.: none observed

6.20 Repeat Experiments for the Hydrochloride, Acetate and L-Malate Salts

The following experiments were repeated. Additional lots of the hydrochloride, acetate and L-malate salts of transnorsertraline were tested for (i) consistent thermal properties by DSC and/or hotstage and (ii) consistent moisture properties by KF, TGA and VTI data.

A second lot of the hydrochloride salt of transnorsertraline sublimed at 166° C. and the sublimate melted at 249° C. as measured by hotstage according to the procedure of Example 6.2 above. These results were in good agreement with those of the first lot (sublimed at 170° C., sublimate melted at 250° C.).

The second and third lots of transnorsertraline acetate demonstrated similar thermal properties as the first acetate lot as measured by DSC according to the procedure of Example 6.15 above. (Table 8).

TABLE 8

DSC Results for Transnorsertraline Acetate

| Salt | Lot | Peak (° C.) | Onset (° C.) | ΔH$_f$s (J/g) | Hotstage Observations |
|---|---|---|---|---|---|
| Acetate | 1 | 146.5 | 143.5 | 137.3 | Melts at 112° C. |
| | 2 | 144.9 | 142.2 | 131.2 | n.m. |
| | 3 | 144.8 | 142.4 | 120.1 | n.m. | n.m.: not measured

The second lot of transnorsertraline L-malate demonstrated similar thermal properties as the first acetate lot as measured by DSC; however the third lot melted approximately 8° C. lower than other lots (Table 9). All experiments were performed according to the procedure of Example 6.15 above.

TABLE 9

DSC Results for Transnorsertraline L-Malate

| Salt | Lot | Peak (° C.) | Onset (° C.) | ΔH$_f$s (J/g) | Hotstage Observations |
|---|---|---|---|---|---|
| L-malate | 1 | 179.9 | 177.3 | 79.9 | Melts at 165° C. |
| | 2 | 180.2 | 178.3 | 82.4 | n.m. |
| | 3 | 171.9 | 167.8 | 68.1 | n.m. | n.m.: not measured

A second lot of the hydrochloride salt of transnorsertraline was analyzed for hygroscopicity by VTI according to the procedure of Example 6.16 above. Results were similar as compared to the first hydrochloride lot (VTI adsorption of 0.01% weight gain from 25 to 95% relative humidity; VTI desorption of 0.01% weight loss from 95% to 25% relative humidity).

Second and third lots of the acetate and L-malate salts of transnorsertraline were also analyzed and compared to the results of the first lot according to the procedure of Example 6.3 above. Results are shown in Table 10. All tested second and third lots had similar moisture isotherms as first lots, with the exception of L-malate lot 3, which adsorbed >5% more moisture than other L-malate lots from 25 to 95% relative humidity.

TABLE 10

KF, TGA and VTI Data for Transnorsertraline L-Malate and Transnorsertraline Acetate

| Salt | Lot | Initial KF (% H$_2$O) | TGA (% wt loss) | VTI Adsorp. (% wt gain 25 to 95% RH) | VTI Desorp. (% wt loss 95 to 25% RH) |
|---|---|---|---|---|---|
| L-malate | 1 | 0.05 | 0.08 | 0.08 | 0.08 |
| | | | | 0.06 | n.m. |
| | 2 | 0.08 | n.m. | 0.06 | 0.07 |
| | | | | 0.07 | 0.06 |
| | 3 | 0.04 | n.m. | 5.31 | 5.23 |
| | | | | n.m. | n.m. |
| Acetate | 1 | 0.03 | 0.43 | 0.07 | 0.08 |
| | | | | 0.08 | 0.09 |
| | 2 | 0.07 | n.m. | 0.22 | 0.23 |
| | | | | 0.23 | 0.23 |
| | 3 | 0.05 | n.m. | 0.33 | 0.38 |
| | | | | 0.35 | 0.35 | n.m.: not measured

6.21 Solid Stability of Transnorsertraline Salts

Salts of transnorsertraline were tested for solid stability under various conditions. Solid samples of the HCl salt were placed in double-polyehylene lined high density polyethylene (HDPE) containers closed with HDPE lids and stored at 25° C./60% relative humidity or 40° C./75% relative humidity. Samples were analyzed by HPLC. Transnorsertraline hydrochloride anhydrate was stable at both conditions for at least 6 months and at 25° C./60% relative humidity for 2 years, exhibiting less than 0.05% and less than 0.1% impurities, respectively.

6.22 Polymorphic Conversion Study of Transnorsertraline Hydrochloride

Figure 1B:
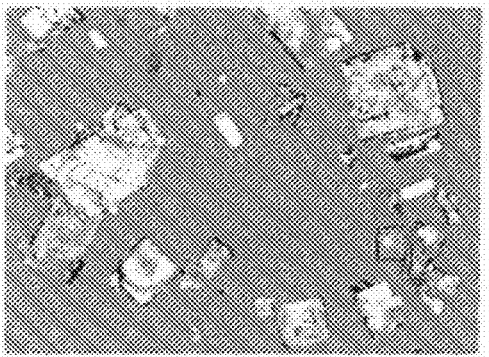
FIG. 1B illustrates the crystal habit of transnorsertraline hydrochloride monohydrate.
Figure 1B:
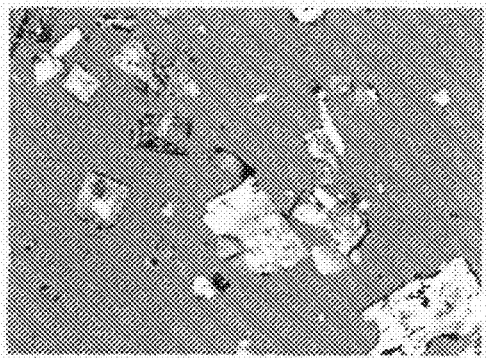

Transnorsertraline hydrochloride exists in at least two crystalline forms. Form A is a crystalline anhydrous material and Form B is a crystalline monohydrate. Polarized light microscopy images show that the two crystalline forms have distinct crystal habits. The anhydrous form displays long thin blades (FIG. 1A), whereas the hydrate form shows thin, approximately square plates (FIG. 1B). Both samples show birefringence and extinguish under cross polarizers upon rotation of the stage.

The study of the conversion of anhydrous transnorsertraline hydrochloride to the hydrate form in aqueous media was investigated, using in-situ Raman monitoring. The system was shown to be suitable for Raman monitoring, with a limit of detection of hydrate form in an anhydrous/hydrate slurry in water at 70 mg/mL below 5.7%.

Raman spectroscopy was performed using a Kaiser Optical Systems Inc. dispersive RamanRXN3 for on-line or in-situ reaction monitoring. The RamanRXN3 system uses an excitation wavelength of 785 nm, with an external cavity-stabilized, diode laser. All spectra were acquired using a ¼″ immersion probe with approximately 100 mW of laser power at the tip of the probe. Different exposure times and numbers of spectrum accumulations were used for the analysis of the two dry samples. An exposure time of 4 seconds with 2 accumulations was used for the monitoring of all form conversions experiments. Wavelength and laser wavelength calibration were performed using an internal neon standard, and diamond Raman shift standard, respectively. The intensity calibration was performed using a Kaiser Raman calibration accessory.

Raman spectra acquired for the two forms in the 2850-3150 $cm^{-1}$ and 200-1600 $cm^{-1}$ regions showed that the two forms can be differentiated by Raman. Regions 660-715 $cm^{-1}$ and 1430-1490 $cm^{-1}$ in particular show little overlapping of the peaks characteristic of each form. Experimental results confirmed that no peaks in the regions 660-720 $cm^{-1}$ and 1430-1490 $cm^{-1}$ were likely to overlap with peaks of interest to follow the conversion between the two crystalline forms of transnorsertraline hydrochloride.

The conversion of anhydrous transnorsertraline hydrochloride to the monohydrate form was monitored in water. The peak ratio I(677 $cm^{-1}$)/I(695 $cm^{-1}$) was observed for a slurry of anhydrous transnorsertraline hydrochloride in water. Based on the peak intensity ratio I(677 $cm^{-1}$)/I(695 $cm^{-1}$), an induction time of approximately 1.1 hour was seen before the beginning of the conversion. The end of the conversion was estimated at approximately 2 hours from the beginning of the slurry. The Raman region 660-710 $cm^{-1}$ showed the appearance of a peak characteristic of the hydrate form and the disappearance of a peak characteristic of the anhydrous form of transnorsertraline hydrochloride. XRPD analysis of the solids collected at the end of the Raman monitoring of the conversion (after approximately 2 h 10 min) was consistent with the hydrate form, with a small amount of anhydrous form detectable. The small amount of anhydrous form may be due to solids present on the walls of the vessel which did not convert. Additionally, the Raman limit of detection of the anhydrous form in the mixture was not estimated.

The conversion of anhydrous transnorsertraline hydrochloride to the hydrate form in water, simulated gastric fluid (SGF) and simulated intestinal fluid (SIF) without enzymes, and 0.1N HCl was monitored at 37° C. The form conversion in water, SGF and 0.1N HCl was shown to begin after approximately 1.3 hours (water and SGF) to 2 hours (0.1N HCl) and be completed within 3 to 4 hours. The form conversion was significantly slower in SIF, which started at approximately 10 hours on small scale and 19 hours on a larger scale and ended after approximately 12.5 hours (small scale) to 36 hours (large scale).

Overall, similar results were obtained in water and simulated gastric fluid, with the start of the form conversion detected at approximately 1.3 hours, with a slightly faster conversion in simulated gastric fluid compared to water. The complete conversion was estimated to occur within 3 to 4 hours in the two media. Slightly longer induction times were observed in 0.1N HCl, approximately 2 to 2.3 hours at larger scale. Complete conversion was observed at approximately 4 hours. Results suggest that the form conversion of transnorsertraline hydrochloride in simulated intestinal fluid is very slow, estimated at 10 hours at small scale and 19 hours at larger scale, and ending after approximately 12.5 hours (small scale) to 36 hours (large scale). XPRD analysis of the solids collected at the end of each experiments were consistent with the hydrate form, with or without some anhydrous form present. The small amount of anhydrous form may be due to residual solids on the walls of the vessel at the time of the slurry.

6.23 Characterization of Anhydrous Crystalline Transnorsertraline Hydrochloride

A sample of anhydrous transnorsertraline hydrochloride (Form A) was submitted for single crystal structure analysis. The structure was determined by single crystal X-ray diffraction. The data collection, reduction and structure determination were not performed according to cGMP specifications.

Experimental

A thin colorless needle of $C_{16}H_{16}Cl_3N$ having approximate dimensions of 0.29×0.08×0.02 mm, was coated with Paratone N oil, suspended in a small fiber loop and placed in a cooled nitrogen gas stream in a random orientation. Preliminary examination and data collection were performed with Cu $K_\alpha$ radiation ($\lambda=1.54178$ Å) on a Bruker D8 APEX II CCD sealed tube diffractometer.

Data collection, indexing and initial cell refinements were all carried out using APEX II. See APEX II, 2005, Broker AXS, Inc., Analytical X-ray Systems, 5465 East Cheryl Parkway, Madison Wis. 53711-5373. Frame integration and final cell refinements were done using SAINT software. Refinements were performed on an PC using SHELXTL. See SAINT Version 6.45A, 2003, Bruker AXS, Inc., Analytical X-ray Systems, 5465 East Cheryl Parkway, Madison Wis. 53711-5373; SHELXTL V6.12, 2002, Bruker AXS, Inc., Analytical X-ray Systems, 5465 East Cheryl Parkway, Madison Wis. 53711-5373.

The final cell parameters and an orientation matrix for data collection were determined from least-squares refinement on 1553 reflections in the range 5.26°<θ<58.04°. The space group was determined to be C2 (no. 5) by the program)(PREP. See Bruker, XPREP in SHELXTL version 6.12, Bruker AXS Inc., Madison, Wis., USA, 2002.

The data were collected using a series of combinations of phi and omega scans with 30 second frame exposures and 0.5° frame widths at a temperature of 173±2 K. The data were collected to a maximum 2θ value of 116.08°.

A total of 2910 reflections were collected, of which 1533 were unique. Lorentz and polarization corrections were applied to the data. The linear absorption coefficient is 52.75 $cm^{-1}$ for Cu $K_\alpha$ radiation. An empirical absorption correction using SADABS was applied. See Blessing, R. H., *SADABS*, Program for absorption correction using Siemens CCD. Based on Blessing R. *Acta Cryst.* 1995, A51, 33. Transmission coefficients ranged from 0.3099 to 0.9018. Intensities of equivalent reflections were averaged. The agreement factor for the averaging was 4.1% based on intensity.

Structure Solution and Refinement

The structure was solved by direct methods using SHELXS-97. See Sheldrick, G. M. *SHELX97, A Program for the Solution of Crystal Structure*, University of Gottingen, Germany, 1997. Hydrogen atoms were placed at their expected chemical positions using the HFIX command or were located in a final difference Fourier and were included in the final cycles of least squares with isotropic $U_{ij}$'s related to the atom to which they are bonded. All non-hydrogen atoms were refined anisotropically. The structure was refined in full-matrix least-squares by minimizing the function:

$$\Sigma w(|F_o|^2-|F_c|^2)^2$$

The weight $w$ is defined as $1/[\sigma^2(F_o^2)+(0.0450P)^2+(0.3158P)]$, where $P=(F_o^2+2F_o^2)/3$. Scattering factors were taken from the "International Tables for Crystallography." International Tables for Crystallography, Vol. C, Kluwer Academic Publishers: Dordrecht, The Netherlands, 1992, Tables 4.2.6.8 and 6.1.1.4. Of the 3171 reflections used in the refinements, only the reflections with $F_o^2>2\sigma(F_o^2)$ were used in calculating R. A total of 1553 reflections were used in the calculation. The final cycle of refinement included variable parameters and converged (largest parameter shift was essentially equal to its estimated standard deviation) with unweighted and weighted agreement factors of:

$$R=\Sigma|F_o-F_c|/\Sigma F_o=0.0566$$

$$R_w=\sqrt{(\Sigma w(F_o^2-F_c^2)^2/\Sigma w(F_o^2)^2)}=0.1470$$

The standard deviation of an observation of unit weight was 1.074. The highest peak in the final difference Fourier had a height of 1.115 e/Å$^3$. The minimum negative peak had a height of −0.288 e/Å$^3$. The factor for the determination of the absolute structure refined to 0.04(4). See Flack, H. D. *Acta Cryst.* 1983, A39, 876.

Results

The monoclinic cell parameters and calculated volume are: a=16.834(3), b=5.2264(9), c=19.059(3) Å, α=90.00, β=113.103(6), γ=90.00°, V=1542.4(4) Å$^3$. The formula weight for transnorsertraline is 328.65 g/mol with Z=4 and a calculated density of 1.415 g cm$^{-3}$. The space group was determined to be C2 (no. 5). A summary of the crystal data and crystallographic data collection parameters are provided in Table 11.

The quality of the structure obtained is considered to be moderate to high, as indicated by the R-value of 0.0566 (5.66%). The R-value for this structure is just inside the R-value range of 0.02 to 0.06 which are quoted for the most reliably determined structures. Glusker, Jenny Pickworth; Trueblood, Kenneth N. *Crystal Structure Analysis: A Primer*, 2$^{nd}$ ed.; Oxford University press: New York, 1985; p. 87.

TABLE 11

Crystal Data and Data Collection Parameters for Anhydrous Transnorsertraline Hydrochloride

| | |
|---|---|
| Empirical formula | $C_{16}H_{16}Cl_3N$ |
| Formula weight | 328.65 |
| Temperature | 173(2) K |
| Wavelength | 1.54178 Å |
| Crystal system | Monoclinic |
| Space group | C2 |
| Unit cell dimensions | a = 16.834(3) Å   α = 90°. |
| | b = 5.2264(9) Å   β = 113.103(6)°. |
| | c = 19.059(3) Å   γ = 90°. |
| Volume | 1542.4(4) Å$^3$ |
| Z | 4 |
| $d_{calc}$, g cm$^{-3}$ | 1.415 |

TABLE 11-continued

Crystal Data and Data Collection Parameters for Anhydrous Transnorsertraline Hydrochloride

| | |
|---|---|
| Absorption coefficient | 5.275 mm$^{-1}$ |
| F(000) | 680 |
| Crystal size | 0.29 × 0.08 × 0.02 mm$^3$ |
| Theta range for data collection | 5.26 to 58.04°. |
| Index ranges | −18 <= h <= 17, −5 <= k <= 5, −20 <= l <= 20 |
| Reflections collected | 2910 |
| Independent reflections | 1533 [R (int) = 0.0409] |
| Completeness to theta = 58.04° | 89.2% |
| Absorption correction | Semi-empirical from equivalents |
| Max. and min. transmission | 0.9018 and 0.3099 |
| Refinement method | Full-matrix least-squares on F$^2$ |
| Data/restraints/parameters | 1533/1/181 |
| Goodness-of-fit on F$^2$ | 1.074 |
| Final R indices [I > 2σ(I)] | R1 = 0.0566, wR2 = 0.1470 |
| R indices (all data) | R1 = 0.0655, wR2 = 0.1550 |
| Absolute structure parameter | 0.04(4) |
| Largest diff. peak and hole | 1.115 and −0.288 e · Å$^{-3}$ |

Calculated X-Ray Powder Diffraction Pattern

A calculated X-ray Powder Diffraction Pattern (XRPD) pattern was generated for Cu radiation using PowderCell 2.3 and the atomic coordinates, space group, and unit cell parameters from the single crystal data. See PowderCell for Windows Version 2.3 Kraus, W.; Nolze, G. Federal Institute for Materials Research and Testing, Berlin Germany, EU, 1999.

Figure 2:
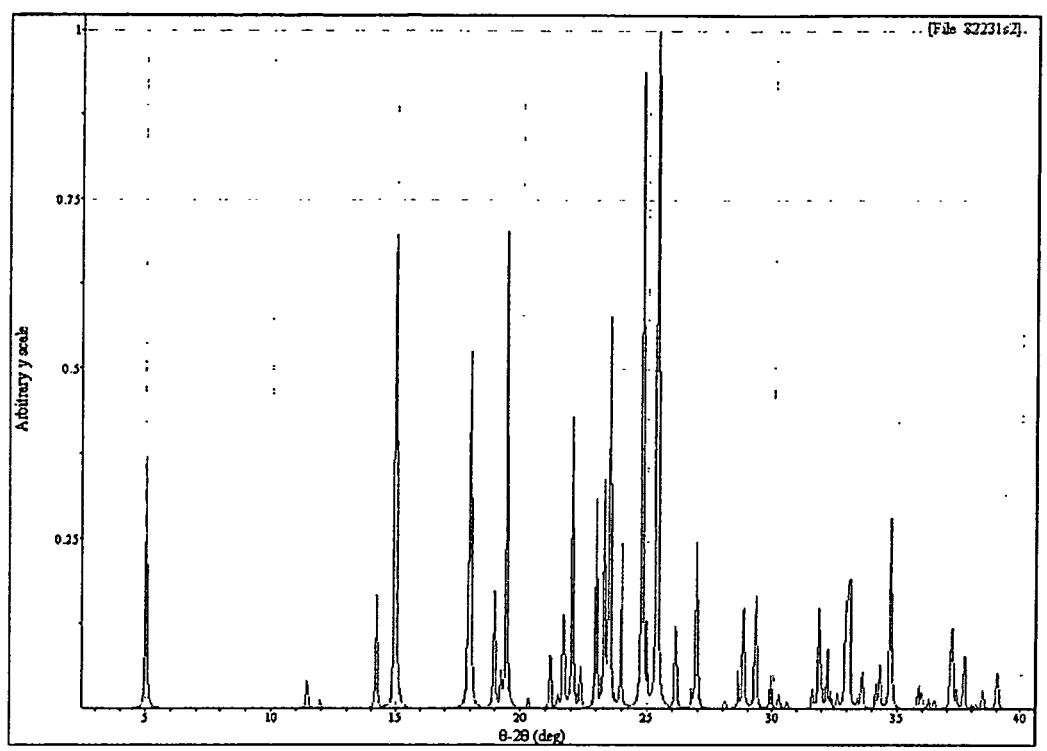
FIG. 2 illustrates the calculated XRPD pattern of anhydrous transnorstertraline hydrochloride.
Figure 3:
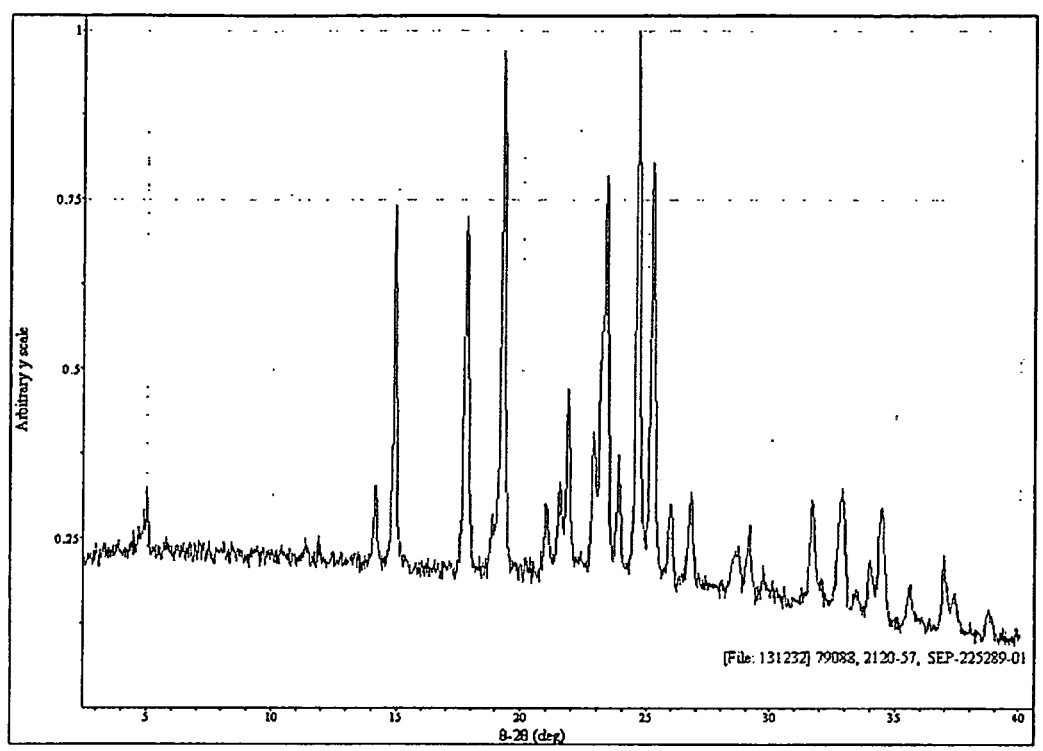
FIG. 3 illustrates the experimental XRPD pattern of anhydrous transnorstertraline hydrochloride.

The calculated XRPD pattern of anhydrous transnorsertraline hydrochloride is shown in FIG. 2. The experimental XRPD pattern is shown in FIG. 3. All peaks in the experimental patterns are represented in the calculated XRPD pattern, indicating the bulk material is likely a single phase. The differences in the calculated and observed intensities in the XRPD patterns are likely due to preferred orientation. Preferred orientation is the tendency for crystals, usually plates or needles, to align themselves with some degree of order. Preferred orientation can affect peak intensities, but not peak positions, in XRPD patterns. The slight shifts in peak location are likely the result of slight shifts in the unit cell parameters as a function of temperature. The calculated XRPD patterns in generated from the single crystal data which was collected at 173 K, while the experimental powder pattern was collected at ambient temperature. Collecting data at low temperature is typically used in single crystal analysis to improve the quality of the structure.

ORTEP and Packing Diagrams

The ORTEP diagram was prepared using ORTEP III. See Johnson, C. K. ORTEPIII, Report ORNL-6895, Oak Ridge National Laboratory, TN, U.S.A. 1996. OPTEP-3 for Windows V1.05 Farrugia, L. J., *J. Appl. Cryst.* 1997, 30, 565. Atoms are represented by 50% probability anisotropic thermal ellipsoids. Packing diagrams were prepared using CAMERON modeling software. See Watkin, D. J.; Prout, C. K.; Pearce, L. J. CAMERON, Chemical Crystallography Laboratory, University of Oxford, Oxford, 1996. Additional figures were generated using Mercury 1.3 modeling software. See Bruno, I. J. Cole, J. C. Edgington, P. R. Kessler, M. K. Macrae, C. F. McCabe, P. Pearson, J. and Taylor, R. *Acta Crystallogr.*, 2002 B58, 389. Hydrogen bonding is represented as dashed lines.

Figure 4:
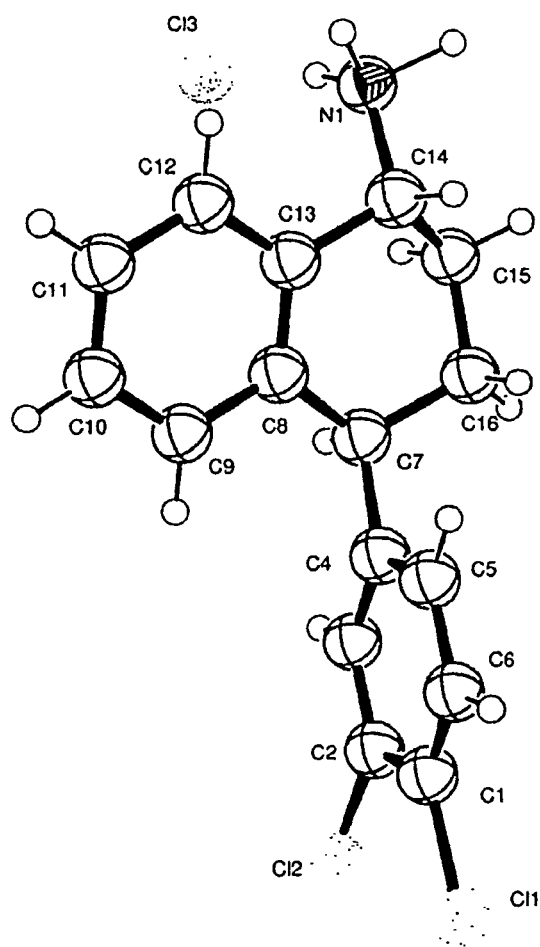
FIG. 4 illustrates the ORTEP diagram of anhydrous transnorstertraline hydrochloride.

An ORTEP drawing of anhydrous transnorsertraline hydrochloride is shown in FIG. 4. The asymmetric unit shown in FIG. 4 contains a single protonated transnorsertraline molecule and a chloride anion.

Absolute Configuration

The absolute configuration of anhydrous transnorsertraline hydrochloride can be determined by analysis of anomalous X-ray scattering by the crystal. The differences in intensities of the anomalous scattering are then compared with calculated scattering intensities for each enantiomer. These measured and calculated intensities can then be fit to a parameter, the Flack factor. See Flack, H. D.; Bemardinelli, G. *Acta Cryst.* 1999, A55, 908; Flack, H. D.; Bemardinelli, G. *J. Appl. Cryst.* 2000, 33, 1143. After a structure is solved the quality of the data is assessed for its inversion-distinguishing power, this is done by an examination of the standard uncertainty of the Flack parameter. For anhydrous transnorsertraline hydrochloride, the standard uncertainty, (u), equals 0.07, which is classified as enantiopure-sufficient distinguishing power. The measured Flack factor for the crystal structure of anhydrous transnorsertraline hydrochloride shown in FIG. 4 is −0.13 with a standard uncertainty of 0.04. The molecule contains two chiral centers located at C7 and C14 (refer to FIG. 4), which were assigned as S and R configurations, respectively.

6.24 X-Ray Powder Diffraction Analysis of Anhydrous Transnorsertraline Hydrochloride X-ray powder diffraction (XRPD) analyses of anhydrous transnorsertraline hydrochloride were performed using an Inel XRG-3000 diffractometer equipped with a CPS (Curved Position Sensitive) detector with a 2θ range of 120°. Real time data were collected using Cu-Kα radiation starting at approximately 4° 2θ at a resolution of 0.03° 2θ. The tube voltage and amperage were set to 40 kV and 30 mA, respectively. The monochromator slit was set at 5 mm by 160 µm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard. The experimental XRPD patterns were collected according to cGMP specifications. Table 12 shows observed XRPD peaks for anhydrous transnorsertraline hydrochloride.

TABLE 12

Observed XRPD Peaks for Anhydrous Transnorsertraline HCl

| °2θ | d space (Å) | Intensity (%) |
| --- | --- | --- |
| 5.00 ± 0.10 | 17.687 ± 0.361 | 33 |
| 11.37 ± 0.10 | 7.783 ± 0.069 | 23 |
| 11.85 ± 0.10 | 7.466 ± 0.063 | 26 |
| 14.11 ± 0.10 | 6.279 ± 0.045 | 33 |
| 14.87 ± 0.10 | 5.959 ± 0.040 | 74 |
| 17.78 ± 0.10 | 4.989 ± 0.028 | 73 |
| 18.85 ± 0.10 | 4.707 ± 0.025 | 29 |
| 19.23 ± 0.10 | 4.615 ± 0.024 | 97 |
| 20.96 ± 0.10 | 4.237 ± 0.020 | 30 |
| 21.48 ± 0.10 | 4.136 ± 0.019 | 33 |
| 21.83 ± 0.10 | 4.071 ± 0.019 | 47 |
| 22.84 ± 0.10 | 3.894 ± 0.017 | 41 |
| 23.29 ± 0.10 | 3.820 ± 0.016 | 78 |
| 23.81 ± 0.10 | 3.738 ± 0.016 | 37 |
| 24.57 ± 0.10 | 3.624 ± 0.015 | 100 |
| 25.19 ± 0.10 | 3.535 ± 0.014 | 80 |
| 25.95 ± 0.10 | 3.433 ± 0.013 | 30 |
| 26.79 ± 0.10 | 3.328 ± 0.012 | 31 |
| 28.66 ± 0.10 | 3.115 ± 0.011 | 23 |
| 29.14 ± 0.10 | 3.064 ± 0.010 | 27 |

Table 13 shows prominent XRPD peaks for anhydrous transnorsertraline hydrochloride. Differences between calculated and experimental peaks are due to preferred orientation and particle statistic effects.

TABLE 13

Prominent XRPD Data for Anhydrous Transnorsertraline HCl

| Calculated (°2θ) | Experimental (°2θ) |
| --- | --- |
| 5.05 | 5.00 |
| 15.00 | 14.87 |
| 18.00 | 17.78 |
| 19.45 | 19.23 |
| 22.00 | 21.83 |
| 23.50 | 23.29 |
| 24.75 | 24.57 |
| 25.35 | 25.19 |

6.25 Characterization of Crystalline Transnorsertraline Hydrochloride Monohydrate A sample of transnorsertraline hydrochloride monohydrate (Form B) was submitted for single crystal structure analysis. The single crystal data collection, structure solution and refinement were not performed according to cGMP specifications.

Experimental

A colorless needle of transnorsertraline hydrochloride monohydrate, $C_{16}H_{18}Cl_3NO$ [$Cl,C_{16}H_{16}Cl_2N,H_2O$], having approximate dimensions of 0.60×0.40×0.07 mm, was mounted on a glass fiber in random orientation. Preliminary examination and data collection were performed with Mo $K_\alpha$ radiation (λ=0.71073 Å) on a Nonius KappaCCD diffractometer equipped with a graphite crystal, incident beam monochromator. Refinements were performed on an LINUX PC using SHELX97. See Sheldrick, G. M. *SHELX97, A Program for Crystal Structure Refinement*, University of Gottingen, Germany, 1997.

Cell constants and an orientation matrix for data collection were obtained from least-squares refinement using the setting angles of 6712 reflections in the range 3°<θ<27°. The refined mosaicity from DENZO/SCALEPACK was 0.47° indicating good crystal quality. See Otwinowski, Z.; Minor, W. *Methods Enzymol.* 1997, 276, 307. The space group was determined by the program ABSEN. See McArdle, P. C. *J. Appl. Cryst.* 1996, 29, 306. From the systematic presence of the following condition: 0k0 k=2n, and from subsequent least-squares refinement, the space group was determined to be $P2_1$ (no. 4). This is a chiral space group. The data were collected to a maximum 2θ value of 54.92°, at a temperature of 150±1 K.

Frames were integrated with DENZO-SMN. See Otwinowski, Z.; Minor, W. *Methods Enzymol.* 1997, 276, 307. A total of 6712 reflections were collected, of which 3171 were unique. Lorentz and polarization corrections were applied to the data. The linear absorption coefficient is 0.543 mm$^{-1}$ for Mo $K_\alpha$ radiation. An empirical absorption correction using SCALEPACK was applied. Id. Transmission coefficients ranged from 0.892 to 0.963. Intensities of equivalent reflections were averaged. The agreement factor for the averaging was 4.5% based on intensity.

Structure Solution and Refinement

The structure was solved by direct methods using SIR2004. See Burla et al., *J. Appl. Cryst.* 2005, 38, 381. The remaining atoms were located in succeeding difference Fourier syntheses. Hydrogen atoms were included in the refinement but restrained to ride on the atom to which they are bonded. The structure was refined in full-matrix least-squares by minimizing the function:

$$\Sigma w(|F_o|^2-|F_c|^2)^2$$

The weight w is defined as $1/[\sigma^2(F_o^2)+(0.0450P)^2+(0.3158P)]$, where $P=(F_o^2+2F_c^2)/3$. Scattering factors were taken from the "International Tables for Crystallography." International Tables for Crystallography, Vol. C, Kluwer Academic Publishers: Dordrecht, The Netherlands, 1992, Tables 4.2.6.8 and 6.1.1.4. Of the 3171 reflections used in the refinements, only the reflections with $F_o^2>2\sigma(F_o^2)$ were used in calculating R. A total of 2757 reflections were used in the calculation. The final cycle of refinement included 210 variable parameters and converged (largest parameter shift was essentially equal to its estimated standard deviation) with unweighted and weighted agreement factors of:

$$R=\Sigma|F_o-F_c|/\Sigma F_o=0.041$$

$$R_w=\sqrt{(\Sigma w(F_o^2-F_c^2)^2/\Sigma w(F_o^2)^2)}=0.093$$

The standard deviation of an observation of unit weight was 1.04. The highest peak in the final difference Fourier had a height of 0.35 e/Å$^3$. The minimum negative peak had a height of −0.37 e/Å$^3$. The factor for the determination of the absolute structure refined to −0.13(7). See Flack, H. D. *Acta Cryst.* 1983, A39, 876.

Results

The monoclinic cell parameters and calculated volume are: a=7.2962(2) Å, b=7.5569(2) Å, c=15.2870(5) Å, α=90.00, β=90.0852(14), γ=90.00°, V=842.87(4) Å$^3$. For the monohydrate, the formula weight is 346.69 g/mol with Z=2 resulting in a calculated density of 1.366 g cm$^{-3}$. The space group was determined to be P2$_1$ (no. 4), which is a chiral space group. A summary of the crystal data and crystallographic data collection parameters are provided in Table 14. The quality of the structure obtained is high, as indicated by the R-value of 0.041 (4.1%). Usually R-values in the range of 0.02 to 0.06 are quoted for the most reliably determined structures. Glusker, Jenny Pickworth; Trueblood, Kenneth N. *Crystal Structure Analysis: A Primer*, 2$^{nd}$ ed.; Oxford University press: New York, 1985; p. 87.

TABLE 14

Crystal Data and Data Collection Parameters for Transnorsertraline Hydrochloride Monohydrate

| | |
|---|---|
| formula | C$_{16}$H$_{18}$Cl$_3$NO |
| formula weight | 346.69 |
| space group | P2$_1$ (No. 4) |
| a, Å | 7.2962(2) |
| b, Å | 7.5569(2) |
| c, Å | 15.2870(5) |
| β, deg | 90.0852(14) |
| V, Å$^3$ | 842.87(4) |
| Z | 2 |
| d$_{calc}$, g cm$^{-3}$ | 1.366 |
| crystal dimensions, mm | 0.60 × 0.40 × 0.07 |
| temperature, K | 150. |
| radiation (wavelength, Å) | Mo K$_\alpha$ (0.71073) |
| monochromator | graphite |
| linear abs coef, mm$^{-1}$ | 0.543 |
| absorption correction applied | empirical[a] |
| transmission factors: min, max | 0.892 to 0.963 |
| diffractometer | Nonius KappaCCD |
| h, k, l range | −9 to 9 −9 to 8 −19 to 19 |
| 2θ range, deg | 5.33-54.92 |
| mosaicity, deg | 0.47 |
| programs used | SHELXTL |
| F$_{000}$ | 360.0 |
| weighting | $1/[\sigma^2(F_o^2) + (0.0450P)^2 + 0.3158P]$ where $P = (F_o^2 + 2F_c^2)/3$ |
| data collected | 6712 |
| unique data | 3171 |
| R$_{int}$ | 0.045 |
| data used in refinement | 3171 |
| cutoff used in R-factor calculations | $F_o^2 > 2.0\sigma(F_o^2)$ |
| data with I > 2.0σ(I) | 2757 |
| number of variables | 210 |
| largest shift/esd in final cycle | 0.00 |
| R(F$_o$) | 0.041 |
| R$_w$(F$_o^2$) | 0.093 |
| goodness of fit | 1.043 |
| absolute structure determination | Flack parameter[b] (−0.13(7)) |

[a]Otwinowski Z. & Minor, W. *Methods Enzymol.*, 1997, 276, 307.
[b]Flack, H. D. *Acta Cryst.*, 1983 A39, 876.

Calculated X-Ray Powder Diffraction Pattern

A calculated X-ray Powder Diffraction Pattern (XRPD) pattern was generated for Cu radiation using PowderCell 2.3 and the atomic coordinates, space group, and unit cell parameters from the single crystal data. See PowderCell for Windows Version 2.3 Kraus, W.; Nolze, G. Federal Institute for Materials Research and Testing, Berlin Germany, EU, 1999.

Figure 5:
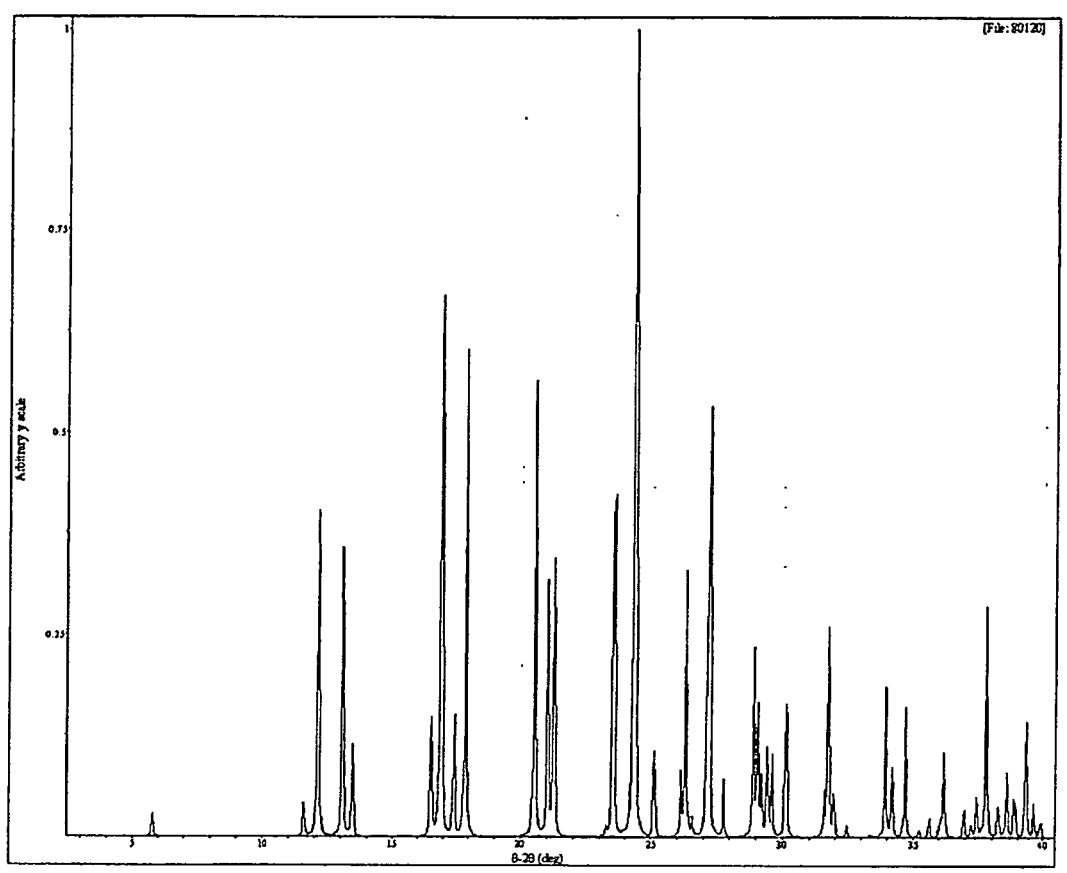
FIG. 5 illustrates the calculated XRPD pattern of transnorstertraline hydrochloride monohydrate.
Figure 6:
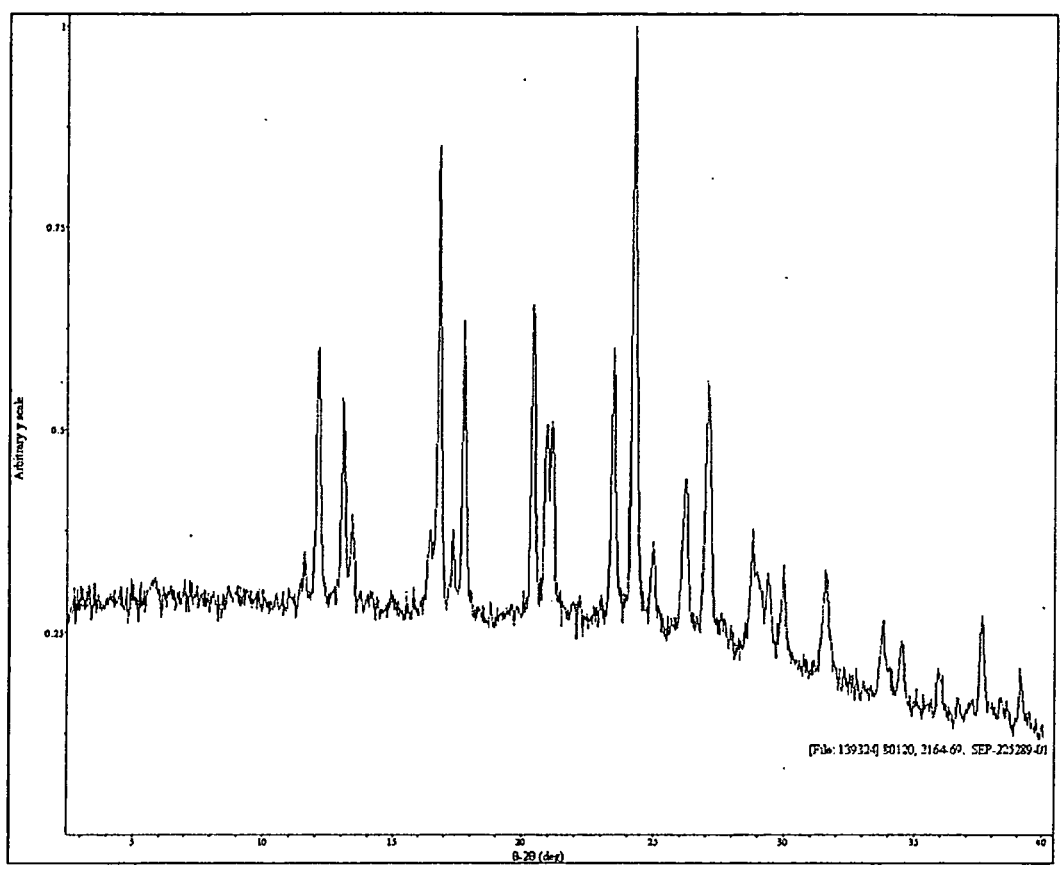
FIG. 6 illustrates the experimental XRPD pattern of transnorstertraline hydrochloride monohydrate.

The calculated XRPD pattern of transnorstertraline hydrochloride monohydrate is shown in FIG. 5. The experimental XRPD pattern is shown in FIG. 6. All peaks in the experimental patterns are represented in the calculated XRPD pattern, indicating the bulk material is likely a single phase. The slight shifts in peak location are likely the result of slight shifts in the unit cell parameters as a function of temperature. The calculated XRPD patterns in generated from the single crystal data which was collected at 150 K, while the experimental powder pattern was collected at ambient temperature. Collecting data at low temperature is typically used in single crystal analysis to improve the quality of the structure.

ORTEP and Packing Diagrams

The ORTEP diagram was prepared using ORTEP III. See Johnson, C. K. ORTEPIII, Report ORNL-6895, Oak Ridge National Laboratory, TN, U.S.A. 1996. OPTEP-3 for Windows V1.05 Farrugia, L. J., *J. Appl. Cryst.* 1997, 30, 565. Atoms are represented by 50% probability anisotropic thermal ellipsoids. Packing diagrams were prepared using CAMERON modeling software. See Watkin, D. J.; Prout, C. K.; Pearce, L. J. CAMERON, Chemical Crystallography Laboratory, University of Oxford, Oxford, 1996. Additional figures were generated using Mercury 1.4.1. See Bruno, I. J. Cole, J. C. Edgington, P. R. Kessler, M. K. Macrae, C. F. McCabe, P. Pearson, J. and Taylor, R. *Acta Crystallogr.*, 2002 B58, 389. Hydrogen bonding is represented as dashed lines.

Figure 7:
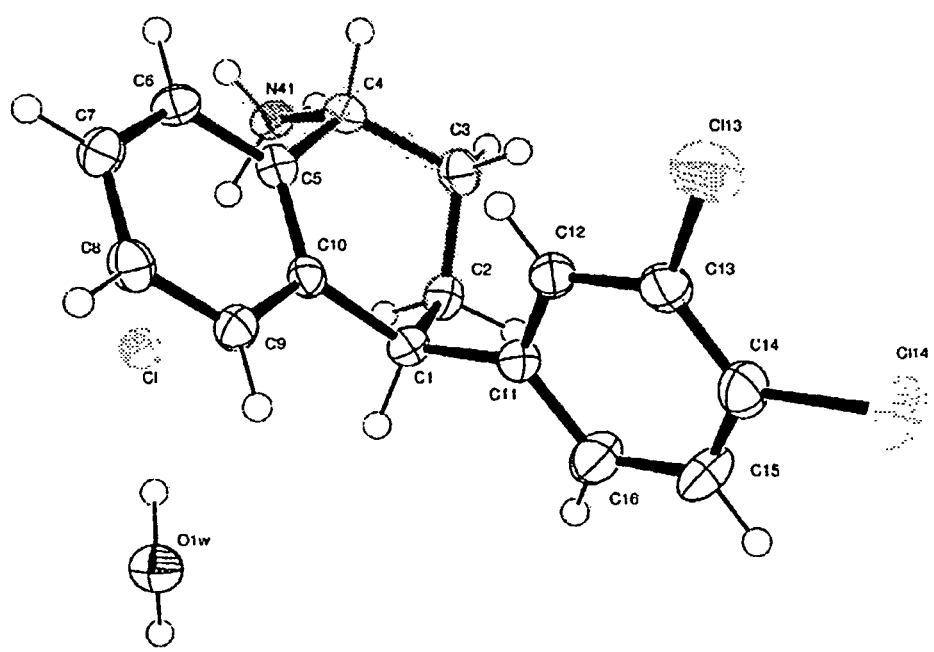
FIG. 7 illustrates the ORTEP diagram of transnorsertraline hydrochloride monohydrate.

An ORTEP drawing of transnorsertraline hydrochloride monohydrate is shown in FIG. 7. The asymmetric unit shown contains a single protonated transnorsertraline hydrochloride monohydrate molecule, a chloride anion and a fully occupied water of hydration. Salt formation was confirmed by locating the hydrogen atoms on the primary amine and the water molecule directly from the Fourier map.

Absolute Configuration

The absolute configuration of transnorsertraline hydrochloride monohydrate can be determined by analysis of anomalous X-ray scattering by the crystal. The differences in intensities of the anomalous scattering are then compared with calculated scattering intensities for each enantiomer. These measured and calculated intensities can then be fit to a parameter, the Flack factor. See Flack, H. D.; Bernardinelli, G. *Acta Cryst.* 1999, A55, 908; Flack, H. D.; Bernardinelli, G. *J. Appl. Cryst.* 2000, 33, 1143. After a structure is solved the quality of the data is assessed for its inversion-distinguishing power, this is done by an examination of the standard uncertainty of the Flack parameter. The measured Flack factor for the crystal structure of transnorsertraline hydrochloride monohydrate shown in FIG. 7 is −0.13 with a standard uncertainty of 0.07. The standard uncertainty, (u), equals 0.07, which is classified as enantiopure-sufficient distinguishing power. An error of this magnitude means that a priori biological, chemical or physical evidence is required to show that the compound is truly enantiopure, and to prove that the absolute structure determination is valid. While the measured Flack factor is outside the range to allow validation based solely on the crystallographic data, the absolute configuration can be confirmed by comparison to the transnorsertraline hydrochloride molecule from the anhydrous crystal structure. Therefore, the absolute configuration of the model in FIG. 7 is correct. The transnorsertraline hydrochloride monohydrate molecule contains two chiral centers located at C1 and C4 (refer to FIG. 7), which were assigned as S and R configuration, respectively.

6.26 X-Ray Powder Diffraction Analysis of Transnorsertraline Hydrochloride Monohydrate X-ray powder diffraction (XRPD) analyses of transnorsertraline hydrochloride monohydrate were performed using an Inel XRG-3000 diffractometer equipped with a CPS (Curved Position Sensitive) detector with a 2θ range of 120°. Real time data were collected using Cu-Kα radiation starting at approximately 4° 2θ at a resolution of 0.03° 2θ. The tube voltage and amperage were set to 40 kV and 30 mA, respectively. The monochromator slit was set at 5 mm by 160 µm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard. The experimental XRPD patterns were collected according to cGMP specifications. Table 15 shows observed XRPD peaks for transnorsertraline hydrochloride monohydrate.

TABLE 15

Observed XRPD Peaks for Transnorsertraline HCl Monohydrate

| °2θ | d space (Å) | Intensity (%) |
|---|---|---|
| 11.55 ± 0.10 | 7.660 ± 0.067 | 35 |
| 12.07 ± 0.10 | 7.331 ± 0.061 | 60 |
| 13.01 ± 0.10 | 6.806 ± 0.053 | 54 |
| 13.35 ± 0.10 | 6.631 ± 0.050 | 40 |
| 16.40 ± 0.10 | 5.405 ± 0.033 | 38 |
| 16.78 ± 0.10 | 5.283 ± 0.031 | 85 |
| 17.30 ± 0.10 | 5.126 ± 0.030 | 38 |
| 17.75 ± 0.10 | 4.997 ± 0.028 | 64 |
| 20.38 ± 0.10 | 4.357 ± 0.021 | 66 |
| 20.90 ± 0.10 | 4.250 ± 0.020 | 51 |
| 21.11 ± 0.10 | 4.209 ± 0.020 | 51 |
| 23.43 ± 0.10 | 3.797 ± 0.016 | 60 |
| 24.19 ± 0.10 | 3.679 ± 0.015 | 100 |
| 24.92 ± 0.10 | 3.573 ± 0.014 | 36 |
| 26.17 ± 0.10 | 3.406 ± 0.013 | 44 |
| 27.07 ± 0.10 | 3.294 ± 0.012 | 55 |
| 28.77 ± 0.10 | 3.104 ± 0.011 | 35 |
| 29.35 ± 0.10 | 3.043 ± 0.010 | 32 |
| 29.94 ± 0.10 | 2.984 ± 0.010 | 33 |

Table 16 shows prominent XRPD peaks for transnorsertraline hydrochloride monohydrate. Differences between calculated and experimental peaks are due to preferred orientation and particle statistic effects.

TABLE 16

Prominent XRPD Data for Transnorsertraline HCl Monohydrate

| Calculated (°2θ) | Experimental (°2θ) |
|---|---|
| 12.10 | 12.07 |
| 13.05 | 13.01 |
| 16.90 | 16.78 |
| 17.85 | 17.75 |
| 20.50 | 20.38 |
| 21.00 | 20.90 |
| 21.25 | 21.11 |
| 23.55 | 23.43 |
| 24.30 | 24.19 |
| 26.30 | 26.17 |
| 27.20 | 27.07 |

6.27 Additional Transnorsertraline HCl Stability Studies

In a typical stability study, the excipient blend or completed dosage form was prepared with the active drug. The material was stored in a sealed container, preferably a high-density polyethylene (HDPE) bottle sealed with a heat induction foil. The material was placed in an oven with controlled humidity such that the samples were exposed to about 40° C. and about 75% relative humidity (RH) for a period of about 2 weeks to about 6 months.

Figure 8:
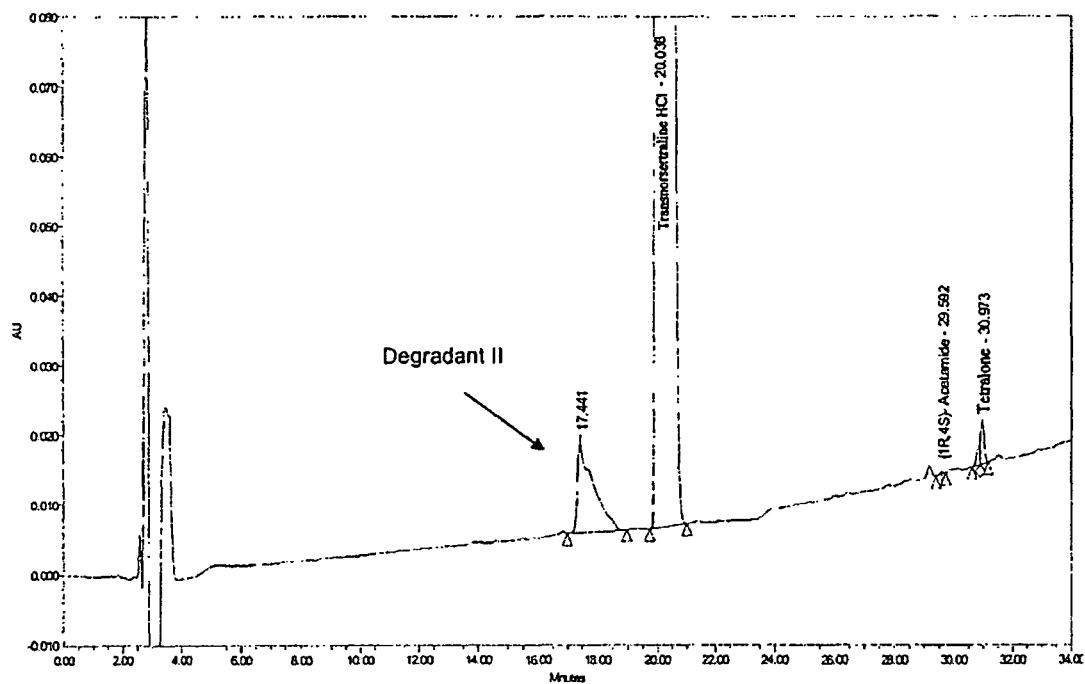
FIG. 8 is a typical HPLC chromatogram of transnorsertraline hydrochloride 1 mg Tablets of example 6.27.

Table 17 shows the assay and impurities data for the tablets through six months storage using HPLC. A typical HPLC chromatogram is shown in FIG. 8. At $t_0$, assay was ~93% while total impurities were 0.89%, 0.17% of which could be attributed to tetralone. An unknown impurity (RT ~18 minutes, 0.67%) was also detected during $t_o$ analysis. From an initial value of 93.4%, assay values for tablets stored at 30° C./65% RH and 25° C./60% RH remained above 90% through the six month time point while those stored at 40° C./75% RH dropped to 80%. At 40° C./75% RH, the major degradant was tetralone; levels increased from an initial value of 0.17% to 4.63% at six months. In contrast, the unknown impurity levels at 25° C./60% RH rose from an initial value of 0.67% to 1.84% within a month, subsequently dropping to 0.23% at the six month time point.

TABLE 17

Assay and Impurities Data of Transnorsertraline HCl 1 mg Tablets

| Time point | Condition | % Degradant | % Tetralone | % Total impurities | % Assay |
|---|---|---|---|---|---|
| $t_0$ | — | 0.67 | 0.17 | 0.89 | 93.4 |
| 1 Month | 25° C./60% RH | 1.84 | 0.12 | 2.23 | 93.9 |
| | 40° C./75% RH | 0.17 | 0.80 | 2.19 | 91.0 |
| 2 Months | 25° C./60% RH | 1.19 | 0.16 | 1.64 | 88.5 |
| | 40° C./75% RH | 0.09 | 1.39 | 2.94 | 84.7 |
| 3 Months | 25° C./60% RH | 0.75 | 0.31 | 1.45 | 92.3 |
| | 30° C./65% RH | 0.24 | 0.55 | 1.34 | 92.0 |
| | 40° C./75% RH | 0.09 | 2.68 | 4.69 | 86.2 |
| 6 Months | 25° C./60% RH | 0.23 | 0.39 | 1.04 | 91.4 |
| | 30° C./65% RH | 0.24 | 0.70 | 1.54 | 90.3 |
| | 40° C./75% RH | 0.07 | 4.63 | 6.77 | 80.6 |

The structure of the degradant was confirmed by its HPLC retention time, UV spectrum and LC-MS result as having formula II. The degradant has a molecular weight of 454, and its chemical structure is shown below:

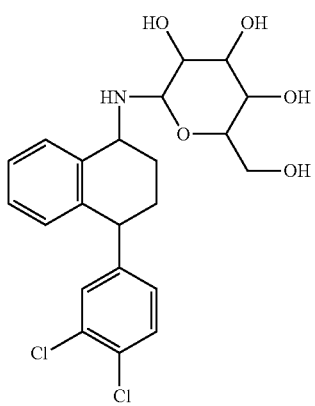

(II)

The data from additional studies indicated that 0.005% of mannose in mannitol resulted in conjugate degradant formation of about 0.12% in two weeks, and that of 0.01% of mannose in mannitol resulted in conjugate degradant formation of about 0.25% in two weeks. The amount of conjugate degradant leveled off at about two weeks and then slightly declined as stress time increases. Formation of the degradant of formula II also depends on the temperature. At higher temperature (e.g., >35° C.), the degradant of formula II underwent decomposition.

6.28 Analysis of Mannitol Excipient Purity

Further stability studies on capsules have shown that the blends in tablets packaged in Aclar® (polychlorotrifluoroethylene film, Honeywell Int'l Inc.) are more stable (approximately 4 times) than blends in open dish conditions. The presence of mannose in mannitol was determined using HPLC-Corona charged Aerosol Detector (HPLC-CAD) and Ion Chromatography (IC) methods as shown in Table 18:

TABLE 18

Analysis of Mannitol Purity

| | % Mannose in Mannitol | |
|---|---|---|
| Mannitol Lot | HPLC-CAD | IC |
| 1 | 0.001 | 0.001 |
| 2 | 0.001 | 0.000 |
| 3 | 0.001 | 0.001 |
| 4 | 0.001 | 0.000 |
| 5 | 0.001 | 0.000 |
| 6 | 0.002 | 0.000 |
| 7 | 0.001 | 0.000 |
| 8 | 0.011 | 0.012 |
| 9 | 0.017 | 0.043 |
| 10 | 0.005 | 0.005 |
| 11 | 0.005 | 0.004 |
| 12 | 0.072 | 0.079 |
| 13 | 0.049 | 0.068 |
| 14 | 0.035 | 0.033 |
| 15 | 0.004 | 0.001 |
| 16 | 0.003 | 0.003 |
| 17 | 0.002 | 0.001 |
| 18 | 0.001 | 0.001 |

HPLC-CAD Method.

In this method, the following instrument/conditions were used:
Column: Sugar SZ5532
Column Size: 6 mm ID×150 mm L
Column Temperature: 65° C.
Detector: Corona CAD
Mobile Phase: 80% Acetonitrile in Water
Flow Rate: 1 mL/min
Volume Injected: 100 µL The HPLC column eluent is nebulized with nitrogen and the droplets are dried, producing analyte particles. A secondary stream of nitrogen becomes positively charged and transfers the charge to analyte particles. The charge is then measured, generating a signal in direct proportion to the quantity of analyte present.

Ion Chromatography (IC) Method.

In this method, the following instrument/conditions were used:

| | |
|---|---|
| Mobile Phase: | A: 30 mM NaOH; B: 200 mM NaOH |
| Flow Rate: | 1.0 mL/minute, Pressure ~2040 psi |
| Analytical Column: | CarboPac PA 10, 4 × 250 mm |
| Guard Column: | CarboPac PA 10, 4 × 50 mm |
| Column Temperature: | 30° C. |
| Detector Mode: | Integrated Amperometry |
| Detector Range: | 1 µC |
| Working Electrode: | Gold |
| Reference Electrode: | pH, Ag/AgCl |
| Autosampler Temperature: | Ambient |
| Injector Volume: | 25 µL |
| Run Time: | 30 minutes |

The gradient program used for the IC method: 100% Mobile Phase A at 0 min; 100% Mobile Phase B at 18 min; 100% Mobile Phase B at 30 min.

Applied Potential Wave Form, IC method:

| Time (Seconds) | Potential (V) | Integration |
|---|---|---|
| 0.00 | 0.10 | |
| 0.20 | 0.10 | Start |
| 0.40 | 0.10 | End |
| 0.41 | −2.00 | |
| 0.42 | −2.00 | |
| 0.43 | 0.60 | |
| 0.44 | −0.10 | |
| 0.50 | −0.10 | |

While the results of each method were generally comparable, the IC method was selected for further analysis due to greater sensitivity as compared to the HPLC-CAD method (sample concentration 1 mg/mL vs. 100 mg/mL mannitol). The Quantitation Limit (QL) of Ion Chromatography (IC) method is 0.005% of mannose in mannitol. Several lots of mannitol (see Table 18) were analyzed and the mannose values are given in below:

| Type of Mannitol | Mannitol Lot | % Mannose in Mannitol* IC Method |
|---|---|---|
| Crystalline | 1 | 0.0009 |
| Crystalline | 2 | 0.0003 |
| Crystalline | 3 | 0.0008 |
| Crystalline | 4 | 0.0002 |
| Crystalline | 5 | 0.0002 |
| Crystalline | 6 | 0.0002 |
| Crystalline | 7 | 0.0000 |
| Spray Dried | 8 | 0.0115 |
| Spray Dried | 9 | 0.0434 |
| Spray Dried | 16 | 0.0026 |
| Spray Dried | 17 | 0.0009 |
| Spray Dried | 18 | 0.0010 |

*Though the QL of the IC method is 0.005% of mannose in mannitol, in order to estimate the amount of mannose, the % mannose in mannitol was calculated using mannose peak area observed versus that of external mannose standard.

Of the 2 lots of mannitol used from the above table, spray dried lot 8 (0.0115% mannose) formed the conjugate degradant whereas crystalline mannitol lot 1 (0.0009% Mannose, <QL) did not form the conjugate degradant. The amount of mannose in mannitol appeared to be the controlling factor, not the type of mannitol used in transnorsertraline HCl formulation (i.e., crystalline vs. spray dried). This was later confirmed from the results obtained using recrystallized mannitol samples spiked with mannose in the stability study of transnorsertraline HCl formulations.

6.29 Transnorsertraline HCl Capsule Stability Study

The excipient blend or completed dosage form was prepared with the active drug. The material was stored in a HDPE bottle sealed with a heat induction foil. The material was placed in an oven with controlled humidity such that the samples are exposed to about 40° C. and about 75% RH for a period of 8 weeks. Capsule samples were prepared as follows:

| Strength (mg/capsule) | Minimum Number of Capsules Required for Duplicate Sample Preparation | Weight of Composite for Single Sample Preparation, mg | Volumetric Flask, mL | Conc. of Active, mg/mL |
|---|---|---|---|---|
| 0.5 | 30 | 4200 | 50 | 0.14 |
| 1 | 15 | 2100 | 50 | 0.14 |
| 5 | 6 | 840 | 100 | 0.14 |
| 10 | 6 | 840 | 200 | 0.14 |

Sample diluent was prepared as follows. For each liter prepared, accurately measure 600 mL of water, 200 mL of THF and 200 mL of acetonitrile into a suitable container. Add 0.5 mL of trifluoroacetic acid and mix thoroughly.

HPLC Analytic Method.

A Zorban SB-CN 5 μM, 25 cm×4.6 mm analytical column using a 0.05% trifluoroacetic acid in a 80:20 water:acetonitrile solution (Mobile Phase A) followed by a 0.05% trifluoroacetic acid in a 15:85 water:acetonitrile solution (Mobile Phase B) was used. Column temperature: 30° C. The flow rate: 1.0 mL/min. Injection volume: 50 μL. Wavelength: 220 nm. Minimum run time: 50 min (15 min delay). Mobile Phase gradient:

| Time (min) | % A | % B |
|---|---|---|
| 0 | 100 | 0 |
| 20 | 70 | 30 |
| 40 | 0 | 100 |
| 50 | 0 | 100 |
| 55 | 100 | 0 |
| 65 | 100 | 0 |

For HPLC sample preparation, the contents were transferred to a 50 mL volumetric flask. A mixture of water/actonitrile/THF/trifluoroacetic acid in the ratio 60/20/20/0.05 was used as sample diluent. After filling the flask ¾ full with sample diluent, it was vigorously shaken by hand and then subjected to wrist action shaking for 30 minutes, sonication for 20 minutes and wrist action shaking again for 30 minutes. After cooling to room temperature, the volume was made up to 50 mL using sample diluent, mixed well and filtered the supernatant using 25 mm diameter 0.45 μm PTFE GD/X syringe filter in to a HPLC vial and analyzed using the HPLC conditions shown above. The concentration of active in the samples was 0.14 mg/mL.

Table 19 shows that the same degradants are formed at different amounts in different strength capsules. 1 mg capsules contained more total degradants than 5 and/or 10 mg strengths.

TABLE 19

Stability of Transnorsertraline Prototype Capsules

40° C./75% RH Stability Chamber 8 Weeks

| Impurity RRT* | 1 mg B3 | | 5 mg B1 | | 10 mg B1 | |
|---|---|---|---|---|---|---|
| | Aclar | PVDC | Aclar | PVDC | Aclar | PVDC |
| 0.683 | 0.45 | 0.75 | 0.24 | 0.33 | 0.09 | 0.12 |
| 0.764 | 0.63 | 1.04 | 0.43 | 0.56 | 0.17 | 0.22 |
| 0.803 | 0.25 | 0.45 | 0.30 | 0.34 | 0.13 | 0.14 |
| 0.861 Synthetic Impurity 1 | 0.20 | 0.28 | 0.25 | 0.25 | 0.12 | 0.11 |
| 0.884 Synthetic Impurity 2 | 0.05 | — | — | — | — | — |
| 1.064 Cis diastereomer | — | 0.05 | — | — | — | — |
| 1.076 | — | 0.06 | 0.05 | 0.06 | — | — |
| 1.276 | 0.19 | 0.06 | — | — | — | — |
| 1.393 | 0.19 | 0.24 | 0.08 | 0.12 | — | 0.05 |
| 1.549 | 0.19 | 0.24 | 0.08 | 0.12 | — | 0.05 |
| 1.649 (Tetralone) | 0.33 | 0.45 | 0.15 | 0.20 | 0.08 | 0.10 |
| 1.703 | — | 0.06 | 0.05 | 0.07 | — | — |
| Total Impurities | 2.26% | 3.71% | 1.69% | 2.08% | 0.73% | 0.86% |

*Impurities at or above 0.05% are listed
Assumed RRF (relative response factor) of impurities = 1
PVDC = polyvinylidine chloride Similar degradants were observed using open dish conditions. Wide-mouth open dish containers (~20 mL scintillation vials) were subjected to 40° C. and about 75% RH for 3 weeks. 7.88 mg of transnorsertraline HCl and the appropriate amount of excipient(s) (active to excipient ratio of 1:1, 1:124 and/or 1:372) were weighed into the containers.

TABLE 20

Open Dish Study

| Impurity RRT* | 1 mg B3 | 5 mg B1 | 10 mg B1 |
|---|---|---|---|
| 0.683 | 0.53 | 0.13 | 0.05 |
| 0.764 | 0.82 | 0.26 | 0.11 |
| 0.803 | 0.41 | 0.20 | 0.08 |
| 0.861 Synthetic Impurity 1 | 0.28 | 0.20 | 0.11 |
| 0.884 Synthetic Impurity 2 | 0.05 | 0.05 | 0.05 |
| 1.549 | 0.14 | 0.07 | — |
| 1.649 (Tetralone) | 0.32 | 0.14 | 0.07 |
| 1.703 (TSA) | 0.05 | — | — |
| 1.937 | 0.05 | — | — |
| Total Impurities | 2.77% | 1.12% | 0.53% |

*Impurities at or above 0.05% are listed
Assumed RRF (relative response factor) of impurities = 1

Figure 9:
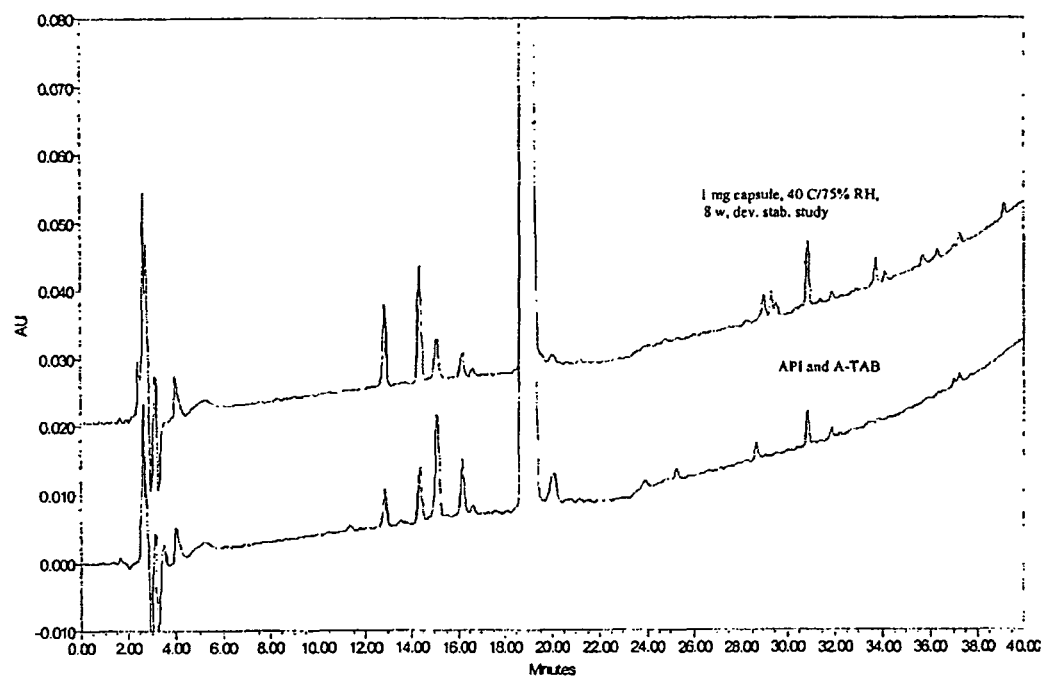
FIG. 9 is an overlay of HPLC chromatograms from the stability studies of example 6.31.

Comparison of the results presented in Tables 19 and 20 revealed that the same degradants formed at slightly different levels, and that degradation in open dish is faster. HPLC chromatograms obtained for capsule stability study and open dish study are shown in FIG. 9.

Because the 1 mg capsules produced the most impurities/degradants, the ratio of transnorsertraline (active) to excipients in the samples were kept similar to that in 1 mg capsules (1 mg of transnorsertraline is equivalent to 1.125 mg of transnorsertraline hydrochloride):

TABLE 21

Compositions of 1 mg Transnorsertraline HCl Capsule

| Capsule Formulation | (mg/capsule) |
|---|---|
| Transnorsertraline HCl | 1.125 |
| Talc (Imperial 500) | 1.125 |
| Starch 1500 | 139 |
| A-Tab | 139 |
| Ac-Di-Sol | 18.00 |
| Mallinckrodt #2257 Mag. St. | 1.50 |
| Totals: | 299.75 |

The following lots of excipients were used with various lots of Active (e.g., "Active 1"):

| Excipient |
|---|
| TALC |
| Starch 1500 1 |
| Starch 1500 2 |
| A-TAB 1 |
| A-TAB 2 |
| A-TAB 3 |
| A-TAB 4 |
| Ac-Di-Sol |
| Mg Stearate |

Conclusions.

The compatibility degradation study of transnorsertraline HCl and its excipients demonstrated that the larger the surface area of the active, the larger the amount of the degradation. Of the 5 excipients present in 1.0, 5.0 and 10.0 mg capsules, only the use of A-TAB allowed for degradation of transnorsertraline HCl, similar to that observed when developmental capsules per se were stressed, and the extent of degradation caused by A-TAB depended on the lot used. The mechanism leading to degradation of active, apparently exacerbated by the presence of A-TAB, was not determined. Individual degradants may be isolated, for example, by placing a mixture of 2 g of Active 3 and 248 g of A-TAB 2 in an open dish for 3 weeks at 40° C./75% RH. The individual degradants were isolated in about 5 to 10 mg quantities.

6.30 Open Dish Stability Study Examples

Transnorsertraline HCl (1) ("Active 1") was mixed with each excipient present in 1 mg capsule strength respectively. The samples contained two different ratios (1:1 and as in the 1 mg capsules) of active and excipients.

Set 1a Sample Matrix

Samples Placed at 40° C./75 RH for 3 Weeks*

| Sample # | Active 1 | Talc | Starch 1500 1 | A-TAB 1 | Ac-Di-Sol | Mg St. |
|---|---|---|---|---|---|---|
| 1 | 7.88 mg | — | — | — | — | — |
| 2 | 7.88 mg | 7.88 mg | — | — | — | — |
| 3 | 7.88 mg | — | 7.88 mg | — | — | — |
| 4 | 7.88 mg | — | — | 7.88 mg | — | — |
| 5 | 7.88 mg | — | — | — | 7.88 mg | — |
| 6 | 7.88 mg | — | — | — | — | 7.88 mg |

*The ratio of active to excipient is 1:1

Set 1b Sample Matrix

Samples Placed at 40° C./75 RH for 3 Weeks*

| Sample # | Active 1 | Talc | Starch 1500 1 | A-TAB 1 | Ac-Di-Sol | Mg St. |
|---|---|---|---|---|---|---|
| 7 | 7.88 mg | — | 974 mg | — | — | — |
| 8 | 7.88 mg | — | — | 974 mg | — | — |
| 9 | 7.88 mg | — | — | — | 126 mg | — |
| 10 | 7.88 mg | — | — | — | — | 10.5 mg |
| 11 | — | 7.88 mg | — | — | — | — |
| 12 | — | — | 974 mg | — | — | — |
| 13 | — | — | — | 974 mg | — | — |
| 14 | — | — | — | — | 126 mg | — |
| 15 | — | — | — | — | — | 10.5 mg |

*The ratio of active to excipient is as in 1 mg capsules

The results obtained for Set 1 experiments are shown in Tables 6 and 7.

TABLE 22

Stability of Set 1a Samples

| | % Impurities | | | | | |
|---|---|---|---|---|---|---|
| Peaks RRT | Active 1 | Active 1 + Starch 1 | Active 1 + A-TAB 1 | Active 1 + AC-Di-Sol | Active 1 + Mg Stearate | Active 1 + Talc |
| 0.764 | 0.05 | 0.04 | 0.05 | 0.03 | 0.04 | 0.05 |
| 0.862, Synthetic Impurity 1 | 0.04 | 0.04 | 0.04 | 0.03 | 0.04 | 0.04 |
| 0.885, Synthetic Impurity 2 | 0.05 | 0.05 | 0.05 | 0.05 | 0.05 | 0.06 |
| 1.07, cis-diastereomer | 0.12 | 0.10 | 0.10 | 0.10 | 0.11 | 0.10 |
| 1.386 | 0.07 | 0.07 | 0.06 | 0.05 | 0.06 | 0.07 |
| 1.642, Tetralone | — | — | — | — | 0.02 | — |
| % Total Impurities | 0.33 | 0.30 | 0.30 | 0.26 | 0.32 | 0.32 |
| % Active | 99.68 | 99.69 | 99.70 | 99.74 | 99.68 | 99.68 |

*The ratio of Active to excipient is 1:1

As shown in Table 22, when the ratio of active 1 to excipient is 1:1, no appreciable impurities formed due to the presence of various excipients. Only a small amount of tetralone was observed.

When the ratio was changed to that as in 1 mg capsules, excipients such as starch, formulations containing Ac-Di-Sol, magnesium stearate demonstrated a small growth of the tetralone impurity (RRT 1.64, Table 7). A-TAB 1 appeared to cause the most degradation. The unknown impurities/degradants at RRT 0.61, 0.68, 0.78, 0.80, 1.34, 1.53 and 1.70 are present at or above 0.10% levels in this sample, and some degradants approached the 1.0% level. Known impurities such as synthetic impurity 1, the cis-diastereomer and tetralone grew 3-4 times more with A-TAB 1 than in active 1 alone.

TABLE 23

Stability of Set 1b Samples

| Peaks RRT | % Impurities | | | | | |
|---|---|---|---|---|---|---|
| | Active 1 | Active 1 + Starch 1 | Active 1 + A-TAB 1 | Active 1 + Ac-Di-Sol | Active 1 + Mg Stearate | Active 1 + Talc |
| 0.606 | — | — | 0.09 | — | — | — |
| 0.683 | — | — | 0.54 | — | — | — |
| 0.764 | 0.05 | 0.05 | 0.45 | 0.05 | 0.04 | 0.05 |
| 0.803 | — | — | 0.53 | — | — | — |
| 0.862, Synthetic Impurity 1 | 0.04 | 0.03 | 0.11 | 0.05 | 0.04 | 0.04 |
| 0.885, Synthetic Impurity 2 | 0.05 | 0.05 | 0.05 | 0.05 | 0.05 | 0.06 |
| 0.939 | — | — | 0.03 | — | — | — |
| 1.07, cis-diastereomer | 0.12 | 0.11 | 0.43 | 0.08 | 0.09 | 0.10 |
| 1.127 | — | — | 0.03 | — | — | — |
| 1.271 | — | — | 0.07 | — | — | — |
| 1.343 | — | — | 0.13 | — | — | — |
| 1.386 | 0.07 | 0.06 | 0.02 | 0.06 | 0.05 | 0.07 |
| 1.526 | — | — | 0.18 | — | — | — |
| 1.642, Tetralone | — | 0.09 | 0.23 | 0.05 | 0.03 | — |
| 1.696 | — | — | 0.12 | — | — | — |
| % Total Impurities | 0.33 | 0.39 | 3.01 | 0.34 | 0.30 | 0.32 |
| % ACTIVE | 99.68 | 99.61 | 97.00 | 99.74 | 99.68 | 99.68 |

*The ratio of active to excipient is as in 1 mg capsules

For Set 2 experiments, 3 different lots of active were mixed with each of 3 different lots of A-TAB separately and in 3 different ratios (1:124, 1:372) as shown in Set 2a and Set 2b, respectively.

Set 2a Sample Matrix

Open Dish - Samples at 40° C./75% RH for 2 Weeks*

| Sample # | Active 1 | Active 2 | Active 3 | A-TAB 2 | A-TAB 3 | A-TAB 4 (Powder) |
|---|---|---|---|---|---|---|
| 10 | 7.88 mg | — | — | 974 mg | — | — |
| 11 | — | 7.88 mg | — | 974 mg | — | — |
| 12 | — | — | 7.88 mg | 974 mg | — | — |
| 13 | 7.88 mg | — | — | — | 974 mg | — |
| 14 | — | 7.88 mg | — | — | 974 mg | — |
| 15 | — | — | 7.88 mg | — | 974 mg | — |
| 16 | 7.88 mg | — | — | — | — | 974 mg |
| 17 | — | 7.88 mg | — | — | — | 974 mg |
| 18 | — | — | 7.88 mg | — | — | 974 mg |

The ratio of active to excipient is 1:124

Set 2b Sample Matrix

Open Dish - Samples at 40° C./75% RH for 2 Weeks*

| Sample # | Active 1 | Active 2 | Active 3 | A-TAB 2: | A-TAB 3 | A-TAB 4 (Powder) |
|---|---|---|---|---|---|---|
| 19 | 7.88 mg | — | — | 2.92 g | — | — |
| 20 | — | 7.88 mg | — | 2.92 g | — | — |
| 21 | — | — | 7.88 mg | 2.92 g | — | — |
| 22 | 7.88 mg | — | — | — | 2.92 g | — |
| 23 | — | 7.88 mg | — | — | 2.92 g | — |
| 24 | — | — | 7.88 mg | — | 2.92 g | — |
| 25 | 7.88 mg | — | — | — | — | 2.92 g |
| 26 | — | 7.88 mg | — | — | — | 2.92 g |
| 27 | — | — | 7.88 mg | — | — | 2.92 g |

The ratio of active to excipient is 1:372

The results from the samples in Set 2a containing active and excipient in the ratio 1:124 are tabulated in Table 24.

TABLE 24

Stability of Set 2a Samples*

| Peaks RRT | % Impurities | | | | | | | | |
|---|---|---|---|---|---|---|---|---|---|
| | Active 1 + A-TAB 2 | Active 1 + A-TAB 3 | Active 1 + A-TAB 4 | Active 2 + A-TAB 2 | Active 2 + A-TAB 3 | Active 2 + A-TAB 4 | Active 3 + A-TAB 2 | Active 3 + A-TAB 3 | Active 3 + A-TAB 4 |
| 0.683 | 0.04 | 0.03 | — | 0.10 | 0.05 | — | 0.21 | 0.10 | — |
| 0.764 | 0.08 | 0.06 | 0.05 | 0.12 | 0.08 | 0.04 | 0.29 | 0.11 | 0.04 |
| 0.803 | 0.07 | 0.02 | — | 0.20 | 0.09 | — | 0.6 | 0.13 | — |
| 0.862, Synthetic Impurity 1 | 0.07 | 0.05 | 0.03 | 0.14 | 0.06 | 0.05 | 0.36 | 0.06 | 0.05 |
| 0.885, Synthetic Impurity 2 | 0.06 | 0.05 | 0.05 | 0.05 | 0.04 | 0.04 | 0.06 | 0.06 | 0.07 |
| 1.07, cis-diastereomer | 0.14 | 0.11 | 0.07 | 0.12 | 0.07 | 0.02 | 0.27 | 0.14 | 0.06 |

TABLE 24-continued

Stability of Set 2a Samples*

| Peaks RRT | % Impurities | | | | | | | | |
|---|---|---|---|---|---|---|---|---|---|
| | Active 1 + A-TAB 2 | Active 1 + A-TAB 3 | Active 1 + A-TAB 4 | Active 2 + A-TAB 2 | Active 2 + A-TAB 3 | Active 2 + A-TAB 4 | Active 3 + A-TAB 2 | Active 3 + A-TAB 3 | Active 3 + A-TAB 4 |
| 1.127, Sertraline | 0.02 | — | — | — | — | — | — | 0.02 | 0.03 |
| 1.271 | — | — | — | 0.03 | — | — | 0.05 | 0.03 | — |
| 1.343 | — | — | — | 0.03 | — | — | 0.05 | 0.02 | — |
| 1.386 | 0.03 | 0.05 | 0.05 | — | — | — | — | — | — |
| 1.526 | — | — | — | 0.04 | — | — | 0.09 | 0.03 | — |
| 1.642, Tetralone | 0.05 | 0.04 | 0.06 | 0.07 | 0.06 | 0.06 | 0.14 | 0.10 | 0.06 |
| 1.696 | — | — | — | — | — | — | 0.04 | — | — |
| 1.931 | 0.02 | — | — | — | — | — | — | — | — |
| % Total Impurities | 0.58 | 0.41 | 0.31 | 0.90 | 0.45 | 0.21 | 2.16 | 0.80 | 0.31 |
| % Active | 99.41 | 99.60 | 99.69 | 99.08 | 99.56 | 99.80 | 97.81 | 99.20 | 99.68 |

*The ratio of active to excipient is 1:124

The results of Table 24 show that varying the amount of A-TAB while keeping the amount of Active fixed resulted in the most degradation. Varying the amount of Active while keeping the amount of A-TAB fixed resulted in Active 3 providing the most impurities. The combination of Active 3 and A-TAB 2 provided the greatest amount of total impurities/degradation. The surface area of the lots of Active decreased from Active 3 to Active 4 to Active 2 to Active 1. Thus, the surface area of Active may play a part in the susceptibility of Active to degradation.

A-TAB 4, the powdered lot, provided only a small amount of tetralone. When the ratio of active to excipient was increased to 1:372, three times more than that present in 1 mg capsules, the total impurities formed remained almost the same as that found in 1:124 ratio. See Tables 24 and 25. It appears that the total impurities formed reached a plateau at a certain ratio of active to excipient.

6.31: Isolation and Identification of Degradants of Formula (III)

Samples used for preparation and isolation of degradants of formula (III) were prepared as follows: To a 500 mL brown glass bottle, 2.25 g of Active and 278 g of A-TAB were mixed by hand for 1 minute. The resulting mixture was passed through 35 mesh sieve, twice, such that the material remaining in the sieve was minimal. The sample was mixed again in a Turbula mixer at 22 rpm for 20 minutes. The mixture was then transferred to a crystallizing dish and the open container was placed at 40° C./75% RH for 3 weeks. An aliquot of the mixture was analyzed at 2 and 3 weeks. The sample was removed from the heating chamber after 3 weeks and stored refrigerated.

From the degraded sample, 62 g of the mixture was weighed in to a 1-L erlenmeyer flask. A volume of 500 mL of methanol was added and stirred at room temperature using a

TABLE 25

Stability of Set 2b Samples*

| Peaks RRT | % Impurities | | | | | | | | |
|---|---|---|---|---|---|---|---|---|---|
| | Active + A-TAB 2 | Active + A-TAB 3 | Active + A-TAB 4 | Active + A-TAB 2 | Active + A-TAB 3 | Active + A-TAB 4 | Active 3 + A-TAB 2 | Active 3 + A-TAB 3 | Active 3 + A-TAB 4 |
| 0.683 | 0.07 | 0.02 | — | 0.09 | 0.11 | 0.01 | 0.18 | 0.10 | 0.05 |
| 0.764 | 0.1 | 0.06 | 0.05 | 0.1 | 0.12 | 0.04 | 0.23 | 0.11 | — |
| 0.803 | 0.12 | — | — | 0.14 | 0.16 | — | 0.50 | 0.13 | — |
| 0.862, Synthetic Impurity 1 | 0.07 | 0.06 | 0.04 | 0.10 | 0.10 | 0.05 | 0.30 | 0.06 | 0.04 |
| 0.885, Synthetic Impurity 2 | 0.06 | 0.06 | 0.06 | 0.05 | 0.04 | 0.04 | 0.07 | 0.06 | 0.07 |
| 1.07, cis-diastereomer | 0.17 | 0.12 | 0.11 | 0.11 | 0.12 | 0.02 | 0.25 | 0.14 | 0.04 |
| 1.127, Sertraline | — | — | — | — | — | — | — | 0.02 | — |
| 1.271 | — | — | — | — | — | — | 0.05 | 0.03 | — |
| 1.343 | 0.03 | — | — | — | — | — | 0.07 | 0.02 | — |
| 1.386 | 0.03 | 0.04 | 0.05 | 0.03 | — | — | — | — | — |
| 1.526 | 0.03 | — | 0.02 | — | — | 0.03 | 0.09 | 0.03 | 0.03 |
| 1.642, Tetralone | 0.07 | 0.04 | 0.05 | 0.07 | 0.11 | 0.11 | 0.13 | 0.1 | 0.07 |
| 1.696 | — | — | — | — | — | — | 0.03 | — | — |
| 1.931 | 0.04 | — | — | — | — | — | — | — | — |
| % Total Impurities | 0.79 | 0.40 | 0.38 | 0.69 | 0.76 | 0.30 | 1.90 | 0.80 | 0.30 |
| % Active | 99.2 | 99.60 | 99.62 | 99.29 | 99.23 | 99.7 | 98.06 | 99.20 | 99.70 |

*The ratio of active to excipient is 1:372 magnetic stir bar for 1 hour. The stirred mixture was allowed to settle for 30 minutes. The supernatant was vacuum filtered using a MAGNA, Nylon supported, plain, 0.45 μm filter. The small amount of powder on the filter paper was washed with methanol and the rinses combined. The filtrate was analyzed using the HPLC method described below. The sample diluent was methanol. The total area obtained by adding the peak areas of active and the impurities was quantitated using a standard solution of active. The amount of active and all the impurities thus extracted was 369.2 mg. The solid in the erlenmeyer flask was treated again with another 500 mL of methanol.

By repeating the same procedure as described above, the amount of active and all the impurities extracted the second time was 38.5 mg. The two filtrates were combined and methanol was removed using a rotary evaporator. An orange yellow solid remained at the bottom of the flask. A mixture of 6.5 mL of methanol and 3 mL of water was added. The solid dissolved forming an orange yellow solution. This solution was centrifuged at room temperature and the clear supernatant was transferred to a 10 mL glass vial and stored refrigerated.

HPLC Separation of the 4 Major Degadants.

The following semi-preparative HPLC conditions were developed and used to separate the 4 major impurities from the open dish forced degraded sample solution prepared as described above.

| HPLC column: | Zorbax SB-CN (Agilent), 9.2 mm × 250 mm, 5 μm |
| --- | --- |
| Mobile phase A: | 0.1% formic acid in water |
| Mobile phase B: | 0.1% formic acid in acetonitrile |
| Wavelength: | 220 nm |
| Volume injected: | 10 μL |
| Flow rate: | 4 mL/min |
| Run time: | 44 minutes |

| | Time in minutes | % A | % B |
| --- | --- | --- | --- |
| Gradient used: | 0 | 80 | 20 |
| | 20 | 80 | 20 |
| | 22 | 0 | 100 |
| | 30 | 0 | 100 |
| | 32 | 80 | 20 |
| | 44 | 80 | 20 |

Only the 4 major impurities were fraction collected. Active and other impurities were washed off the column. Approximately 35 injections were made and the fractions of each degradant were pooled separately. Each of the 4 pools was then analyzed using HPLC. The analytical column separation of the 4 pools is shown in FIG. 9. Impurities 1 and 3 were each 100% pure. Impurity 2 was 98% pure. Fraction 4 was found to be a mixture of impurities 4 and 5 present in the ratio 63:37.

Structural Identification of Deagradants of Formula (III).

Degradation products of active were isolated using semi-preparative HPLC (Zorbax SB-SN, 5 um, 9.2×250 mm; 20% ACN/$H_2O$ with 0.1% formic acid as mobile phase, 4 mL/min) with the aforementioned open dish degradation sample. Fractions containing these impurities were neutralized with 0.1 M $NH_4OAc$ before drying under vacuum to prevent possible decomposition.

All impurities were initially analyzed with LC-MS, fragmentation and high resolution MS-analyses. Degradants III-a and III-b showed almost identical mass spectral characteristics. [M+H$^+$] at m/z 308 for both compounds was observed while the isotopic pattern confirmed the bis-chloro nature of the molecules, indicating their transnorsertraline origin. The difference of 16 mass units in molecular weight of transnorsertraline versus that of Degradants III-a and III-b suggested that both impurities could be oxidation products of transnorsertraline in the form of hydroxyl group. The loss of $H_2O$ (−18 mu) in MS fragmentation suggested that the hydroxyl group might reside on the aliphatic ring.

Isolation effort for Degradant III-a yielded a small amount of relatively pure compound. The $^1H$ NMR spectrum of Degradant III-a in ACN-d3 revealed that (a) the aromatic rings of transnorsertraline were not altered as evidenced by the aromatic proton signals and patterns, and (b) one of the benzylic protons of transnorsertraline was substituted as only one was observed at 4.16 ppm. Because the mass spectral data had confirmed that the amino group was not changed in this impurity, the only other position for a benzylic hydroxyl group is the position 4. Therefore, Degradant III-a was identified as 4-hydroxy transnorsertraline.

Isolated Degradant III-b showed a very similar pattern in its $^1H$ NMR spectrum, i.e., unaltered aromatic rings and the disappearance of one benzylic proton. This information together with its mass spectral data led to the conclusion that impurities 1 and 2 were a diastereomeric pair of 4-hydroxy transnorsertraline.

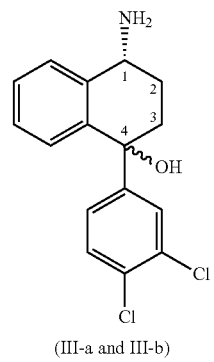 [SMILES: N[C@@H]1CCC(O)(c2ccc(Cl)c(Cl)c2)c2ccccc21]

(III-a and III-b)

Impurities 3 and 4 share the same molecular weight of 323 with almost identical MS fragmentation pattern. After the isolation and drying process, it was noticed that impurities 3 and 4 were converted to impurities 1 and 2 respectively (by HPLC retention time, MS data and $^1H$ NMR spectrum). As noted above, in order to minimize the possible decomposition during the isolation process, $NH_4OAc$ was used to neutralize the formic acid in the collected fractions, which may have resulted in the conversion.

Additional experiments showed that freshly isolated Degradant-III-c and III-d fractions without $NH_4OAc$ were relatively stable even after a few days at room temperature. However, in the presence of $NH_4OAc$, almost 50% of the compounds were converted after 24 hours. Furthermore, it was observed that upon drying under vacuum, Degradants III-c and III-d were converted to Degradants III-a and III-b independent of the presence of $NH_4OAc$. Because the molecular formula difference between Degradants III-c and III-a was one oxygen atom as measured by HR-MS, it was concluded that Degradants II-c and III-d were a diasteromeric pair of 4-hydroperoxy transnorsertraline. The conversions from impurity 3 and Degradant III-d to Degradants III-a and III-b may be by a decomposition process of hydroperoxides.

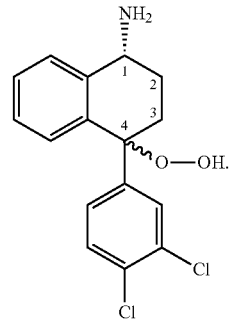

(III-c and III-d)

6.31: Stability Studies of Transnorsertraline with Mannitol

Three recrystallized mannitol lots spiked with mannose were selected for further study based on their % mannose values. Crystalline mannitol and spray dried mannitol were used as controls. The recrystallized spray dried mannitol lot was also used in the study to determine whether the type of mannitol used (crystalline vs. spray dried) was significant. Transnorsertraline HCl blends were made using the selected mannitol lots and placed at 30° C./65% RH under open dish conditions and analyzed initially and then at 2, 4 and 6 weeks using HPLC. The results are shown in Table 26.

TABLE 26

Amount of Degradant II in Transnorsertraline HCl Blends

| Active Blend Lot | Mannitol Lot | % Mannose (IC Method) | % Degradant in 2 weeks | % Degradant in 4 weeks | % Degradant in 6 weeks |
|---|---|---|---|---|---|
| 1 | 1 | 0.000 | 0.00 | 0.00 | 0.00 |
| 2 | 2 | 0.001 | 0.02 | 0.06 | 0.05 |
| 3 | 3 | 0.005 | 0.12 | 0.12 | 0.12 |
| 4 | 4 | 0.012 | 0.24 | 0.19 | 0.16 |
| 5 | 5 | 0.033 | 0.67 | 0.62 | 0.61 |
| 6 | 6 | 0.079 | 0.93 | 1.28 | 0.99 |

All of the patents, patent applications and publications referred to in this application are incorporated herein in their entireties. Moreover, citation or identification of any reference in this application is not an admission that such reference is available as prior art.

What is claimed is:

1. A tablet, comprising a tablet core and an optional coating, said tablet core consisting of:
   (a) transnorsertraline or pharmaceutically acceptable salt or solvate thereof;
   (b) mannitol or xylitol; and
   (c) one or more of
      (i) a disintegrant;
      (ii) a lubricant; and
      (iii) an anti-caking agent.

2. A capsule consisting of:
   (a) a gelatin capsule shell;
   (a) transnorsertraline or pharmaceutically acceptable salt or solvate thereof;
   (b) mannitol or xylitol;
   (c) one or more of
      (i) a disintegrant;
      (ii) a lubricant; and
      (iii) an anti-caking agent.

3. A tablet according to claim 1 wherein said disintegrant is chosen from croscarmellose sodium and sodium starch glycolate.

4. A tablet according to claim 1 wherein said lubricant is chosen from magnesium stearate, calcium stearate, zinc stearate and stearic acid.

5. A tablet according to claim 1 wherein said anti-caking agent is chosen from talc, kaolin and bentonite.

6. A capsule according to claim 2 wherein said disintegrant is chosen from croscarmellose sodium and sodium starch glycolate.

7. A capsule according to claim 2 wherein said lubricant is chosen from magnesium stearate, calcium stearate, zinc stearate and stearic acid.

8. A capsule according to claim 2 wherein said anti-caking agent is chosen from talc, kaolin and bentonite.

* * * * *